United States Patent
Andreyev et al.

(10) Patent No.: US 10,675,623 B2
(45) Date of Patent: Jun. 9, 2020

(54) DEVICES AND METHODS FOR THE DETECTION OF MOLECULES USING A FLOW CELL

(71) Applicant: Visby Medical, Inc., San Jose, CA (US)

(72) Inventors: Boris Andreyev, Foster City, CA (US); Rajinder K. Bhatia, Newark, CA (US); Victor Briones, Gilroy, CA (US); Phoebe Cao, San Jose, CA (US); Jesus Ching, Saratoga, CA (US); Brian Ciopyk, Pleasanton, CA (US); Adam De La Zerda, Palo Alto, CA (US); Jonathan H. Hong, San Jose, CA (US); Helen Huang, San Pablo, CA (US); Colin Kelly, San Francisco, CA (US); Adrienne C. Lam, Fremont, CA (US); Gregory Loney, Los Altos, CA (US); Danielle McSheery, San Mateo, CA (US); Keith E. Moravick, Mountain View, CA (US); Valeria Revilla, East Palo Alto, CA (US); Shaunak Roy, Sunnyvale, CA (US); David D. Swenson, Santa Clara, CA (US)

(73) Assignee: Visby Medical, Inc., San Jose, CA (US)

( * ) Notice: Subject to any disclaimer, the term of this patent is extended or adjusted under 35 U.S.C. 154(b) by 0 days.

(21) Appl. No.: 16/229,741

(22) Filed: Dec. 21, 2018

(65) Prior Publication Data
US 2019/0151844 A1 May 23, 2019

Related U.S. Application Data

(63) Continuation of application No. PCT/US2017/039844, filed on Jun. 28, 2017.
(Continued)

(51) Int. Cl.
*B01L 3/00* (2006.01)
*C12Q 1/686* (2018.01)
(Continued)

(52) U.S. Cl.
CPC ..... *B01L 3/502715* (2013.01); *B01L 3/50273* (2013.01); *B01L 7/525* (2013.01);
(Continued)

(58) Field of Classification Search
None
See application file for complete search history.

(56) References Cited

U.S. PATENT DOCUMENTS

| 3,697,227 A | 10/1972 | Goldstein et al. |
| 4,710,355 A | 12/1987 | Ushikubo |

(Continued)

FOREIGN PATENT DOCUMENTS

| EP | 2682480 A1 | 1/2014 |
| WO | WO2001/049416 A1 | 7/2001 |

(Continued)

OTHER PUBLICATIONS

Australian Search Report for Austrailian Application No. 2015373998, dated Feb. 21, 2020.*
(Continued)

*Primary Examiner* — Robert T. Crow
(74) *Attorney, Agent, or Firm* — ReavesColey PLLC

(57) ABSTRACT

A method includes conveying a detection solution containing a target amplicon into a detection module of a molecular diagnostic test device. The detection module includes a detection surface including a series of capture probes to which a first portion of the target amplicon is bound when the detection solution is conveyed. A first reagent formulated to produce a visible signal indicating a presence of the target amplicon is then conveyed into the detection module. The
(Continued)

first reagent is bound to a second portion of the target amplicon when the first reagent is conveyed. A second reagent is conveyed into the detection module. The second reagent includes a precipitating substrate formulated to catalyze the production of the visible signal by producing an insoluble colored product when the second reagent is in contact with the first reagent. The method includes viewing the visible signal via a transparent portion of the detection module.

21 Claims, 41 Drawing Sheets

Specification includes a Sequence Listing.

Related U.S. Application Data

(60) Provisional application No. 62/356,464, filed on Jun. 29, 2016, provisional application No. 62/356,596, filed on Jun. 30, 2016.

(51) Int. Cl.
*B01L 7/00* (2006.01)
*C12Q 1/68* (2018.01)

(52) U.S. Cl.
CPC .............. *C12Q 1/68* (2013.01); *C12Q 1/686* (2013.01); *B01L 2200/026* (2013.01); *B01L 2200/027* (2013.01); *B01L 2300/045* (2013.01); *B01L 2300/046* (2013.01); *B01L 2300/0654* (2013.01); *B01L 2300/0663* (2013.01); *B01L 2300/168* (2013.01); *B01L 2400/0478* (2013.01)

(56) References Cited

U.S. PATENT DOCUMENTS

| | | | |
|---|---|---|---|
| 4,789,630 A * | 12/1988 | Bloch | C12Q 1/28 435/28 |
| 4,889,692 A | 12/1989 | Holtzman | |
| RE33,858 E | 3/1992 | Gropper et al. | |
| 5,164,159 A | 11/1992 | Hayashi et al. | |
| 5,229,297 A | 7/1993 | Schnipelsky et al. | |
| 5,270,183 A | 12/1993 | Corbett et al. | |
| 5,273,905 A | 12/1993 | Muller et al. | |
| 5,405,585 A | 4/1995 | Coassin | |
| 5,429,807 A | 7/1995 | Matson et al. | |
| 5,498,392 A | 3/1996 | Wilding et al. | |
| 5,631,165 A | 5/1997 | Chupp et al. | |
| 5,633,168 A | 5/1997 | Glasscock et al. | |
| 5,660,993 A | 8/1997 | Cathey et al. | |
| 5,773,234 A | 1/1998 | Pronovost et al. | |
| 5,726,026 A | 3/1998 | Wilding et al. | |
| 5,882,903 A | 3/1999 | Andrevski et al. | |
| 5,922,591 A | 7/1999 | Anderson et al. | |
| 5,952,664 A | 9/1999 | Wake et al. | |
| 5,976,470 A | 11/1999 | Maiefski et al. | |
| 6,039,924 A | 3/2000 | Horn | |
| 6,126,804 A | 10/2000 | Andresen | |
| 6,146,591 A | 11/2000 | Miller | |
| 6,153,425 A | 11/2000 | Kozwich et al. | |
| 6,235,479 B1 | 5/2001 | Rogers | |
| 6,261,431 B1 | 7/2001 | Mathies et al. | |
| 6,303,081 B1 | 10/2001 | Mink et al. | |
| 6,313,471 B1 | 11/2001 | Giebeler et al. | |
| 6,365,378 B1 | 4/2002 | Hirota et al. | |
| 6,369,893 B1 | 4/2002 | Christel et al. | |
| 6,374,684 B1 | 4/2002 | Dority | |
| 6,426,215 B1 | 7/2002 | Sandell | |
| 6,514,750 B2 | 2/2003 | Bordenkircher et al. | |
| 6,610,499 B1 | 8/2003 | Fulwyler et al. | |
| 6,645,758 B1 | 11/2003 | Schnipelsky et al. | |
| 6,649,378 B1 | 11/2003 | Kozwich et al. | |
| 6,656,744 B2 | 12/2003 | Pronovost et al. | |
| 6,677,151 B2 | 1/2004 | Sandell | |
| 6,767,512 B1 | 7/2004 | Lurz et al. | |
| 6,780,380 B2 | 8/2004 | Hunnell et al. | |
| 6,780,617 B2 | 8/2004 | Chen | |
| 6,781,056 B1 | 8/2004 | O'Rourke et al. | |
| 6,813,568 B2 | 11/2004 | Powell et al. | |
| 6,821,771 B2 | 11/2004 | Festoc | |
| 6,875,403 B2 | 4/2005 | Liu et al. | |
| 6,893,879 B2 | 5/2005 | Petersen et al. | |
| 6,901,217 B2 | 5/2005 | Gamboa et al. | |
| 6,911,181 B1 | 6/2005 | McNeil | |
| 6,990,290 B2 | 1/2006 | Kylberg et al. | |
| 7,041,481 B2 | 5/2006 | Anderson et al. | |
| 7,144,742 B2 | 12/2006 | Boehringer et al. | |
| 7,179,639 B2 | 2/2007 | Pottathil et al. | |
| 7,189,522 B2 | 3/2007 | Esfandiari | |
| 7,192,721 B1 | 3/2007 | Esfandiari | |
| 7,235,216 B2 | 6/2007 | Kiselev et al. | |
| 7,297,313 B1 | 11/2007 | Northrup et al. | |
| 7,341,697 B2 | 3/2008 | Takeuchi et al. | |
| 7,377,291 B2 | 5/2008 | Moon et al. | |
| 7,378,285 B2 | 5/2008 | Lambotte et al. | |
| 7,384,782 B2 | 6/2008 | Nakatani et al. | |
| 7,416,892 B2 | 8/2008 | Battrell et al. | |
| 7,438,852 B2 | 10/2008 | Tung et al. | |
| 7,459,302 B2 | 12/2008 | Reid et al. | |
| 7,491,551 B2 | 2/2009 | Boehringer et al. | |
| 7,517,495 B2 | 4/2009 | Wu et al. | |
| 7,544,324 B2 | 6/2009 | Tung et al. | |
| 7,550,112 B2 | 6/2009 | Gou et al. | |
| 7,553,675 B2 | 6/2009 | Jerome et al. | |
| 7,569,382 B2 | 8/2009 | Li | |
| 7,579,172 B2 | 8/2009 | Cho et al. | |
| 7,592,139 B2 | 9/2009 | West et al. | |
| 7,632,687 B2 | 12/2009 | Gokhan | |
| 7,648,835 B2 | 1/2010 | Breidford et al. | |
| 7,682,801 B2 | 3/2010 | Esfandiari | |
| 7,691,644 B2 | 4/2010 | Lambotte et al. | |
| 7,705,339 B2 | 4/2010 | Smith et al. | |
| 7,709,250 B2 | 5/2010 | Corbett et al. | |
| 7,754,452 B2 | 7/2010 | Kim et al. | |
| 7,767,439 B2 | 8/2010 | Oh et al. | |
| 7,794,656 B2 | 9/2010 | Liang et al. | |
| 7,799,521 B2 | 9/2010 | Chen et al. | |
| 7,837,939 B2 | 11/2010 | Tung et al. | |
| 7,858,396 B2 | 12/2010 | Corstjens et al. | |
| 7,871,568 B2 | 1/2011 | Liang et al. | |
| 7,879,293 B2 | 2/2011 | Niedbala et al. | |
| 7,914,986 B2 | 3/2011 | Nunn | |
| 7,915,013 B2 | 3/2011 | Cho et al. | |
| 7,959,877 B2 | 6/2011 | Esfandiari | |
| 7,985,716 B2 | 7/2011 | Yershov et al. | |
| 7,988,915 B2 | 8/2011 | Lee et al. | |
| 7,998,757 B2 | 8/2011 | Darrigrand et al. | |
| 8,008,046 B2 | 8/2011 | Maltezos et al. | |
| 8,008,080 B2 | 8/2011 | Tokhtuev et al. | |
| 8,012,427 B2 | 9/2011 | Bommarito et al. | |
| 8,018,593 B2 | 9/2011 | Tan et al. | |
| 8,048,386 B2 | 11/2011 | Dority et al. | |
| 8,062,883 B2 | 11/2011 | Woudenberg et al. | |
| 8,075,854 B2 | 12/2011 | Yang et al. | |
| 8,088,616 B2 | 1/2012 | Handique | |
| 8,110,392 B2 | 2/2012 | Battrell et al. | |
| 8,133,671 B2 | 3/2012 | Williams et al. | |
| 8,133,703 B2 | 3/2012 | Ching et al. | |
| 8,163,489 B2 | 4/2012 | Murray et al. | |
| 8,163,535 B2 | 4/2012 | Reed et al. | |
| 8,169,610 B2 | 5/2012 | Oldham et al. | |
| 8,173,077 B2 | 5/2012 | Korampally et al. | |
| 8,187,557 B2 | 5/2012 | Van Atta et al. | |
| 8,198,074 B2 | 6/2012 | Moriwaki et al. | |
| 8,216,832 B2 | 7/2012 | Battrell et al. | |
| 8,231,844 B2 | 7/2012 | Gorfinkel | |
| 8,232,091 B2 | 7/2012 | Maltezos et al. | |
| 8,232,094 B2 | 7/2012 | Hasson et al. | |
| 8,247,221 B2 | 8/2012 | Fawcett | |
| 8,263,392 B2 | 9/2012 | Gale et al. | |

(56) References Cited

U.S. PATENT DOCUMENTS

| | | |
|---|---|---|
| 8,277,763 B2 | 10/2012 | Steinmann et al. |
| 8,278,091 B2 | 10/2012 | Rutter et al. |
| 8,298,763 B2 | 10/2012 | Regan |
| 8,323,583 B2 | 12/2012 | Gou et al. |
| 8,329,453 B2 | 12/2012 | Battrell et al. |
| 8,343,442 B2 | 1/2013 | McBride et al. |
| 8,343,754 B2 | 1/2013 | Wittwer et al. |
| 8,357,490 B2 | 1/2013 | Froehlich et al. |
| 8,372,340 B2 | 2/2013 | Bird et al. |
| 8,389,960 B2 | 3/2013 | Pieprzyk et al. |
| 8,394,608 B2 | 3/2013 | Ririe et al. |
| 8,394,626 B2 | 3/2013 | Ramsey et al. |
| 8,426,134 B2 | 4/2013 | Piepenburg et al. |
| 8,435,461 B2 | 5/2013 | Kirby et al. |
| 8,448,824 B2 | 5/2013 | DiPerna |
| 8,492,136 B2 | 7/2013 | Carlisle et al. |
| 8,507,259 B2 | 8/2013 | Esfandiari |
| 8,580,575 B2 | 11/2013 | Hanafusa |
| 8,597,937 B2 | 12/2013 | Ward et al. |
| 8,603,835 B2 | 12/2013 | Esfandiari |
| 8,617,486 B2 | 12/2013 | Kirby et al. |
| 8,629,264 B2 | 1/2014 | Reed et al. |
| 8,637,250 B2 | 1/2014 | Jenison |
| 8,663,976 B2 | 3/2014 | Chung et al. |
| 8,673,239 B2 | 3/2014 | Niedbala et al. |
| 8,691,561 B2 | 4/2014 | Igata |
| 8,722,426 B2 | 5/2014 | Lambotte et al. |
| 8,728,765 B2 | 5/2014 | Ching et al. |
| 8,735,103 B2 | 5/2014 | Chung et al. |
| 8,765,454 B2 | 7/2014 | Zhou et al. |
| 8,772,017 B2 | 7/2014 | Battrell et al. |
| 8,795,592 B2 | 8/2014 | Eiriksson |
| 8,859,199 B2 | 10/2014 | Hellyer et al. |
| 8,865,458 B2 | 10/2014 | Ramsey et al. |
| 8,871,155 B2 | 10/2014 | Wu et al. |
| 8,877,450 B2 | 11/2014 | Esfandiari |
| 8,894,946 B2 | 11/2014 | Nielsen et al. |
| 8,895,255 B1 | 11/2014 | Goldberg et al. |
| 8,900,828 B2 | 12/2014 | Smith et al. |
| 8,900,853 B2 | 12/2014 | Verhaar et al. |
| 8,911,941 B2 | 12/2014 | Michlitsch |
| 8,911,949 B2 | 12/2014 | Bertrand et al. |
| 8,916,375 B2 | 12/2014 | Landers et al. |
| 8,945,843 B2 | 2/2015 | Alvino et al. |
| 8,975,027 B2 | 3/2015 | Gale et al. |
| 8,980,177 B2 | 3/2015 | Carlisle et al. |
| 8,980,561 B1 | 3/2015 | Cai et al. |
| 8,986,927 B2 | 3/2015 | Lee et al. |
| 8,992,854 B2 | 3/2015 | Brewster et al. |
| 9,011,770 B2 | 4/2015 | Wu et al. |
| 9,012,236 B2 | 4/2015 | Jovanovich et al. |
| 9,023,639 B2 | 5/2015 | Kim et al. |
| 9,044,729 B2 | 6/2015 | Rengifo et al. |
| 9,207,236 B2 | 12/2015 | Cary |
| 9,207,241 B2 | 12/2015 | Lambotte et al. |
| 9,243,288 B2 | 1/2016 | Ness et al. |
| 9,260,750 B2 | 2/2016 | Hillebrand et al. |
| 9,268,911 B2 | 2/2016 | Sia et al. |
| 9,387,478 B2 | 7/2016 | Bergstedt et al. |
| 9,445,749 B2 | 9/2016 | Erickson et al. |
| 9,469,871 B2 | 10/2016 | Bearinger et al. |
| 9,475,049 B2 | 10/2016 | Siciliano |
| D776,290 S | 1/2017 | Wan et al. |
| 9,623,415 B2 | 4/2017 | Andreyev et al. |
| 9,686,395 B2 | 6/2017 | Erickson et al. |
| 9,725,754 B2 | 8/2017 | Boyle et al. |
| 9,752,182 B2 | 9/2017 | Collier et al. |
| 10,040,069 B2 | 8/2018 | Moore et al. |
| 10,173,182 B2 | 1/2019 | Tachibana et al. |
| 10,195,610 B2 | 2/2019 | Tang et al. |
| 10,603,664 B2 * | 3/2020 | Khattak ............ G01N 27/3271 |
| 2001/0055799 A1 | 12/2001 | Baunoch et al. |
| 2003/0027203 A1 | 2/2003 | Fields |
| 2003/0027244 A1 | 2/2003 | Colston et al. |
| 2004/0018502 A1 | 1/2004 | Makino et al. |
| 2004/0110141 A1 | 6/2004 | Pusey et al. |
| 2004/0209331 A1 | 10/2004 | Ririe |
| 2004/0224317 A1 | 11/2004 | Kordunsky et al. |
| 2004/0251426 A1 | 12/2004 | Birk et al. |
| 2005/0064598 A1 | 3/2005 | Yuan et al. |
| 2005/0100946 A1* | 5/2005 | Lipshutz ............ B01L 3/502715 435/6.12 |
| 2005/0194316 A1* | 9/2005 | Pourahmadi ...... B01L 3/502715 210/638 |
| 2005/0227275 A1 | 10/2005 | Jung et al. |
| 2006/0127924 A1* | 6/2006 | Hellyer .................. C12Q 1/689 435/6.12 |
| 2006/0160205 A1 | 7/2006 | Blackburn et al. |
| 2006/0177841 A1 | 8/2006 | Wangh et al. |
| 2006/0246493 A1 | 11/2006 | Jensen et al. |
| 2006/0258012 A1* | 11/2006 | Yang ..................... C12N 1/066 436/63 |
| 2007/0026391 A1 | 2/2007 | Stoughton et al. |
| 2007/0042427 A1 | 2/2007 | Gerdes et al. |
| 2007/0154922 A1 | 7/2007 | Collier et al. |
| 2007/0284360 A1 | 12/2007 | Santoruvo et al. |
| 2007/0292941 A1 | 12/2007 | Handique et al. |
| 2008/0026451 A1 | 1/2008 | Braman et al. |
| 2008/0038737 A1 | 2/2008 | Smith et al. |
| 2008/0050735 A1 | 2/2008 | Pushnova |
| 2008/0057572 A1 | 3/2008 | Petersen et al. |
| 2008/0113391 A1* | 5/2008 | Gibbons ............ B01L 3/502715 435/7.92 |
| 2008/0145852 A1 | 6/2008 | Shuber |
| 2008/0153078 A1 | 6/2008 | Braman et al. |
| 2008/0220468 A1 | 9/2008 | Windeyer et al. |
| 2008/0280285 A1 | 11/2008 | Chen et al. |
| 2009/0029422 A1 | 1/2009 | Hanafusa et al. |
| 2009/0042256 A1 | 2/2009 | Hanafusa et al. |
| 2009/0130745 A1 | 5/2009 | Williams et al. |
| 2009/0186344 A1 | 7/2009 | Farinas |
| 2009/0215072 A1 | 8/2009 | McDevitt et al. |
| 2009/0325276 A1 | 12/2009 | Battrell et al. |
| 2010/0003683 A1* | 1/2010 | Sarofim ............ B01L 3/502707 435/6.18 |
| 2010/0113762 A1 | 5/2010 | Ball et al. |
| 2010/0173393 A1 | 7/2010 | Handique et al. |
| 2010/0210038 A1 | 8/2010 | Blatt et al. |
| 2010/0291588 A1 | 11/2010 | McDevitt et al. |
| 2010/0297640 A1 | 11/2010 | Kumar et al. |
| 2011/0020876 A1 | 1/2011 | Wilding et al. |
| 2011/0039303 A1 | 2/2011 | Janovich et al. |
| 2011/0160090 A1 | 6/2011 | Cary |
| 2011/0203688 A1 | 8/2011 | Reed et al. |
| 2011/0211331 A1 | 9/2011 | Alkjaer et al. |
| 2011/0227551 A1 | 9/2011 | Black |
| 2011/0236960 A1* | 9/2011 | Bird ..................... B01F 11/0071 435/283.1 |
| 2011/0269191 A1 | 11/2011 | Belgrader et al. |
| 2011/0300545 A1 | 12/2011 | Cano et al. |
| 2011/0312793 A1 | 12/2011 | Azimi et al. |
| 2011/0312841 A1* | 12/2011 | Silverbrook .......... B01L 3/5027 506/40 |
| 2011/0313148 A1 | 12/2011 | Christ et al. |
| 2012/0021454 A1 | 1/2012 | Bikker et al. |
| 2012/0064534 A1 | 3/2012 | Pipper et al. |
| 2012/0070878 A1 | 3/2012 | Fink et al. |
| 2012/0088294 A1 | 4/2012 | Sun et al. |
| 2012/0115738 A1 | 5/2012 | Zhou et al. |
| 2012/0135511 A1 | 5/2012 | Battrell et al. |
| 2012/0141337 A1 | 6/2012 | Maltezos et al. |
| 2012/0264202 A1 | 10/2012 | Walker et al. |
| 2012/0282684 A1 | 11/2012 | Fritchie et al. |
| 2012/0288897 A1 | 11/2012 | Ching et al. |
| 2013/0040296 A1 | 2/2013 | Tulp et al. |
| 2013/0053255 A1 | 2/2013 | Vangbo et al. |
| 2013/0078736 A1 | 3/2013 | Grover et al. |
| 2013/0115712 A1 | 5/2013 | Yu et al. |
| 2013/0118900 A1 | 5/2013 | Reimitz et al. |
| 2013/0149710 A1 | 6/2013 | Yoon et al. |
| 2013/0171640 A1 | 7/2013 | Kwon et al. |
| 2013/0210080 A1 | 8/2013 | Rajagopal et al. |
| 2013/0217026 A1 | 8/2013 | Egan et al. |

(56) References Cited

U.S. PATENT DOCUMENTS

| | | | |
|---|---|---|---|
| 2013/0220781 A1 | 8/2013 | Czarnecki | |
| 2013/0225801 A1 | 8/2013 | Christoffel | |
| 2014/0045191 A1 | 2/2014 | DeJohn et al. | |
| 2014/0051159 A1 | 2/2014 | Bergstedt et al. | |
| 2014/0073013 A1* | 3/2014 | Gorman | B01L 7/52 |
| | | | 435/91.2 |
| 2014/0087359 A1 | 3/2014 | Njoroge et al. | |
| 2014/0098252 A1 | 4/2014 | Chang et al. | |
| 2014/0120539 A1 | 5/2014 | Tanner et al. | |
| 2014/0199685 A1 | 7/2014 | Lambotte et al. | |
| 2014/0274770 A1 | 9/2014 | Pack | |
| 2015/0031087 A1 | 1/2015 | Nagai et al. | |
| 2015/0176057 A1 | 6/2015 | Smith et al. | |
| 2015/0182966 A1 | 7/2015 | Coursey et al. | |
| 2015/0258273 A1 | 9/2015 | Payne et al. | |
| 2015/0346097 A1 | 12/2015 | Battrell et al. | |
| 2015/0361419 A1 | 12/2015 | Kim et al. | |
| 2016/0054316 A1 | 2/2016 | Egan et al. | |
| 2016/0222442 A1 | 8/2016 | Cary | |
| 2016/0310948 A1 | 10/2016 | Nowakowski et al. | |
| 2017/0021356 A1 | 1/2017 | Dority et al. | |
| 2017/0058324 A1 | 3/2017 | Balog et al. | |
| 2017/0152510 A1 | 6/2017 | Lorenz | |
| 2017/0173585 A1 | 6/2017 | Mahony et al. | |
| 2017/0203297 A1 | 7/2017 | Andreyev et al. | |
| 2017/0247745 A1 | 8/2017 | Shultz et al. | |
| 2017/0259263 A1 | 9/2017 | Andreyev et al. | |
| 2017/0304829 A1 | 10/2017 | Andreyev et al. | |
| 2018/0071734 A1 | 3/2018 | Andreyev et al. | |
| 2018/0117590 A1 | 5/2018 | Andreyev et al. | |
| 2018/0304260 A1 | 10/2018 | Thomas et al. | |
| 2019/0022643 A1 | 1/2019 | Andreyev et al. | |
| 2019/0030532 A1 | 1/2019 | Andreyev et al. | |
| 2019/0040451 A1 | 2/2019 | Mahony et al. | |
| 2019/0060895 A1 | 2/2019 | Myers, III et al. | |
| 2019/0083975 A1 | 3/2019 | Mitra et al. | |
| 2019/0094114 A1 | 3/2019 | Myers, III et al. | |
| 2019/0136226 A1 | 5/2019 | Swenson et al. | |
| 2019/0169677 A1 | 6/2019 | Andreyev et al. | |
| 2019/0193077 A1 | 6/2019 | Andreyev et al. | |
| 2019/0232283 A1 | 8/2019 | Andreyev et al. | |
| 2019/0232293 A1 | 8/2019 | Tang et al. | |
| 2020/0086234 A1* | 3/2020 | Elms | B04C 3/06 |
| 2020/0086324 A1* | 3/2020 | Swenson | C12Q 1/6844 |

FOREIGN PATENT DOCUMENTS

| | | |
|---|---|---|
| WO | WO2009/047804 A2 | 4/2009 |
| WO | WO2014/035986 A1 | 3/2014 |
| WO | WO2014/144548 A2 | 9/2014 |
| WO | WO2015/138343 A1 | 9/2015 |
| WO | WO2015/138648 A1 | 9/2015 |
| WO | WO2015/164770 A1 | 10/2015 |
| WO | WO2016/040523 A1 | 3/2016 |
| WO | WO2016/109691 A1 | 7/2016 |
| WO | WO2016/203019 A1 | 12/2016 |
| WO | WO2017/090043 A1 | 6/2017 |
| WO | WO2017/151195 | 9/2017 |
| WO | WO2017/160840 A1 | 9/2017 |
| WO | WO2017/197040 A1 | 11/2017 |
| WO | WO2008/149111 A1 | 1/2018 |
| WO | WO2018/005870 A1 | 1/2018 |

OTHER PUBLICATIONS

International Search Report and Written Opinion for International Application No. PCT/US2017/039844, dated Dec. 7, 2017.
International Search Report and Written Opinion for International Application No. PCT/US2017/32035, dated Oct. 4, 2017.
Extended European Search Report for European Application No. 15876276.5, dated Aug. 7, 2018.
BioFire Online Demo FilmArray. Http://filmarray.com/the-evidence/online-demo. 2014. 6 pages.
Hwang et al., "Black Printed Circuit Board-based Micro-Polymerase Chain Reaction Chip Structure for Fluorescence Detection Test", International Journal of Control and Automation (2015); vol. 8, No. 10: pp. 15-24 (10 pages).
Kopp et al., "Chemical Amplification: Continuous-Flow PCR on a Chip", Science (1998); 280 (5366): 1046-1048.
Schwerdt. Application of ferrofluid as a valve/pump for polycarbonate microfluidic devices. Johns Hopkins University. NSF Summer Undergraduate Fellowship in Sensor Technologies 2006, 17 pages.
Tanriverdi et al. A rapid and automated sample-to-result HIV load test for near-patient application. J Infect Dis., 201 Suppl 1:S52-S58, 2010.
Mohammed et al., Modeling of Serpentine Continuous Flow Polymerase Chain Reaction Microfluidics, IJEST, vol. 4, No. 3, pp. 1183-1189, Mar. 2012.
Lee et al. "A polymer lab-on-a-chip for reverse transcription (RT)-PCR baed point-of-care clinical diagnostics," The Royal Society of Chemistry, vol. 8, pp. 2121-2127, Oct. 31, 2008.
Gehring et al. "A High-Throughput, Precipitating Colorimetric Sandwich ELISA Microarray for Shiga Toxins," J. Toxins, vol. 6, p. 1855-72, Jun. 11, 2014.
Interbiotech, "Enzymatic substrates for ImmunoAssays," [retreived from the Internet Nov. 18, 2017: <http://www.interchim.fr/ft/B/BA357a.pdf>], 10 pages.
Kim, Yong Tae et al. "Integrated Microevidence of reverse transcription-polymerase chain reaction with colorimetric immunochromatographic detection for rapid gene expression analysis of invluenza A H1N1 virus," Biosensors and Bioelectronics, Elsevier Science Ltd UK, Amsterdam, NL V. 33 No. 1, pp. 88-94.
Kim, Jungkyu et al. "Automated microfluidic DNA/RNA extraction with both disposable and reusable components," Journal of Micromechanics and Microengineering, Vo. 22, No. 1, Dec. 20, 2011.
U.S. Appl. No. 14/984,573 First Action Interview Pilot Program Pre-Interview Communication dated Aug. 16, 2016.
International Search Report and Written Opinion for International Application No. PCT/US2010/060117, dated Apr. 12, 2019.
Petralia, Salvatore et al. "PCR Technologies for Point of Care Testing: Progress and Perspectives," ACS Sensors, 2017, 2 (7), pp. 876-891, Jul. 6, 2017.
Shafagati, et al., The Use of NanoTrap Particles as a Sample Enrichment Method to Enhance the Detection of Rift Valley Fever Virus. PLOS Neglected Tropical Diseases, Jul. 4, 2013; 7(7): e2296.
Extended European Search Report for European Application No. 17821297.3, dated Dec. 17, 2019.
Brunklaus, S. et al., Fast nucleic acid amplification for integration in point-of-care applications, Electrophoresis, 2012, vol. 33, pp. 3222-3228.
Choi, Gihoon et al., "A field-deployable mobile molecular diagnostic system for malaria at the point of need," Lab on a Chip, Royal Society of Chemistry, 2016, 16, 4341-4349.
Lee et al. "Single-channel multiplexing without melting curve analysis in real-time PCR," Scientific Reports, Dec. 11, 2014, vol. 4, Art. No. 7439, pp. 1-6, entire document.
Huang et al., "Efficient SNP Discovery by Combining Microarray and Lab-on-a-Chip Data for Animal Breeding and Selection," Microarrays, Nov. 16, 2015, vol. 4, No. 4, pp. 570-595, entire document.
Roskos, Kristina et al. "Simple System for Isothermal DNA Amplification Coupled to Lateral Flow Detection," PLoS ONE, vol. 8, No. 7, Jul. 26, 2013, p. e69355, XP055495626, DOI: 10.1371/journal.pone.0069355.
Herbst De Cortina, S. et al. "A Systematic Review of Point of Care Testing for Chlamydia trachomatis, Neisseria gonorrhoeae, and Trichomonas vaginalis," Infectious Diseases in Obstetrics and Gynecology, vol. 2016, 17 pages (Mar. 7, 2016).
Huppert, J. et al. "What's the Point? How Point-of-Care STI Tests can Impact Infected Patients," National Institutes of Health, vol. 9(1): pp. 36-46 (Mar. 1, 2010).

* cited by examiner

DEVICES AND METHODS FOR THE DETECTION OF MOLECULES USING A FLOW CELL

CROSS-REFERENCE TO RELATED APPLICATIONS

This application is a continuation of International Patent Application No. PCT/US2017/039844, filed Jun. 28, 2017, which claims benefit of priority to U.S. Provisional Application Ser. No. 62/356,464, entitled "Method for the Detection of Molecules Using a Flow Cell," filed Jun. 29, 2016, and 62/356,596, entitled "Molecular Diagnostic Device," filed Jun. 30, 2016, each of which is incorporated herein by reference in its entirety.

SEQUENCE LISTING

The instant application contains a Sequence Listing which has been filed electronically in ASCII format and is hereby incorporated by reference in its entirety. Said ASCII copy, created on Apr. 4, 2019, is named 1001-005-01US_SL.txt and is 845 bytes in size.

BACKGROUND

The embodiments described herein relate to devices and methods for molecular diagnostic testing. More particularly, the embodiments described herein relate to disposable, self-contained devices and methods for molecular diagnostic testing that include a detection module that produces a visual output.

There are over one billion infections in the U.S. each year, many of which are treated incorrectly due to inaccurate or delayed diagnostic results. Many known point of care (POC) tests have poor sensitivity (30-70%), while the more highly sensitive tests, such as those involving the specific detection of nucleic acids or molecular testing associated with a pathogenic target, are only available in laboratories. Thus, molecular diagnostics testing is often practiced in centralized laboratories. Known devices and methods for conducting laboratory-based molecular diagnostics testing, however, require trained personnel, regulated infrastructure, and expensive, high throughput instrumentation. Known high throughput laboratory equipment generally processes many (96 to 384 and more) samples at a time, therefore central lab testing is often done in batches. Known methods for processing test samples typically include processing all samples collected during a time period (e.g., a day) in one large run, resulting in a turn-around time of many hours to days after the sample is collected. Moreover, such known instrumentation and methods are designed to perform certain operations under the guidance of a skilled technician who adds reagents, oversees processing, and moves sample from step to step. Thus, although known laboratory tests and methods are very accurate, they often take considerable time, and are very expensive.

Although some known laboratory-based molecular diagnostics test methods and equipment offer flexibility (e.g., the ability to test for multiple different indications), such methods and equipment are not adaptable for point of care ("POC") use or in-home use by an untrained user. Specifically, such known devices and methods are complicated to use and include expensive and sophisticated components. Thus, the use of such known laboratory-based methods and devices in a decentralized setting (e.g., POC or in-home use) would likely result in an increase in misuse, leading to inaccurate results or safety concerns. For example, many known laboratory-based systems include sophisticated optics and laser light sources, which can present a safety hazard to an untrained user. Such known systems can also require the user to handle or be exposed to reagents, which can be a safety risk for an untrained user. Moreover, because of the flexibility offered by many known laboratory-based systems, such systems do not include lock-outs or mechanisms that prevent an untrained user from completing certain actions out of the proper sequence.

There are, however, some limited testing options available for testing done at the point of care ("POC"), or in other locations outside of a laboratory, including in-home use by an untrained user. Known POC or in-home testing options are often single analyte tests with low analytical quality. These tests are used alongside clinical algorithms to assist in diagnosis, but are frequently verified by higher quality, laboratory tests for the definitive diagnosis. Thus, in many instances, neither consumers nor physicians are enabled to achieve a rapid, accurate test result in time to "test and treat" in one visit. Thus, doctors and patients often determine a course of treatment before they know the diagnosis. This has tremendous ramifications: antibiotics are either not prescribed when needed, leading to infections; or antibiotics are prescribed when not needed, leading to new antibiotic-resistant strains in the community. Moreover, known systems and methods often result in diagnosis of severe viral infections, such as H1N1 swine flu, too late, limiting containment efforts. In addition, patients lose time in unnecessary, repeated doctor visits.

Although recent advances in technology have enabled the development of "lab on a chip" devices, such devices are often not optimized for point-of-care testing or in-home use. For example, some known devices and methods require an expensive or complicated instrument to interface with the test cartridge, thus increasing the likelihood of misuse. Moreover, many known "lab on a chip" devices amplify a very small volume of sample (e.g., less than one microliter), and are therefore not suited for analyzing for multiple different indications (e.g., a 3-plex or 4-plex test). Moreover, devices that produce such small sample volumes often include optical detection using photocells, charge coupled devices (CCD cameras) or the like, because the sample volumes are too small to produce an output that can be seen and interpreted by the naked eye.

Moreover, although some known POC or in-home test devices, such as test strips, can produce a visual indication, some known devices do not include a positive control (i.e., an indicator that is always "ON" during use that verifies proper use of the device) and/or a negative control (i.e., an indicator that is always "OFF" during use that verifies that there has not been any bleed into adjacent test areas). Moreover, some known methods or devices produce a visual indication that can fade or dissipate quickly, thus increasing likelihood of producing an inaccurate result.

Thus, a need exists for improved devices and methods for molecular diagnostic testing. In particular, a need exists for improved devices and methods having a detection module that produces an accurate visual output.

SUMMARY

Molecular diagnostic test devices for amplifying a nucleic acid within a sample and producing a visual indicator of a target amplicon in the sample are described herein. In some embodiments, a method includes conveying a detection solution containing the target amplicon into a detection module of a molecular diagnostic test device. The detection module includes a detection surface including a series of capture probes to which a first portion of the target amplicon is bound when the detection solution is conveyed. A first reagent formulated to produce a visible signal indicating a presence of the target amplicon is then conveyed into the detection module. The first reagent is bound to a second portion of the target amplicon when the first reagent is conveyed. A second reagent is conveyed into the detection module. The second reagent includes a precipitating substrate formulated to catalyze the production of the visible signal by producing an insoluble colored product when the second reagent is in contact with the first reagent. The method further includes viewing the visible signal via a transparent portion of the detection module.

In some embodiments, an apparatus includes a housing, a sample transfer manifold disposed at least partially within the housing, a sample input actuator, and a lid. The sample transfer manifold defines a fluid passage in fluid communication with a sample preparation module. The sample input actuator defines an inner surface. The inner surface and a surface of the sample transfer manifold collectively define a sample input volume configured to receive a biological sample. A top surface of the sample input actuator defines an opening into the sample input volume. The sample input actuator is configured to move relative to the sample transfer manifold from a first position to a second position to convey the biological sample from the sample input volume towards the sample preparation module via the fluid passage. The lid is coupled to the sample input actuator, and can move between a first lid position and a second lid position. The opening is exposed and a lock portion of the lid is engaged with a lock surface of the housing to retain the sample input actuator in the first position when the lid is in the first lid position. The lid is sealed about the opening and the lock portion of the lid is disengaged from the lock surface of the housing when the lid is in the second lid position.

DETAILED DESCRIPTION

Figure 1:
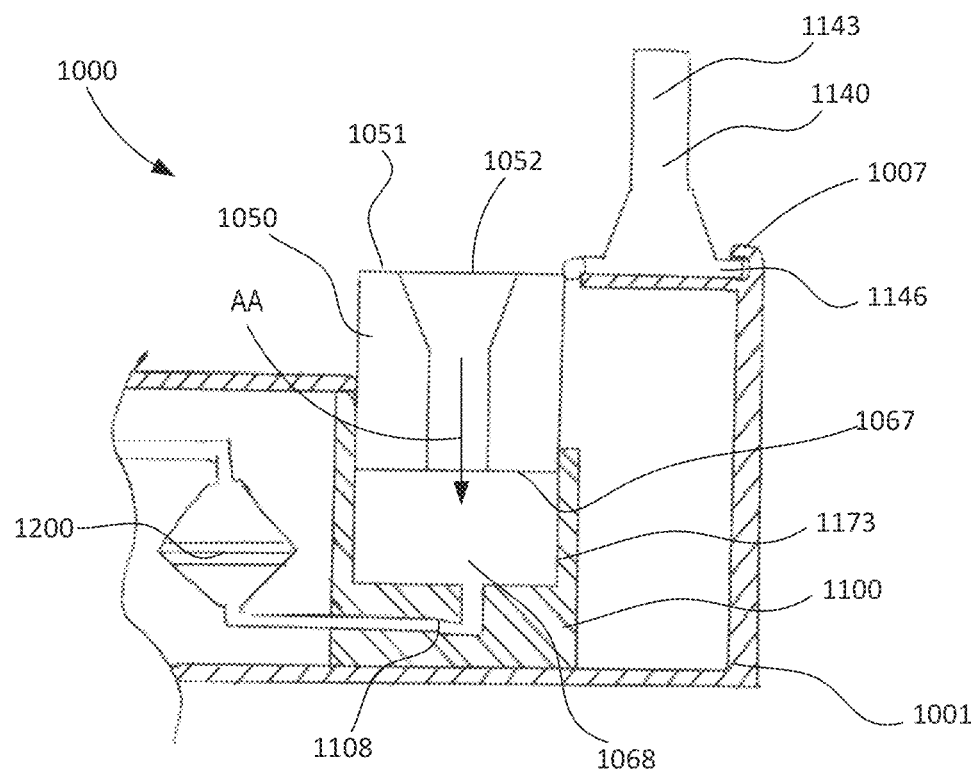
FIGS. 1-3 are cross-sectional schematic illustrations of a molecular diagnostic test device, according to an embodiment, in a first configuration, a second configuration, and a third configuration, respectively.

In some embodiments, an apparatus is configured for a disposable, portable, single-use, inexpensive, molecular diagnostic approach. The apparatus can include one or more modules configured to perform high quality molecular diagnostic tests, including, but not limited to, sample preparation, nucleic acid amplification (e.g., via polymerase chain reaction, isothermal amplification, or the like), and detection. In some embodiments, sample preparation can be performed by isolating the target pathogen/entity and removing unwanted amplification (e.g., PCR) inhibitors. The target entity can be subsequently lysed to release target nucleic acid for amplification. A target nucleic acid in the target entity can be amplified with a polymerase undergoing temperature cycling or via an isothermal incubation to yield a greater number of copies of the target nucleic acid sequence for detection.

In some embodiments, an apparatus includes a housing, a sample transfer manifold disposed at least partially within the housing, a sample input actuator, and a lid. The sample transfer manifold defines a fluid passage in fluid communication with a sample preparation module. The sample input actuator defines an inner surface. The inner surface and a surface of the sample transfer manifold collectively define a sample input volume configured to receive a biological sample. A top surface of the sample input actuator defines an opening into the sample input volume. The sample input actuator is configured to move relative to the sample transfer manifold from a first position to a second position to convey the biological sample from the sample input volume towards the sample preparation module via the fluid passage. The lid is coupled to the sample input actuator, and can move between a first lid position and a second lid position. The opening is exposed and a lock portion of the lid is engaged with a lock surface of the housing to retain the sample input actuator in the first position when the lid is in the first lid position. The lid is sealed about the opening and the lock portion of the lid is disengaged from the lock surface of the housing when the lid is in the second lid position.

In some embodiments, an apparatus includes a housing, a sample transfer manifold disposed at least partially within the housing, a sample preparation module disposed within the housing, a sample input actuator, a reagent actuator, and a reagent lock member. The sample transfer manifold has a surface defining at least a portion of a sample input volume configured to receive a biological sample. The sample preparation module is configured to extract a series of nucleic acid molecules from the biological sample. The sample input actuator has a top surface defining an opening into the sample input volume through which the biological sample can be conveyed. The sample input actuator is configured to move relative to the sample transfer manifold from a first position to a second position to convey the biological sample from the sample input volume to the sample preparation module. The reagent actuator is configured to move relative to the sample transfer manifold from a first reagent position to a second reagent position to convey a reagent within the sample transfer manifold into the sample preparation module. The reagent lock member is configured to engage a portion of the reagent actuator to limit movement of the reagent actuator from the first reagent position toward the second reagent position when the sample input actuator is in the first position.

In some embodiments, an apparatus includes a housing, an amplification module disposed within the housing, a reagent module disposed within the housing, and a detection module. The amplification module is configured to heat an input sample to amplify a nucleic acid within the input sample to produce a detection solution containing a target amplicon. The reagent module contains a first reagent and a second reagent. The detection module defines a detection channel in fluid communication with the amplification module and the reagent module. The detection module includes a detection surface within the detection channel. The detection surface includes a series of capture probes to which the target amplicon can be bound when the detection solutions flows across the detection surface at a first time. The first reagent is formulated to be bound the target amplicon when the first reagent flows across the detection surface at a second time. The first reagent is formulated to produce a visible signal indicating a presence of the target amplicon. The second reagent includes a precipitating substrate formulated to catalyze the production of the visible signal by producing an insoluble colored product when the second reagent is in contact with the first reagent.

In some embodiments, a method includes conveying a detection solution containing the target amplicon into a detection module of a molecular diagnostic test device. The detection module includes a detection surface including a series of capture probes to which a first portion of the target amplicon is bound when the detection solution is conveyed. A first reagent formulated to produce a visible signal indicating a presence of the target amplicon is then conveyed into the detection module. The first reagent is bound to a second portion of the target amplicon when the first reagent is conveyed. A second reagent is conveyed into the detection module. The second reagent includes a precipitating substrate formulated to catalyze the production of the visible signal by producing an insoluble colored product when the second reagent is in contact with the first reagent. The method further includes viewing the visible signal via a transparent portion of the detection module.

In some embodiments, a method includes conveying a biological sample into a sample input volume of a molecular diagnostic test device. The device is then actuated to cause the device to perform a series of operations. The operations include conveying the biological sample from the sample input volume to an amplification module within the molecular diagnostic test device. The operations include heating a portion of the amplification module to amplify a nucleic acid extracted from the biological sample to produce a detection solution containing a target amplicon. The operations include conveying the detection solution through a detection channel defined at least in part by a detection surface, the detection surface including a series of capture probes to which a first portion of the target amplicon is bound. The operations include conveying through the detection channel a first reagent formulated to produce a visible signal indicating a presence of the target amplicon. The first reagent is bound to a second portion of the target amplicon when conveyed through the detection channel. The operations include conveying through the detection channel a second reagent formulated to catalyze the production of the visible signal when the second reagent is in contact with the first reagent. The method further includes viewing the visible signal via a transparent member covering the detection channel.

In some embodiments, a method includes conveying a biological sample into a sample input volume defined at least in part by a sample transfer manifold of a molecular diagnostic test device. The biological sample is conveyed into the sample volume via an opening defined by a sample input actuator. A lid is moved, after the biological sample is in the sample input volume, relative to the sample input actuator from a first lid position to a second lid position. A lock portion of the lid is engaged with a lock surface of the molecular diagnostic test device to retain the sample input actuator in a first position when the lid is in the first lid position. The lid covers the opening, and the lock portion of the lid is disengaged from the lock surface of the molecular diagnostic test device when the lid is in the second lid position. The sample input actuator is then moved from the first position to the second position to convey the biological sample from the sample input volume towards the sample preparation module via a fluid passage defined by the sample transfer manifold.

In some embodiments, an amplification module can be included within a diagnostic device that is optimized for disposable and portable operation. For example, in some embodiments, an apparatus includes a power module operated by a small battery (e.g., a 9V battery). In such embodiments, the device can include a controller to control the timing and/or magnitude of power draw to accommodate the capacity of the battery.

In some embodiments, a sample preparation module, an amplification module, and/or a detection module can be included within a diagnostic device that is optimized for one-time use. In some embodiments, the diagnostic device is disposable via standard waste procedures after use.

As used herein, the term "about" when used in connection with a referenced numeric indication means the referenced numeric indication plus or minus up to 10% of that referenced numeric indication. For example, the language "about 50" covers the range of 45 to 55.

As used in this specification and the appended claims, the words "proximal" and "distal" refer to direction closer to and away from, respectively, an operator of the diagnostic device. Thus, for example, the end of an actuator depressed by a user that is furthest away from the user would be the distal end of the actuator, while the end opposite the distal end (i.e., the end manipulated by the user) would be the proximal end of the actuator.

The term "fluid-tight" is understood to encompass hermetic sealing (i.e., a seal that is gas-impervious) as well as a seal that is only liquid-impervious. The term "substantially" when used in connection with "fluid-tight," "gas-impervious," and/or "liquid-impervious" is intended to convey that, while total fluid imperviousness is desirable, some minimal leakage due to manufacturing tolerances, or other practical considerations (such as, for example, the pressure applied to the seal and/or within the fluid), can occur even in a "substantially fluid-tight" seal. Thus, a "substantially fluid-tight" seal includes a seal that prevents the passage of a fluid (including gases, liquids and/or slurries) therethrough when the seal is maintained at pressures of less than about 5 psig. Any residual fluid layer that may be present on a portion of a wall of a container after component defining a "substantially-fluid tight" seal are moved past the portion of the wall are not considered as leakage.

The term "parallel" is used herein to describe a relationship between two geometric constructions (e.g., two lines, two planes, a line and a plane, or the like) in which the two geometric constructions are non-intersecting as they extend substantially to infinity. For example, as used herein, a planar surface (i.e., a two-dimensional surface) is said to be parallel to a line when every point along the line is spaced apart from the nearest portion of the surface by a substantially equal distance. Similarly, a first line (or axis) is said to be parallel to a second line (or axis) when the first line and the second line do not intersect as they extend to infinity. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

The terms "perpendicular," "orthogonal," and "normal" are used herein to describe a relationship between two geometric constructions (e.g., two lines, two planes, a line and a plane, or the like) in which the two geometric constructions intersect at an angle of approximately 90 degrees within at least one plane. For example, as used herein, a line (or axis) is said to be normal to a planar surface when the line and a portion of the planar surface intersect at an angle of approximately 90 degrees within the planar surface. Two geometric constructions are described herein as being, for example, "perpendicular" or "substantially perpendicular" to each other when they are nominally perpendicular to each other, such as for example, when they are perpendicular to each other within a tolerance. Such tolerances can include, for example, manufacturing tolerances, measurement tolerances or the like.

Similarly, geometric terms, such as "parallel," "perpendicular," "cylindrical," "square," "conical," or "frusto-conical" are not intended to require absolute mathematical precision, unless the context indicates otherwise. Instead, such geometric terms allow for variations due to manufacturing or equivalent functions. For example, if an element is described as "conical" or "generally conical," a component that is not precisely conical (e.g., one that is slightly oblong) is still encompassed by this description.

As used in this specification and the appended claims, the term "reagent" includes any substance that is used in connection with any of the reactions described herein. For example, a reagent can include an elution buffer, a PCR reagent, an enzyme, a substrate, a wash solution, or the like. A reagent can include a mixture of one or more constituents. A reagent can include such constituents regardless of their state of matter (e.g., solid, liquid or gas). Moreover, a reagent can include the multiple constituents that can be included in a substance in a mixed state, in an unmixed state and/or in a partially mixed state. A reagent can include both active constituents and inert constituents. Accordingly, as used herein, a reagent can include non-active and/or inert constituents such as, water, colorant or the like.

The term "nucleic acid molecule," "nucleic acid," or "polynucleotide" may be used interchangeably herein, and may refer to deoxyribonucleic acid (DNA) or ribonucleic acid (RNA), including known analogs or a combination thereof unless otherwise indicated. Nucleic acid molecules to be profiled herein can be obtained from any source of nucleic acid. The nucleic acid molecule can be single-stranded or double-stranded. In some cases, the nucleic acid molecules are DNA The DNA can be mitochondrial DNA, complementary DNA (cDNA), or genomic DNA. In some cases, the nucleic acid molecules are genomic DNA (gDNA). The DNA can be plasmid DNA, cosmid DNA, bacterial artificial chromosome (BAC), or yeast artificial chromosome (YAC). The DNA can be derived from one or more chromosomes. For example, if the DNA is from a human, the DNA can be derived from one or more of chromosomes 1, 2, 3, 4, 5, 6, 7, 8, 9, 10, 11, 12, 13, 14, 15, 16, 17, 18, 19, 20, 21, 22, X, or Y. In some cases, the nucleic acid molecules are RNA can include, but is not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA, or ncRNA can include snoR-NAs, microRNAs, siRNAs, piRNAs and long nc RNAs. The source of nucleic acid for use in the devices, methods, and compositions described herein can be a sample comprising the nucleic acid.

Unless indicated otherwise, the terms apparatus, diagnostic apparatus, diagnostic system, diagnostic test, diagnostic test system, test unit, and variants thereof, can be interchangeably used.

Figure 2:
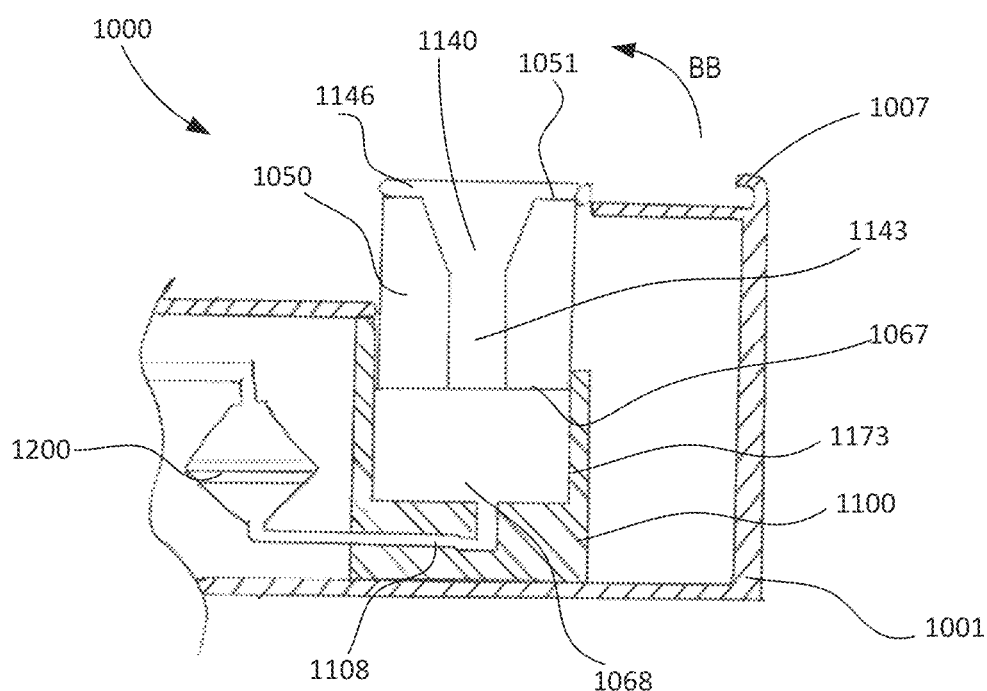
Figure 3:
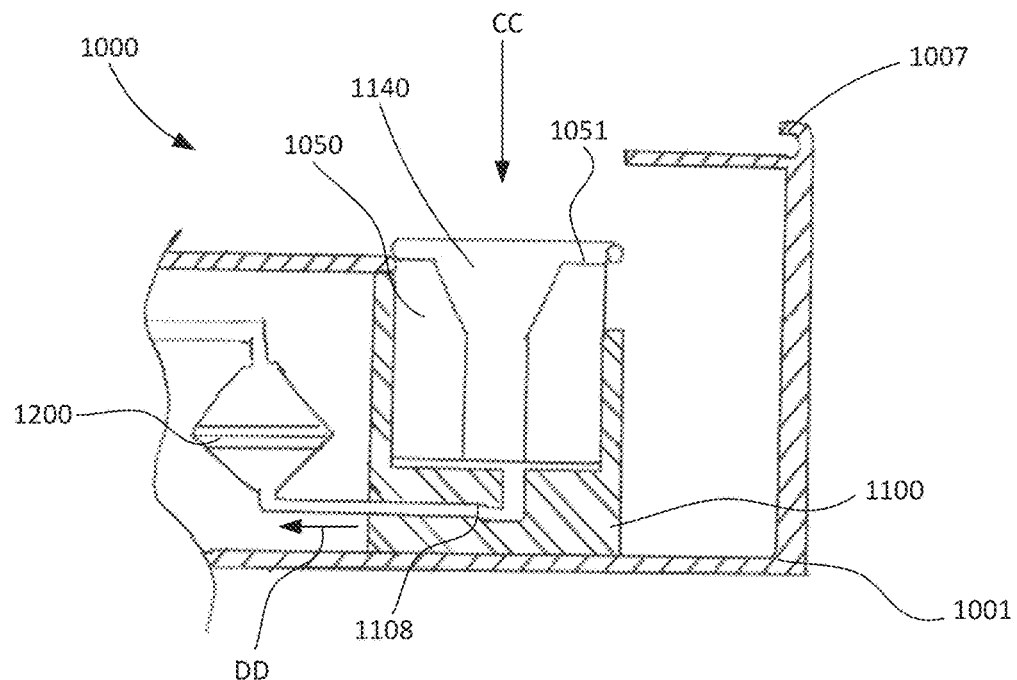

FIGS. 1-3 are schematic illustrations of a portion of a molecular diagnostic test device 1000 (also referred to as a "test device" or "device"), according to an embodiment. The test device 1000 is configured to manipulate an input sample to produce one or more output signals associated with a target cell, according to any of the methods described herein. In some embodiments, the test device 1000 can be an integrated device that is suitable for use within a point-of-care setting (e.g., doctor's office, pharmacy or the like), decentralized test facility, or at the user's home. Similarly stated, in some embodiments, the modules of the device, described below, are contained within a single housing such that the test device can be fully operated without any additional instrument, docking station, or the like. Further, in some embodiments, the device 1000 can have a size, shape and/or weight such that the device 1000 can be carried, held, used and/or manipulated in a user's hands (i.e., it can be a "handheld" device). In some embodiments, the test device 1000 can be a self-contained, single-use device.

In some embodiments, the device 1000 (and any of the devices shown and described herein) can be a CLIA-waived device and/or can operate in accordance with methods that are CLIA waived. Similarly stated, in some embodiments, the device 1000 (and any of the other devices shown and described herein) is configured to be operated in a sufficiently simple manner, and can produce results with sufficient accuracy to pose a limited likelihood of misuse and/or to pose a limited risk of harm if used improperly. In some embodiments, the device 1000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 1000 can be configured for long term storage in a manner that poses a limited likelihood of misuse (spoilage of the reagent(s), expiration of the reagents(s), leakage of the reagent(s), or the like). In some embodiments, the molecular diagnostic test device 1000 is configured to be stored for up to about 36 months, up to about 32 months, up to about 26 months, up to about 24 months, up to about 20 months, up to about 18 months, or any values there between.

The test device 1000 includes at least a housing 1001, a sample transfer manifold 1100, a sample input actuator 1050, and a lid 1140. In some embodiments, the test device 1000 can include any other components or modules described herein, such as, for example an amplification module (e.g., the amplification module 2600 or 4600) or a detection module (e.g., the detection module 2800 or 4800). The housing 1001 can be any structure within which the sample transfer manifold 1100 or other components are contained (or partially contained) to form an integrated device for sample preparation and/or molecular testing. The housing 1001 includes a lock surface 1007 that engages and/or interfaces with the lid 1140, as described below, to reduce the likelihood that the test device 1000 will be actuated in an incorrect manner or sequence. The housing 1001 can be a monolithically constructed housing or can include multiple separately constructed members that are later joined together to form the housing 1001.

The sample transfer manifold 1100 is within the housing 1001, and defines a fluid passage 1108 in fluid communication with a sample preparation module 1200. The sample transfer manifold 1100 includes a surface 1173 (also referred to as an inner surface) that, as described below, along with a surface 1067 of the sample input actuator 1050 forms a portion of a boundary of a sample input volume 1068. In this manner, the sample transfer manifold 1100 functions both to receive a biological sample (i.e., within the sample input volume 1068), and also to provide the passage 1108 through which the biological sample can be conveyed to the sample preparation module 1200. Although the surface 1173 is shown and described as being an inner surface (i.e., forming a portion of the sample input volume 1068 within which the sample input actuator 1050 is movably disposed), in other embodiments, the surface 1173 can be an outer surface or can otherwise be disposed within the sample input actuator 1050.

The sample preparation module 1200 can include any suitable components to manipulate the sample for further diagnostic testing. For example, in some embodiments, the sample preparation module 1200 can extract nucleic acid molecules from the biological sample. The sample preparation module 1200 can include any of the components described herein, such as, for example, a filter assembly (e.g., the filter assembly 4230, a lysing assembly and/or an inactivation chamber (see, e.g., the lysing module 4300).

The sample transfer manifold 1100 can include any structure, components, or reagents to facilitate any of the sample input operations and/or the sample preparation operations described herein. For example, in some embodiments, one or more reagents can be included within the sample transfer manifold 1100 (e.g., within the sample input volume 1068, the passage 1108, or any other portion or volume defined by the sample transfer manifold). Such reagents can include, for example, a wash buffer, a positive control organism, an elution buffer, or the like. In some embodiments, the sample transfer manifold 1100 can include one or more flow control mechanisms, such as, for example, check valves, filters, seals, or the like. Although shown as being disposed fully within the housing 1001, in other embodiments, the sample transfer manifold 1100 and/or the sample preparation module 1200 can be only partially disposed within the housing 1001. Said another way, in some embodiments, the sample transfer manifold 1100 and/or the sample preparation module 1200 can be only partially enclosed, surrounded, or encompassed by the housing 1001.

The sample input actuator 1050 includes a first (or top) surface 1051 and a second (or inner) surface 1067. As described above, the second surface 1067 and the surface 1173 of the sample transfer manifold 1100 form a boundary of (i.e., collectively define) the sample input volume 1068. The first surface 1051 of the sample input actuator 1050 defines an opening 1052 into the sample input volume 1068. This arrangement allows the biological sample (not shown) to be conveyed into the sample input volume 1068 via the opening 1052. The sample input actuator 1050 is movably coupled to or is otherwise configured to move relative to the sample transfer manifold 1100. In particular, the sample input actuator 1050 can move from a first position (FIGS. 1 and 2) to a second position (FIG. 3) to convey the biological sample from the sample input volume 1068 towards the sample preparation module 1200 via the fluid passage 1108. In this manner, the sample input actuator 1050 functions both to receive a biological sample (i.e., within the sample input volume 1068), and also to produce a motive force to convey the biological sample through the passage 1108 towards the sample preparation module 1200.

The sample input actuator 1050 can include any structure, components, or reagents to facilitate any of the sample input operations and/or the sample preparation operations described herein. For example, in some embodiments, one or more reagents can be included within the sample input actuator 1050 (e.g., within the sample input volume 1068, the passage from the opening 1052 to the sample input volume 1068, or any other portion or volume defined by the sample input actuator). Such reagents can include, for example, a wash buffer, a positive control organism, an elution buffer, or the like. In some embodiments, the sample input actuator 1050 can include one or more flow control mechanisms, such as, for example, check valves, filters, seals, or the like.

The lid 1140 is coupled to the sample input actuator 1050, and can move between a first lid position (FIG. 1) and a second lid position (FIGS. 2 and 3). The lid 1140 includes a lock portion 1146 and a seal portion 1143. As shown in FIG. 1, the lock portion 1146 is engaged with the lock surface 1007 of the housing 1001 to retain the lid in its first lid position and to retain the sample input actuator 1050 in its first position. Specifically, because the lid 1140 is retained by the lock surface 1007 of the housing 1001, movement of the sample input actuator 1050 relative to the housing 1001 (and hence the sample transfer manifold 1100) is limited. Thus, when the lid 1140 is in its first lid position, it functions as a "lock" to prevent the sample input actuator 1050 from being moved. Moreover, when the lid 1140 is in its first lid position, the opening 1052 is exposed, thus providing a user with convenient access to convey the biological sample into the sample input volume 1068. This arrangement limits the likelihood of misuse of the test device. For example, this arrangement prevents a user from inadvertently depressing the sample input actuator 1050 while the lid 1140 is opened (i.e., in its first position). The lock portion 1146 of the lid 1140 and the lock surface 1007 of the housing 1001 can include any suitable mechanisms to releasably lock the lid 1140 to the housing 1001 as described herein. For example, in some embodiments, the lock portion 1146 and/or the lock surface 1007 can include mating grooves, protrusions, rails, fasteners, or the like.

Referring to FIG. 2, when the lid is in its second lid position (i.e., the closed position), the seal portion 1143 forms a seal about the opening 1052. Additionally, the lock portion 1146 of the lid 1140 is disengaged from the lock surface 1007 of the housing 1001. This arrangement allows the biological sample to be safely sealed within the sample input volume 1068 for further processing. The seal portion 1143 can include an elastomeric seal, such as an O-ring or the like, and can produce a substantially fluid-tight seal to protect against spilling or leaking during the test. The seal portion 1143 also fluidically isolates the sample input volume 1068 such that the pressure generated therein can be maintained to convey the biological sample through the passage 1108 (rather than leaking out via the opening 1052).

The test device 1000 can be used to manipulate, process, or prepare a biological sample as a part of any of the methods of diagnostic testing described herein. The test device 1000 is initially shipped or presented to the user with the sample input actuator 1050 in its first position and the lid 1140 in the first lid position, as shown in FIG. 1. Upon unwrapping or otherwise opening the test device 1000, the user can the convey a biological sample (not shown) into the sample input volume 1068 via the opening 1052 of the sample input actuator 1050, as shown by the arrow AA in FIG. 1. The biological sample can be any suitable sample, such as, for example, blood, urine, male urethral specimens, vaginal specimens, cervical swab specimens, nasal swab specimens, or any other biological samples described herein. Thus, in some embodiments, the biological sample input can be a "raw" (or unprocessed) sample.

After the biological sample is within the sample input volume 1068, the lid 1140 can be moved from its first (or open) lid position (FIG. 1) to its second (or closed) lid position (FIG. 2), as shown by the arrow BB in FIG. 2. In this manner, the sample input actuator 1050 can be unlocked to allow actuation of the test device 1000. Moreover, when the lid 1140 is in its second lid position (i.e., the closed position), the seal portion 1143 forms a seal about the opening 1052. Although the seal portion 1143 is shown as extending into the sample input actuator 1050 (for example, to limit the dead volume that may be present in the opening 1052, in other embodiments, the seal portion 1143 need only cover and seal the opening 1052. Although the lid 1140 is shown as rotating to move from the first lid position to the second lid position, in other embodiments, the lid 1140 (or any of the lids shown herein) can move in any suitable manner (i.e., rotation, translation, or both rotation and translation) between the first lid position and the second lid position.

After the lid 1140 is closed (i.e. in the second lid position), the sample input actuator 1050 can be moved from its first position to its second position, as shown by the arrow CC in FIG. 3. In this manner, the test device 1000 and/or the sample preparation module 1200 can be actuated. Specifically, as described above, when the sample input actuator 1050 is moved relative to the sample transfer manifold 1100, the biological sample is conveyed from the sample input volume 1068 towards the sample preparation module 1200 via the fluid passage 1108, as shown by the arrow DD in FIG. 3. As shown, movement of the sample input actuator 1050 reduces the volume of the sample input volume 1068, thereby pressurizing the biological sample therein, which, in turn, pushes the biological sample through the passage 1108. Said another way, the sample input actuator 1050 functions as a piston pump to convey the biological sample towards the sample preparation module. In some embodiments, the sample transfer manifold 1100 or the sample input actuator 1050 includes a seal (e.g., an O-ring, or the like) to seal the interface between the surface 1067 and the surface 1173 (i.e., to fluidically isolate the sample input volume 1068) from an external volume.

In some embodiments, the sample input actuator 1050 is manually moved (i.e., is moved by direct human interaction and not by a motorized actuator). In this manner, the force or pressure applied to the biological sample originates directly from the user's actuation of the sample input actuator.

In some embodiments, the lid 1140 (and any of the lids shown and described herein) can include a second lock portion or lock member (not shown) that engages or contacts a portion of the housing 1001 or the sample input actuator 1050 to limit or prevent movement of the lid 1140 from the second (closed) lid position back toward the first (or opened) lid position. In such embodiments, the lid 1140 is irreversibly locked in its second position. In this manner, the user cannot add to or otherwise disrupt a sample after the lid has been closed. This arrangement can reduce the likelihood of misuse of the device 1000.

In some embodiments, the sample input actuator 1050 (and any of the actuators shown and described herein) can include a lock portion or lock member (not shown) that engages a corresponding lock surface (not shown) of the housing 1001 and/or the sample transfer manifold 1100 to prevent movement of the sample input actuator 1050 from the second position back towards the first position. In such embodiments, the sample input actuator 1050 is irreversibly locked in its second position, thereby preventing the user from trying to pump or press the actuator several times. This arrangement can reduce the likelihood of misuse of the device 1000.

Although the test device 1000 is shown as including only a sample input actuator 1050, in other embodiments, the test device 1000 (and any of the device shown and described herein) can include one or more reagent actuators (not shown in FIGS. 1-3). Such reagent actuators can, for example, actuate a wash module (e.g., similar to the wash module 4210), an elution module (e.g., similar to the elution module 4260), or one or more reagent containers that include detection reagent. In some such embodiments, the reagent actuator can be operably coupled to the sample input actuator such that the actuators cannot be moved in an improper sequence. For example, in some embodiments, the sample input actuator 1050 (and any of the sample input actuator described herein) can include a lock actuator that contacts, moves, or otherwise engages a reagent lock member (not shown) to release the reagent actuator for movement.

In other embodiments, a device can include a lid that performs similar functions as the lid 1140 and the actuator 1050. Said another way, in some embodiments, a device can include a lid that functions to seal a sample input volume and also actuate the device. For example, in some embodiments, the movement of a lid can both seal the sample input volume (e.g., to prevent leakage) and also to pressurize the sample input volume to convey the sample towards the remainder of the device. In this manner, the operation of the device can be instigated with only single motion (i.e., the closing of the lid).

The molecular diagnostic test device 1000 (and any of the molecular diagnostic test devices described herein) can include any suitable components to amplify the desired target and/or produce a signal that can be easily read. For example, in some embodiments, any of the molecular diagnostic test devices described herein can include a detection module that produces a colorimetric output that indicates a presence of a target organism in the biological sample. Such devices can produce a colorimetric output that is easily viewed by the user (i.e., can be of sufficient size and color properties) to be seen by the user without external aids (e.g., a magnifying glass, camera, or the like). Moreover, such devices can produce a colorimetric output that is stable and persists for a sufficient period of time (e.g., at least one hour, at least two hours, at least three hours, at least 12 hours, at least 24 hours, and at least 48 hours) so that the user can easily interpret the results, even if there is an interruption before the results are viewed. Such devices can be configured to produce a colorimetric output that does not wash away or drift if the device is moved during the course of normal use. In this manner, the device can be operated by a user with minimal (or no) scientific training, in accordance with methods that require little judgment of the user, and/or in which certain operational steps are easily and/or automatically controlled.

Figure 4:
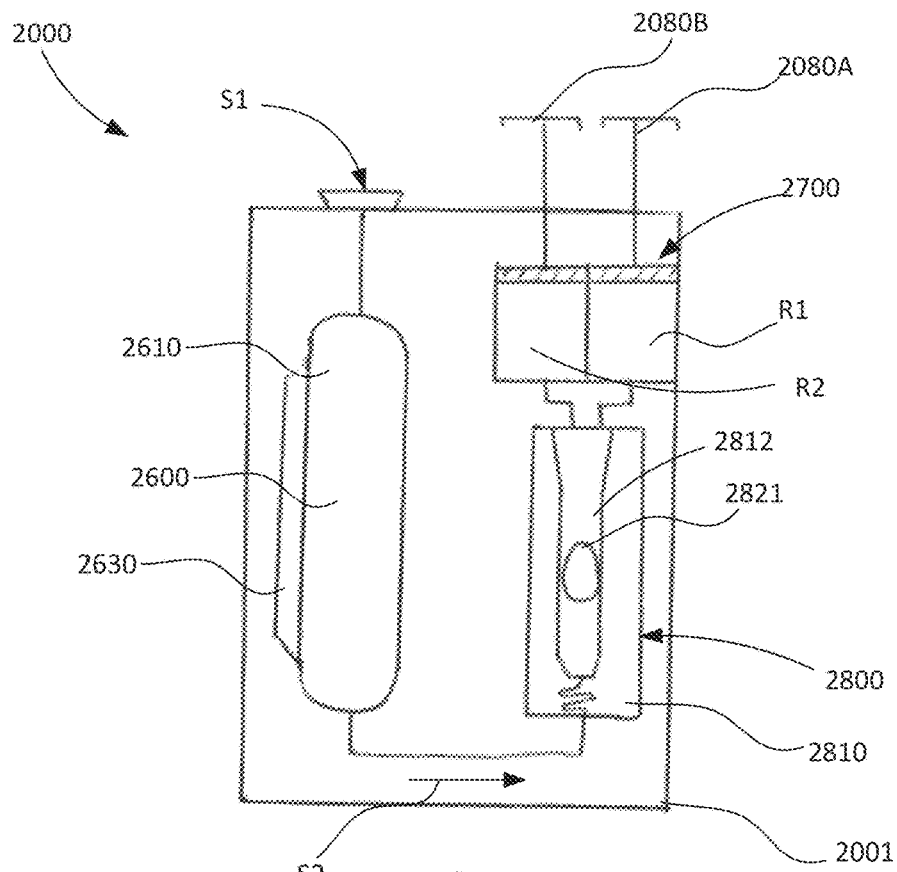
FIGS. 4 and 5 are schematic illustrations of a molecular diagnostic test device, according to an embodiment, in a first configuration and a second configuration, respectively.
Figure 5:
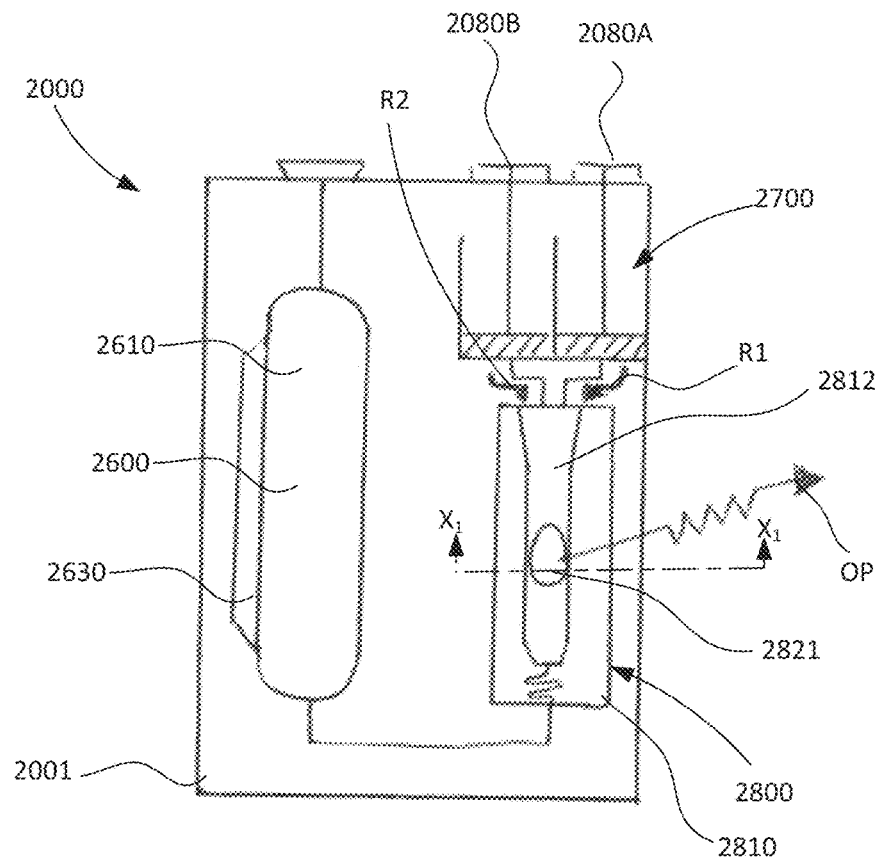
Figure 6:
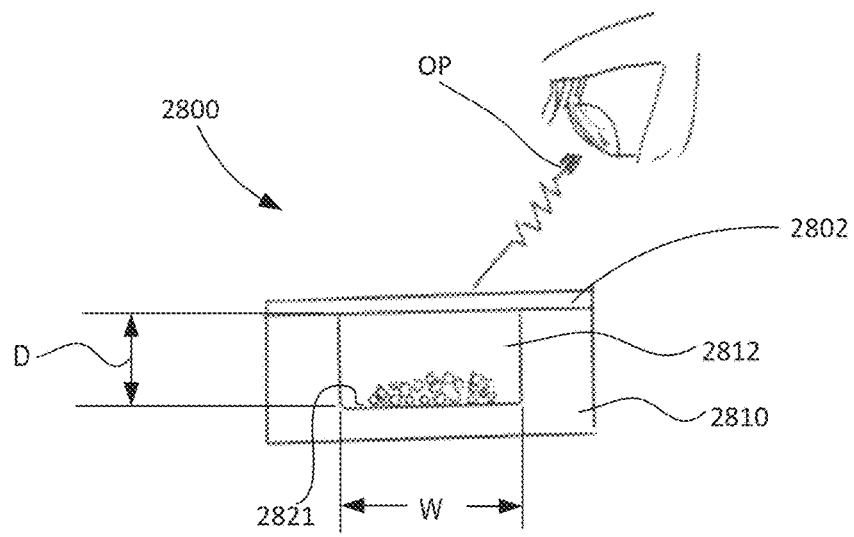
FIG. 6 is a cross-sectional view of a portion of the molecular diagnostic test device shown in FIGS. 4 and 5 taken along line X-X in FIG. 5.

As an example, FIGS. 4-6 are schematic illustrations of a portion of a molecular diagnostic test device 2000 (also referred to as a "test device" or "device"), according to an embodiment. The test device 2000 is configured to manipulate an input sample to produce one or more output signals (e.g., see output signal OP) associated with a target cell, according to any of the methods described herein. In some embodiments, the test device 2000 can be an integrated device that is suitable for use within a point-of-care setting (e.g., doctor's office, pharmacy or the like), decentralized test facility, or at the user's home. Similarly stated, in some embodiments, the modules of the device, described below, are contained within a single housing such that the test device can be fully operated without any additional instrument, docking station, or the like. Further, in some embodiments, the device 2000 can have a size, shape and/or weight such that the device 2000 can be carried, held, used and/or manipulated in a user's hands (i.e., it can be a "handheld" device). In some embodiments, the test device 2000 can be a self-contained, single-use device.

In some embodiments, the device 2000 (and any of the devices shown and described herein) can be a CLIA-waived device and/or can operate in accordance with methods that are CLIA waived. Similarly stated, in some embodiments, the device 2000 (and any of the other devices shown and described herein) is configured to be operated in a sufficiently simple manner, and can produce results with sufficient accuracy to pose a limited likelihood of misuse and/or to pose a limited risk of harm if used improperly. In some embodiments, the device 2000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 2000 can be configured for long term storage in a manner that poses a limited likelihood of misuse (spoilage of the reagent(s), expiration of the reagents(s), leakage of the reagent(s), or the like). In some embodiments, the molecular diagnostic test device 2000 is configured to be stored for up to about 36 months, up to about 32 months, up to about 26 months, up to about 24 months, up to about 20 months, up to about 18 months, or any values there between The test device 2000 includes a housing 2001, an amplification module 2600, a reagent module 2700, and a detection module 2800. In some embodiments, the test device 2000 can include any other components or modules described herein, such as, for example a sample input module or a sample preparation module. The housing 2001 can be any structure within which the amplification module 2600, the reagent module 2700, and the detection module 2800 are contained (or partially contained) to form an integrated device for sample preparation and/or molecular testing. In some embodiments, the housing 1001 can define an opening or include a transparent portion through which the detection module can be viewed. In some embodiments, the housing 2001 can include one or more lock surfaces or lock members (not shown) that engage and/or interface with various actuators to reduce the likelihood that the test device 2000 will be actuated in an incorrect manner or sequence. The housing 2001 can be a monolithically constructed housing or can include multiple separately constructed members that are later joined together to form the housing 2001.

The amplification module 2600 includes a flow member 2610 and a heater 2630. The flow member (also referred to as a reaction volume) 2610 can be any suitable flow member that defines a volume or a series of volumes within which the input biological sample S1 (or a solution containing extracted nucleic acid from the sample 51) can flow and/or be maintained to amplify the target nucleic acid molecules therein to produce an output detection solution S2 that contains a target amplicon to be detected. The heater 2630 can be any suitable heater or group of heaters coupled to the flow member 2610 that can heat the input biological sample S1 within the flow member 2610 to perform any of the amplification operations as described herein. For example, in some embodiments, the amplification module 2600 (or any of the amplification modules described herein) can be similar to the amplification modules shown and described in U.S. patent application Ser. No. 15/494,145, entitled "Printed Circuit Board Heater for an Amplification Module," which is incorporated herein by reference in its entirety. In other embodiments, the amplification module 2600 (or any of the amplification modules described herein) can be similar to the amplification modules shown and described in International Patent Publication No. WO2016/109691, entitled "Devices and Methods for Molecular Diagnostic Testing," which is incorporated herein by reference in its entirety.

In some embodiments, the flow member 2610 defines a single volume within which the input biological sample S1 (or extracted nucleic acid) is maintained and heated to amplify the nucleic acid molecules thereby producing the detection solution S2. In other embodiments, the flow member 2610 can define a "switchback" or serpentine flow path through which the input biological sample S1 (or extracted nucleic acid) flows. Similarly stated, in some embodiments, the flow member 2610 defines a flow path that is curved such that the flow path intersects the heater 2630 at multiple locations. In this manner, the amplification module 2600 can perform a "flow through" amplification reaction where the input biological sample S1 flows through multiple different temperature regions.

The heater 2630 can be any suitable heater or collection of heaters that can perform the functions described herein to amplify the prepared solution. In some embodiments, the heater 2630 can establish multiple temperature zones through which the prepared solution flows and/or can define a desired number of amplification cycles to ensure the desired test sensitivity (e.g., at least 30 cycles, at least 34 cycles, at least 36 cycles, at least 38 cycles, or at least 40 cycles). The heater 2630 (and any of the heaters described herein) can be of any suitable design. For example, in some embodiments, the heater 2630 can be a resistance heater, a thermoelectric device (e.g. a Peltier device), or the like. In some embodiments, the heater 2630 can be one or more linear "strip heaters" arranged such that the flow path crosses the heaters at multiple different points. In other embodiments, the heater 2630 can be one or more curved heaters having a geometry that corresponds to that of the flow member 2610 to produce multiple different temperature zones in the flow path.

Although the amplification module 2600 is generally described as performing a thermal cycling operation on the input biological sample S1, in other embodiment, the amplification module 2600 (and any of the amplification modules described herein) can perform any suitable thermal reaction to amplify nucleic acids within the solution. In some embodiments, the amplification module 2600 (and any of the amplification modules described herein) can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process.

The reagent module 2700 is disposed within the housing 2001, and defines a reagent volume within which at least a first reagent R1 and a second reagent R2 are contained. The reagent module also includes a first reagent actuator 2080A and second reagent actuator 2080B. As described below, the reagent module 2700 is in fluid communication with the detection module 2800 allowing the first reagent R1 and the second reagent R2 to be conveyed into the detection module 2800. The first reagent R1 and the second reagent R2 can be formulated to perform an assay (e.g., an enzyme-linked immunoassay) that produces a colorimetric output to detect the target amplicon within the detection solution S2. Specifically, the first reagent R1 is formulated to produce a visible signal OP indicating a presence of the target amplicon. The first reagent R1 can include, for example, a binding moiety and any suitable enzyme such as horseradish peroxidase (HRP) or alkaline phosphates. In some embodiments, the HRP enzyme already conjugated to a streptavidin molecule. The streptavidin component binds to the biotin portion of the target amplicon and the HRP component produces a color change when exposed to a substrate (e.g., the second reagent R2).

The second reagent R2 includes a substrate formulated to catalyze the production of the visible signal OP. The second reagent R2 can include, for example, any of tetramethylbenzidine (TMB), 3-ethylbenzothiazoline-6-sulfonic acid, o-phenylenediamine, Amplex Red, homovanillic acid, 3,3'-diaminobenzidine, 3-amino-9-ethylcarbazole, 5-Bromo-4-chloro-3-indolyl phosphate, 5-Bromo-4-chloro-3-indolyl phosphate/nitro blue tetrazolium, Fast Red (Sigma). In some embodiments, the substrate is TMB. In such embodiments, TMB in the detection module 2800 changes color from colorless to blue, and finally yellow above any positive chambers. The yellow color is produced when the detection module 2800 is heated to about 40° C. during the detection operation. In contrast, some ELISA based formats produce a color change that goes to blue or green, and does not proceed to yellow until it is exposed to a stop solution.

In other embodiments, the substrate of the second reagent R2 is a precipitating substrate formulated to catalyze the production of the visible signal OP by producing an insoluble colored product (a series of products P is shown in FIG. 6) when the second reagent R2 is in contact with the first reagent R1. Such precipitating substrates can include, for example, TMB (3,3',5,5' tetramethylbenzidine), DAB (3,3' diaminobenzidine), or 4 CN (4-chloro-1-napthol) based membrane substrates for horseradish peroxidase enzymes, or BCIP (5-bromo-4-chloro-3-indolyl-phosphate) based membrane substrates for alkaline phosphatase. In some embodiments, the precipitating substrate can be the BioFX® TMB HRP Membrane Substrates produced by Surmodics. In some embodiments, the precipitating substrate (and thus, the second reagent R2) can maintain stability when stored for up to one year in a liquid form at room temperature. In other embodiments, the precipitating substrate (and thus, the second reagent R2) can maintain stability when stored for up to two years in a liquid form at room temperature. Moreover, such precipitating substrates can produce a dark color, which can be easier to visualize and interpret. In some embodiments, the precipitating substrate can produce a colorimetric output that persists for at least one hour, at least two hours, at least three hours, at least 12 hours, at least 24 hours, or at least 48 hours.

Although the second reagent R2 is described as being stored in the device 2000 in a liquid form, in other embodiments, either the first reagent R1, the second reagent R2, or both the first reagent R1 and the second reagent R2 can be stored in any suitable form. For example, in some embodiments, the first reagent R1 and/or the second reagent R2 can be stored in lyophilized form to promote stability for one year, two years, or longer. Upon actuation (e.g., via the first reagent actuator 2080A or the second reagent actuator 2080B), the lyophilized reagents can be reconstituted for use within the device 2000.

Although shown and described as containing the first reagent R1 and the second reagent R2, in other embodiments, the reagent module 2700 (and any of the reagent modules described herein) can contain any suitable reagents and can be fluidically coupled to and/or can convey such reagents to any suitable module within the device 2000. For example, in some embodiments, the reagent volume can contain any of a sample wash, an elution buffer, one or more PCR reagents, a detection reagent and/or a substrate.

The detection module 2800 is configured to receive the detection solution S2 from the amplification module 1600 and the reagents from the reagent module 2700 to produce a visible signal (or output) OP to indicate presence or absence of a target organism in the input biological sample S1. Specifically, the detection module 2800 includes a cover 2802 and a detection housing 2810. The detection housing 2810 defines a detection channel 2812, and includes a detection surface 2821 within the detection channel 2812. The detection channel 2812 is in (or can be placed in) fluid communication with the amplification module 2600 and the reagent module 2700. In this manner, as described herein, the detection solution S2 containing the target amplicon can be conveyed into the detection channel 2812 and across the detection surface 2821. Additionally, the first reagent R1 and the second reagent R2 can be conveyed into the detection channel 2812 and across the detection surface 2821.

The detection surface 2821 includes a series of capture probes to which the target amplicon can be bound when the detection solutions S2 flows across the detection surface 2821. The capture probes can be any suitable probes formulated to capture or bind to the target amplicon. For example, in some embodiments, the capture probes can be any of single stranded nucleic acids, antibodies, or binding proteins. In some embodiments, the capture probes have the following general structure (DNA base sequences here are only examples, and will vary according to the target amplicon):

```
                                          (SEQ ID NO: 1)
   5' End-/5AmMC6/TCTCGTAAAGGGCAGCCCGCAAG-3'End
```

In other embodiments, the capture probes can be modified to also contain spacer molecules, as per this structure:

```
                                          (SEQ ID NO: 1)
5' End-/5AmMC6//iSpl8/TCTCGTAAAGGGCAGCCCGCAAG-3'End
```

Where /5AmMC6/ is the 5' Amino Modifier C6—Integrated DNA Technologies and /iSpl8/ is the Int Spacer 18—Integrated DNA Technologies. In other embodiments, the capture probes can be modified to include only the intended DNA bases, as per this structure:

```
                                          (SEQ ID NO: 1)
     5' End-TCTCGTAAAGGGCAGCCCGCAAG-3'End
```

In other embodiments, the capture probes also include extra non-target bases, as per this structure:

```
                                          (SEQ ID NO: 2)
   5' End-GGGGGGG TCTCGTAAAGGGCAGCCCGCAAG-3'End
```

In some embodiments, the capture probes can be formulated, designed or engineered to have a relatively high melting temperature (Tm) value (e.g., approximately 67° C.). In other embodiments, the capture probes can have a melting temperature (Tm) value that ranges from 35° C. to 85° C., 60° C. to 85° C., 60° C. to 75° C., 65° C. to 70° C., or 66° C. to 68° C. One advantage of capture probes having a high Tm value is that the flow cell can be heated to a wide range of temperatures during operation without causing the capture probe to release the target amplicon.

In some embodiments, the capture probes are designed against sequences from *Neisseria gonorrhoeae, Chlamydia trachomatis, Trichomonas vaginalis, Neisseria subflava* and a negative control sequence such as sequence from *Bacillus atrophaeus* or random bases.

The cover 2802 is coupled to the detection housing 2810 to enclose the detection channel 2812. In this manner, the cover 2802 and the detection housing 2810 form a "flow cell" for detection of target amplicon. In some embodiments, the cover 2802 includes a transparent portion through which the visible signal OP can be viewed. In some embodiments, the cover 2802 is coupled to the detection housing 2810 opposite from the detection surface 2821. In some embodiments, the detection channel 2812 has a rectangular cross-sectional shape characterized by a depth D and a width W (as shown in FIG. 6). The depth D and width W are selected to ensure that there is sufficient sample volume to fill the detection channel 2812. For example, if the depth D and width W are too large, the required sample volume to fill the detection channel 2812 will be greater than that which can be supplied by the modules within the test device 2000.

In contrast, the depth D and width W must be large enough to ensure that the visible signal OP can be easily seen. For example, the width W must be of sufficient size so that the detection surface 2821 can be easily seen. In some embodiments, the width W can be between about 2 mm and about 5 mm. In other embodiments, the width W can be between about 2 mm and about 10 mm. In yet other embodiments, the width W can be between about 2.5 mm and about 3.5 mm. The volume of the detection solution S2 above the detection surface 2821 (i.e., the depth D), can affect the intensity of the color generated during the reaction. A larger volume (or higher depth D) will generate a deeper color, while a lower volume will generate a paler color. In some embodiments, the depth D can be between about 0.125 mm and about 0.750 mm. In other embodiments, the depth D can be between about 0.125 mm and about 1.50 mm. In yet other embodiments, the depth D can be about 0.250 mm.

The molecular diagnostic test device 2000 (and any of the molecular diagnostic test devices described herein) can perform any of the methods described herein. For example, in some embodiments, the detection module 2800 can produce a colorimetric output (identified as OP in FIGS. 5 and 6) that indicates a presence of a target organism in the biological sample. The test device 2000 can produce a colorimetric output that is easily viewed by the user (i.e., can be of sufficient size and color properties) to be seen by the user without external aids (e.g., a magnifying glass, camera, or the like). In some embodiments, molecular diagnostic test device 2000 (and any of the molecular diagnostic test devices described herein) can perform a detection method as described below with reference to FIGS. 7 and 8 (and the detection module 3800).

Although the detection module 2800 is shown as including only a single detection surface 2821, in other embodiments, the detection module 2800 (or any of the detection modules shown and described herein) can include any suitable number of detection surfaces. For example, in some embodiments, a detection module can include up to five detection surfaces, each surface being configured to capture different amplicons and/or control organisms. In this manner, the detection module 2800 (and any of the detection modules shown and described herein) can facilitate a multiplex test. For example, in some embodiments, the detection module 2800 (and any of the detection modules shown and described herein) can include five detection surfaces to test for three different indications (plus two control surfaces). In other embodiments, a detection module can include up to 20 detection surfaces, each surface being configured to capture different amplicons and/or control organisms.

The detection surface 2821 (and any of the detection surfaces described herein) can have any suitable shape and area. The shape and area can facilitate visualizing the output signal OP produced from the detection surface. For example, in some embodiments, the detection surface 2821 (and any of the detection surfaces described herein) can have an area of between about 2 mm² and about 5 mm². In other embodiments, the detection surface 2821 (and any of the detection surfaces described herein) can have an area of between about 5 mm² and about 20 mm². Moreover, although shown as being oblong (or elliptical) in shape, in other embodiments, the detection surface 2821 (and any of the detection surfaces described herein) can be circular, rectangular, or any other suitable shape that facilitates the desired flow properties for the detection channel and visualization properties. For example, in some embodiments, the detection surface 2821 (and any of the detection surfaces described herein) can have an elliptical shape where a major axis of the ellipse is aligned with a direction of flow of the detection solution S2 within the detection channel 2812.

Although the detection surface 2821 is described as including a series of capture probes associated with a target amplicon, in other embodiments, the detection surface 2821 (and any of the detection surfaces described herein) can include a mixture of more than one capture probe. For example, in some embodiments, a detection surface can be a "positive control" surface that includes capture probes for both a control organism, as well as any organisms for which detection is sought. In this manner, the visible output signal will always appear from the positive control surface if the amplification is successful. In contrast, control detection surface only includes the captures probes associated with the positive control organism, there could be cases in which a highly positive amplification reaction from one of the target organisms could outcompete the control amplicon production, thus resulting no color of the positive control chamber. By including a mixture of more than one capture probe for a "positive control," the device 2000 (and any of the devices herein) can include an "always on" positive control, which can be easily read and interpreted.

Figure 7:
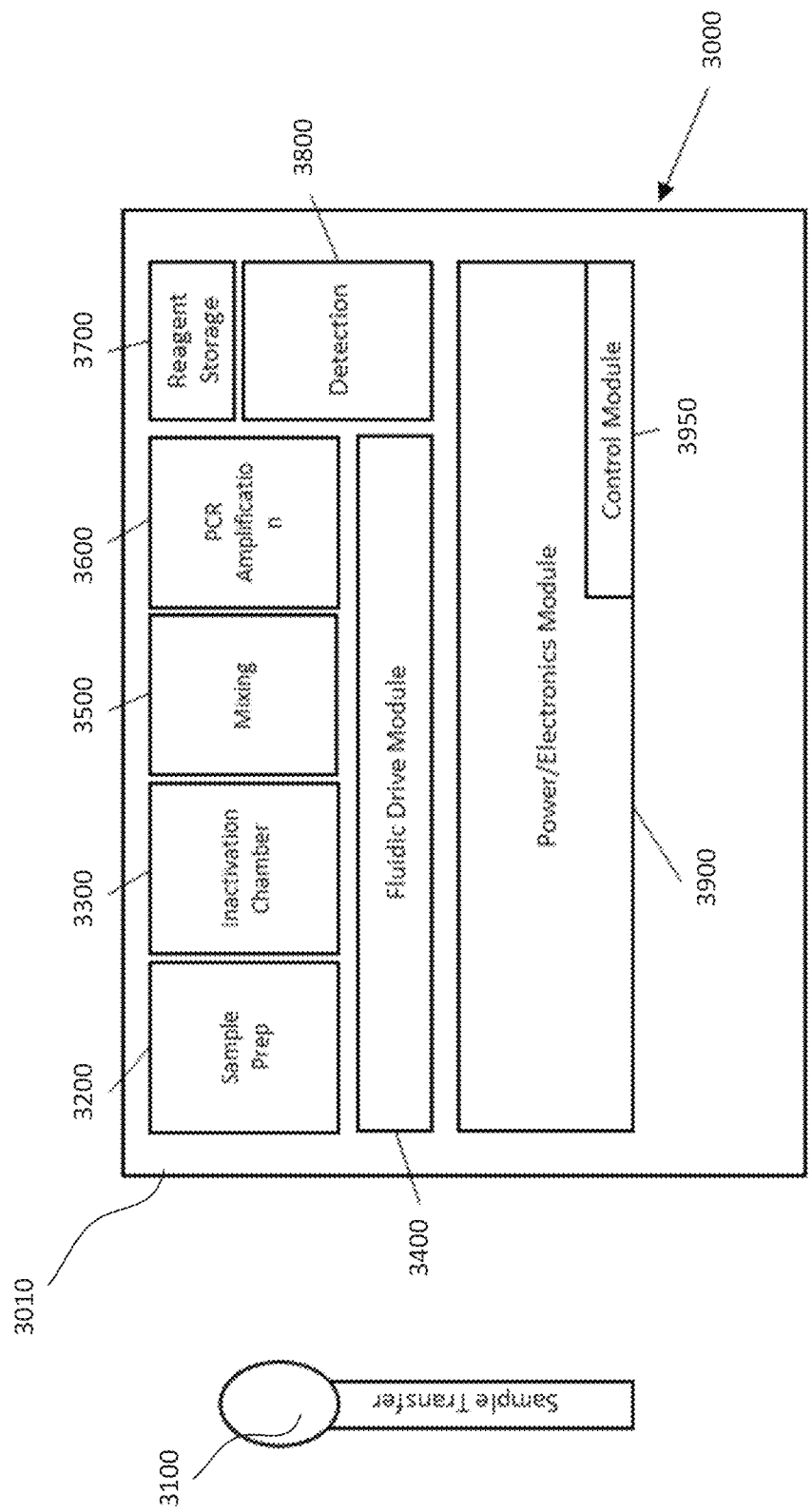
FIG. 7 is a schematic illustration of a molecular diagnostic device, according to an embodiment.

The detection module 2800 (and any of the amplification module described herein) can be used within any suitable diagnostic device, such as in any of the molecular diagnostic devices shown and described in International Patent Publication No. WO2016/109691, entitled "Devices and Methods for Molecular Diagnostic Testing," which is incorporated herein by reference in its entirety. One example of an integrated test device is shown in FIG. 7, which is a schematic block diagram of a molecular diagnostic system 3000 (also referred to as "system" or "diagnostic device"), according to an embodiment. The diagnostic device 3000 is configured to manipulate a sample to produce an optical indication (e.g., a colorimetric output) associated with a target cell according to any of the methods described herein. In some embodiments, the diagnostic device 3000 can be a single-use, disposable device that can provide an optical output without need for any additional instrument to manipulate or otherwise condition the diagnostic device 3000. Said another way, the diagnostic device 3000 is an integrated cartridge/instrument, and the entire unit can be used to perform a diagnostic assay and then be disposed. The diagnostic device 3000 includes a sample transfer device 3100, a sample preparation module 3200, an inactivation chamber 3300, a fluidic drive module 3400, a mixing chamber 3500, an amplification module 3600, a reagent storage module 3700, a detection module 3800, a power/electronics module 3900, and a control module 3950. A brief description of the major subsystems of the diagnostic device 3000 is provided below.

The sample transfer device 3100 is configured to transport a sample such as, for example, a blood, urine, male urethral specimens, vaginal specimens, cervical swab specimens, nasal swab specimens, or any other biological sample of the types described herein. The sample can be gathered using a commercially available sample collection kit, and can be conveyed, using the sample transfer device 3100, to the sample preparation module 3200. The sample collection kit can be a urine collection kit or swab collection kit. Non-limiting examples of such sample collection kits include Copan MSwab™ or BD ProbeTec™ Urine Preservative Transport Kit, Cat #440928, neat urine. The sample transfer device 3100 dispenses and/or otherwise transfers an amount of sample or sample/media to the sample preparation module 3200 through an input port (not shown, but which can be similar to the opening 1052 described above). The input port can then be capped. In some embodiments, the sample transfer device 3100 can be locked and/or fixedly coupled to the sample preparation module 3200 as a part of the dispensing operation. In this manner, the interface between the sample transfer device 3100 and the sample preparation module 3200 can be configured to prevent reuse of the diagnostic device 3000, transfer of additional samples, or the like. Although shown as including the sample transfer device 3100, in other embodiments, the diagnostic device 3000 need not include a sample transfer device.

In some embodiments, through a series of user actions or in an automated/semi-automated matter, the sample preparation module 3200 is configured to process the sample. For example, the sample preparation module 3200 can be configured to concentrate and lyse cells in the sample, thereby allowing subsequent extraction of DNA. In some embodiments, the processed/lysed sample is pushed and/or otherwise transferred from the sample preparation module 3200 to the inactivation chamber 3300, which is configured to inactivate, in the lysed sample, the proteins used during lysing. In some embodiments, the fluidic drive module 3400 is configured to aspirate the sample from the inactivation chamber 3300, and is further configured to convey the sample to the amplification module 3600. The fluidic drive module 3400 is also configured to convey the sample and/or reagents (e.g., from the reagent storage module 3700) to perform any of the methods of diagnostic testing described herein. Similarly stated, the fluidic drive module 3400 is configured to generate fluid pressure, fluid flow and/or otherwise convey the input sample through the modules of the device.

The mixing chamber 3500 mixes the output of inactivation chamber 3300 with the reagents necessary to conduct an amplification reaction (e.g., PCR). In some embodiments, the mixing chamber 3500 can contain the amplification reagents in the form of one or more lyophilized reagent beads that contain the primers and enzymes necessary for the amplification reaction. In such embodiments, the mixing chamber 3500 can be configured to hydrate and/or reconstitute the lyophilized beads in a given input volume, while ensuring even local concentrations of reagents in the entirety of the volume. The mixing chamber 3500 can include any suitable mechanism for producing the desired solution, such as, for example, a continuous flow mixing channel, an active mixing element (e.g., a stir rod) and/or a vibratory mixing element. The mixed sample is then conveyed to the amplification module 3600 (e.g., by the fluidic drive module 3400).

The amplification module 3600 is configured to amplify the sample (e.g., via polymerase chain reaction (PCR)) to generate an amplified sample, in any manner as described herein. For example, in some embodiments, the amplification module 3600 can be similar to the amplification module 4600 (or any other amplification module described herein). After amplification, the amplified sample (also referred to as the detection solution) is further pushed, transferred or conveyed to a detection module 3800. In some embodiments, the detection module 3800 is configured to run and/or facilitate a colorimetric enzymatic reaction on the amplified sample. In particular, a series of reagents from the reagent storage module 3700 can be conveyed by the fluidic drive module 3400 to facilitate the optical output from the test. In some embodiments, the various modules/subsystems of the main diagnostic device 3000 are controlled and/or powered by the power/electronics module 3900 and the control module 3950.

In some embodiments, the control module 3950 can include one or more modules, and can automatically control the valves, pumps, power delivery and/or any other components of the diagnostic device 3000 to facilitate the molecular testing as described herein. The control module 3950 can include a memory, a processor, an input/output module (or interface), and any other suitable modules or software to perform the functions described herein.

Figure 8:
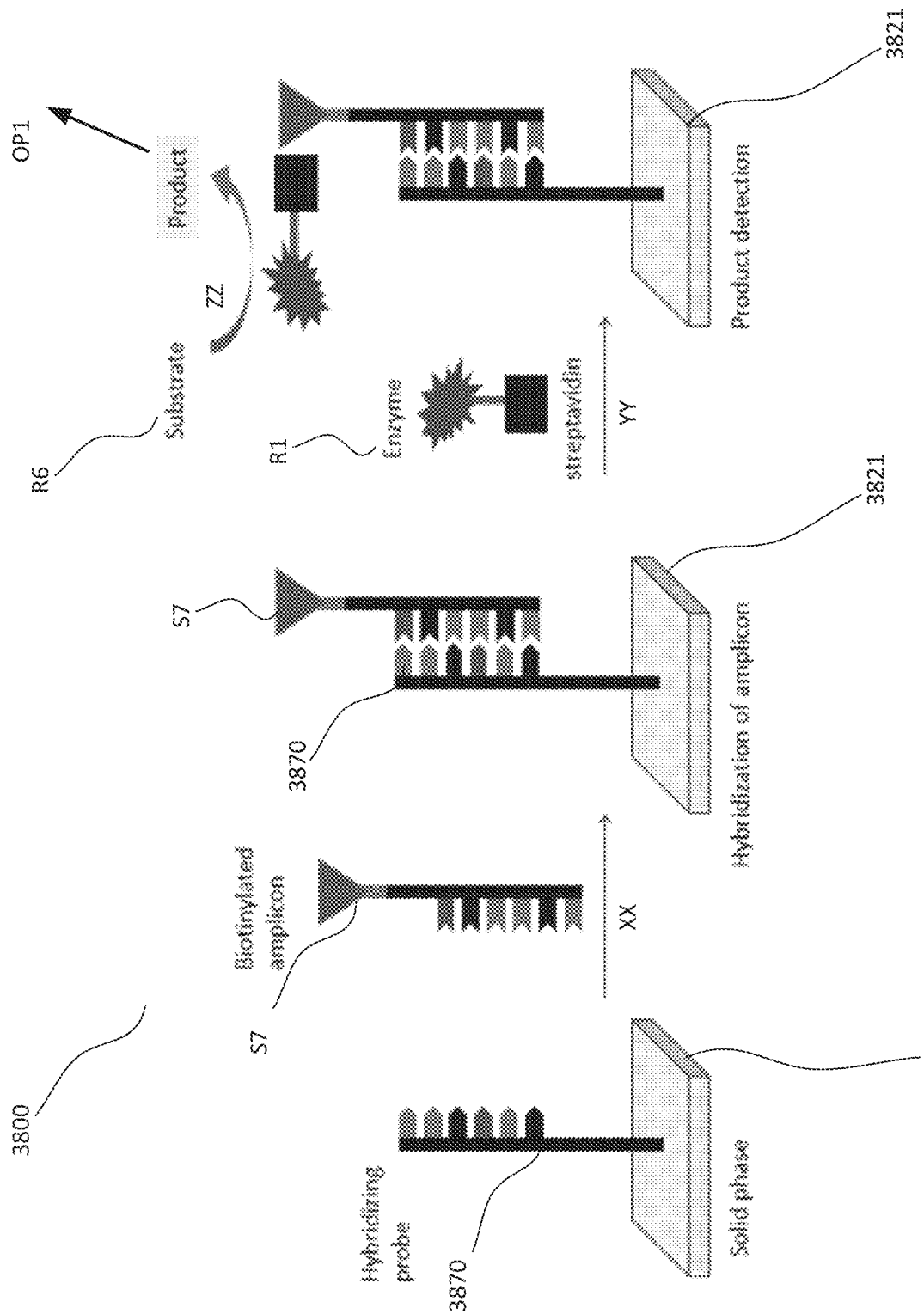
FIG. 8 is a diagram illustrating an enzyme linked reaction, according to an embodiment, resulting in the production a colorimetric result.

FIG. 8 illustrates a portion of the operations and/or features associated with an enzymatic reaction, according to an embodiment, that can be conducted by or within the detection module 3800, or any other detection module described herein (e.g., the detection module 2800 or 4800 described herein). In some embodiments, the enzymatic reaction can be carried out to facilitate visual detection of a molecular diagnostic test result using the device 3000, the device 4000, or any other devices or systems described herein. The reaction, the detection module 3800, and/or the remaining components within the test unit 3000 can be collectively configured such that the test unit 3000 is a single-use device that can be used in a point-of-care setting and/or in a user's home. Similarly stated, in some embodiments, the test unit 3000 (and any of the other devices shown and described herein) can be configured for use in a decentralized test facility. Further, in some embodiments, the reaction shown in FIG. 8 can facilitate the test unit 3000 (and any of the other devices shown and described herein) operating with sufficient simplicity and accuracy to be a CLIA-waived device. Similarly stated, in some embodiments, the reaction shown in FIG. 8 can provide the output signal OP1 in a manner that poses a limited likelihood of misuse and/or that poses a limited risk of harm if used improperly. In some embodiments, the reaction can be successfully completed within the test unit 3000 (or any other device described herein) upon actuation by a user with minimal (or no) scientific training, in accordance with methods that require little judgment of the user, and/or in which certain operational steps are easily and/or automatically controlled.

As shown, the detection module 3800 includes a detection surface 3821 within a read lane or flow channel. The detection surface 3821 is spotted and/or covalently bonded with a specific hybridizing probe 3870, such as an oligonucleotide. The hybridizing probe 3870 (also referred to as a capture probe) can be similar to any of the capture probes described herein, including those described in conjunction with the detection surface 2821. In some embodiments, the hybridizing probe 3870 is specific for a target organism and/or amplicon. The bonding of the hybridizing probe 3870 to the detection surface 3821 can be performed using any suitable procedure or mechanism. For example, in some embodiments, the hybridizing probe 3870 can be covalently bound to the detection surface 3821.

Reference S7 illustrates the biotinylated amplicon that is produced from the amplification step such as, for example, by the amplification module 3600 of FIG. 7 (or any other amplification modules described herein). The biotin can be incorporated within the amplification operation and/or within the amplification module 3600 in any suitable manner. As shown by the arrow XX, the output from the amplification module, including the biotinylated amplicon S7 is conveyed within the read lane and across the detection surface 3821. The hybridizing probe 3870 is formulated to hybridize to the target amplicon S7 that is present within the flow channel and/or in proximity to the detection surface 3821. The detection module 3800 and/or the detection surface 3821 is heated to incubate the biotinylated amplicon S7 in the read lane in the presence of the hybridizing probe 3870 for a few minutes allowing binding to occur. In this manner, the target amplicon S7 is captured and/or is affixed to the detection surface 3821, as shown. Although disclosed as being labeled with biotin, in other embodiments, the target molecules can be labeled in any suitable manner that will allow binding of the complex comprising a sample molecule binding moiety and an enzyme capable of facilitating a colorimetric reaction. For example, in some embodiments, the target molecules can be labeled with one or more of the following: streptavidin, fluorescein, Texas Red, digoxigenin, or Fucose.

In some embodiments, a first wash solution (not shown in FIG. 8) can be conveyed across the detection surface 3821 and/or within the flow channel to remove unbound PCR products and/or any remaining solution. In other embodiments, however, no wash operation is conducted.

As shown by the arrow YY, a detection reagent R1 is conveyed within the read lane and across the detection surface 3821. The detection reagent R1 can be any of the detection reagents described herein, include those described as being the first reagent R1 within the reagent module 2700. In some embodiments, the detection reagent R1 can be a horseradish peroxidase (HRP) enzyme ("enzyme") with a streptavidin linker. In some embodiments, the streptavidin and the HRP are cross-linked to provide dual functionality. As shown, the detection reagent is bound to the captured amplicon S7. The detection module 3800 and/or the detection surface 3821 is heated to incubate the detection reagent R1 within the read lane in the presence of the biotinylated amplicon S7 for a few minutes to facilitate binding.

In some embodiments, a second wash solution (not shown in FIG. 8) can be conveyed across the detection surface 3821 and/or within the flow channel to remove unbound detection reagent R4. In other embodiments, however, no second wash operation is conducted.

As shown by the arrow ZZ, a detection reagent R2 is conveyed within the read lane and across the detection surface 3821. The detection reagent R2 can be can be any of the detection reagents described herein, include those described as being the second reagent R2 within the reagent module 2700. The detection reagent R2 can be, for example, a substrate formulated to enhance, catalyze and/or promote the production of the signal OP1 from the detection reagent R1. Specifically, the substrate is formulated such that upon contact with the detection reagent R1 (the HRP/streptavidin) a colorimetric output signal OP1 is developed where HRP attaches to the amplicon. The color of the output signal OP1 indicates the presence of bound amplicon: if the target pathogen, target amplicon and/or target organism is present, the color product is formed, and if the target pathogen, target amplicon and/or target organism is not present, the color product does not form.

Similarly stated, upon completion of the reaction, if the target pathogen, target amplicon and/or target organism is present the detection module produces a signal OP1. In accordance with the reaction described in FIG. 8, the signal OP1 is a non-fluorescent, visual signal that can viewed by the user (e.g., through a detection opening or window defined by a device housing). This arrangement allows the device to be devoid of a light source (e.g., lasers, light-emitting diodes or the like) and/or any light detectors (photomultiplier tube, photodiodes, CCD devices, or the like) to detect and/or amplify the signal OP1.

Said another way, the reaction produces a colorimetric output signal that is visible to the user, and that requires little to no scientific training and/or little to no judgment to determine whether the target organism is present. In some embodiments, the reagents R1, R2 are formulated such that the visible signal OP1 remains present for at least about 30 minutes. In some embodiments, the visible signal OP1 remains present for at least about an hour. In some embodiments, the visible signal OP1 remains present for at least about two hours, at least about 12 hours, at least about 24 hours, or at least about 48 hours. In some embodiments, the reagents R1, R2 can be stored within a housing (not shown in FIG. 8) in any manner as described herein (e.g., in a sealed container, a lyophilized form or the like).

Figure 9:
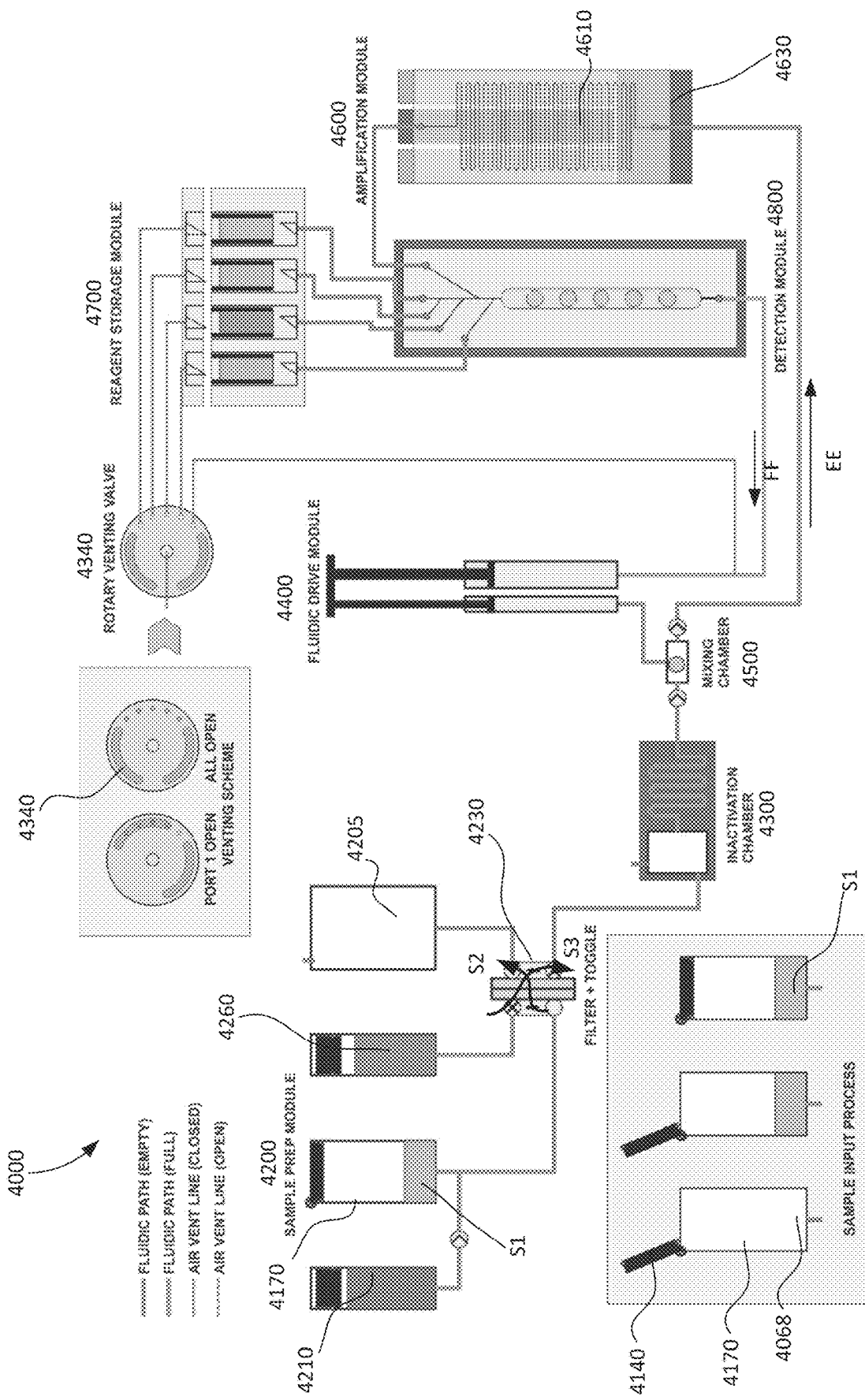
FIG. 9 is a schematic illustration of a molecular diagnostic test device, according to an embodiment.
Figure 10:
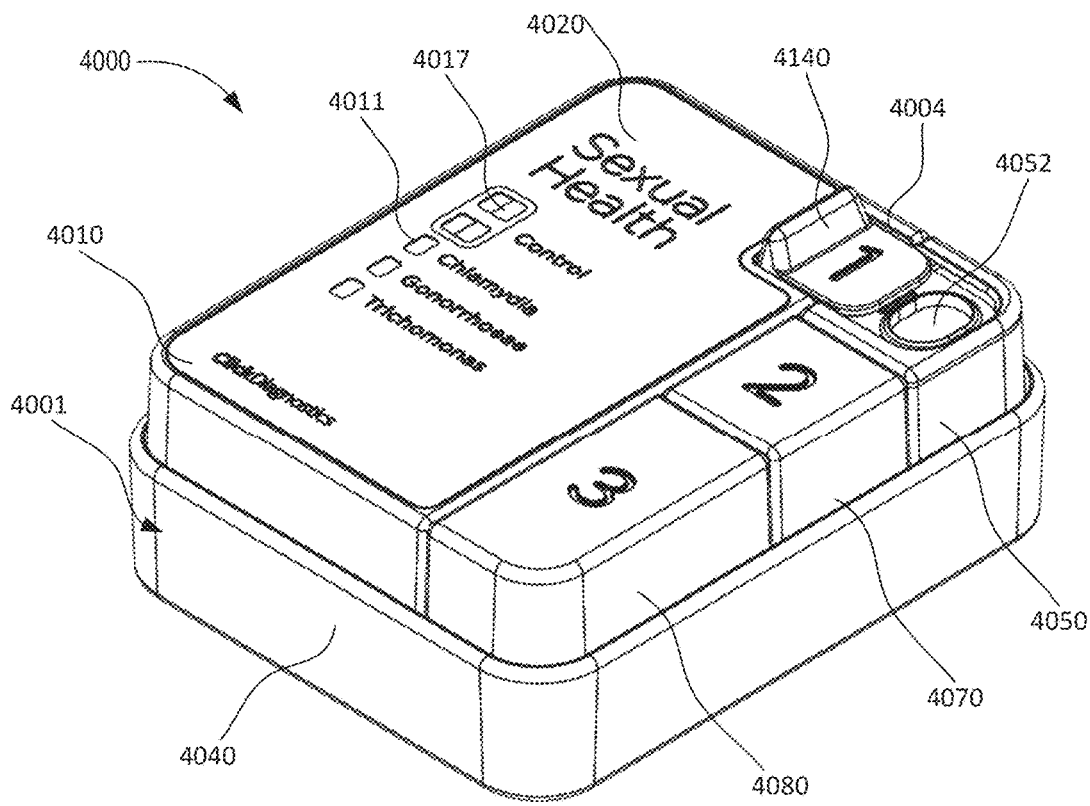
FIGS. 10 and 11 are a perspective view and a top view, respectively, of a molecular diagnostic test device, according to an embodiment.
Figure 11:
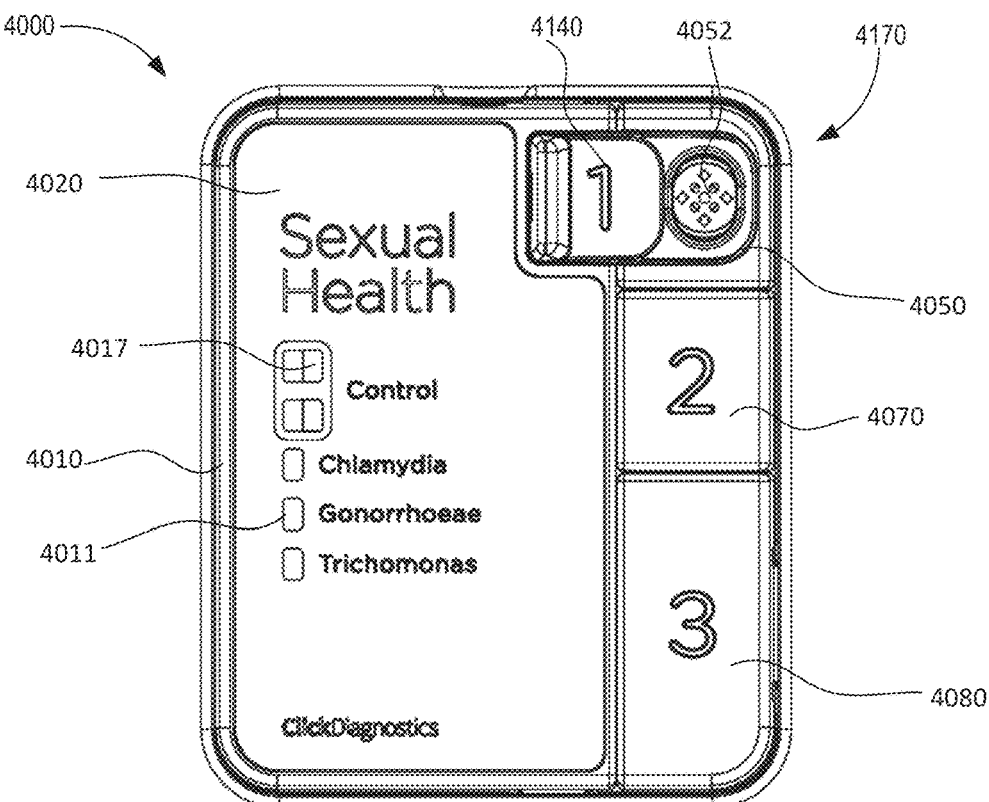
Figure 12:
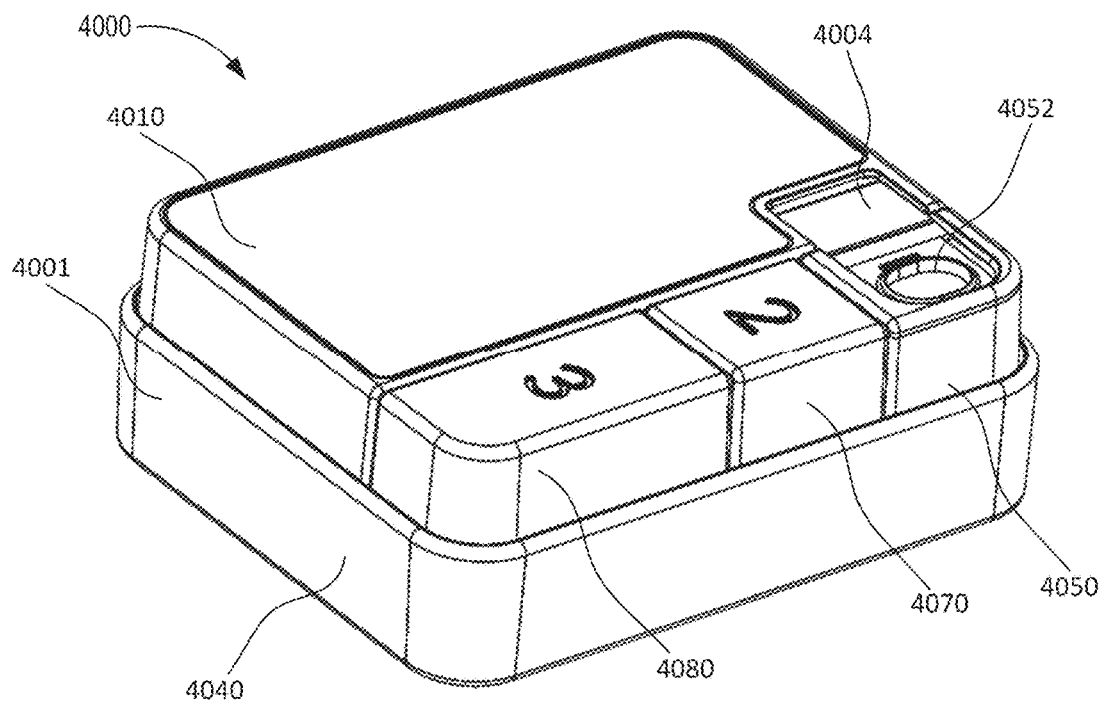
FIG. 12 is a perspective view of the molecular diagnostic test device shown in FIGS. 10 and 11, with the lid removed to show the sample input opening.
Figure 13:
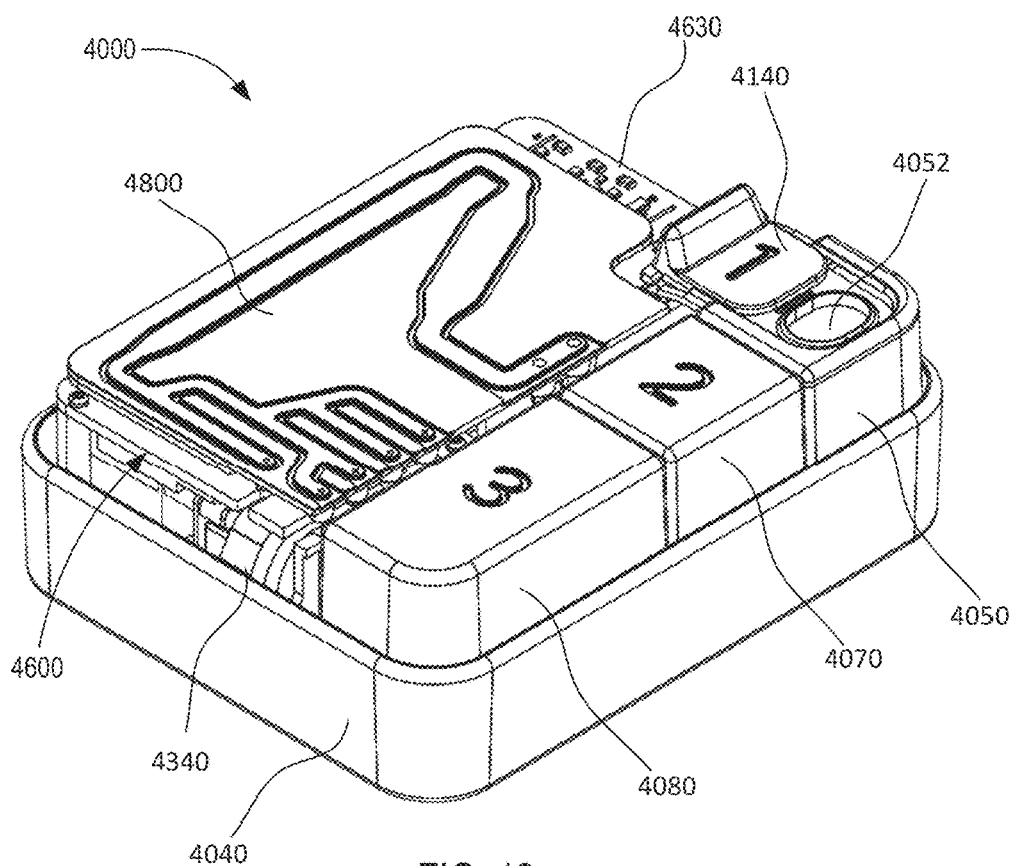
FIG. 13 is a perspective view of the molecular diagnostic test device shown in FIGS. 10 and 11, with the top portion of the housing removed to show the internal components.

FIG. 9 is a schematic illustration of a molecular diagnostic test device 1000 (also referred to as a "test device" or "device"), according to an embodiment. The schematic illustration describes the primary components of the test device 4000 as shown in FIG. 10. The test device 4000 is an integrated device (i.e., the modules are contained within a single housing) that is suitable for use within a point-of-care setting (e.g., doctor's office, pharmacy or the like), decentralized test facility, or at the user's home. In some embodiments, the device 4000 can have a size, shape and/or weight such that the device 4000 can be carried, held, used and/or manipulated in a user's hands (i.e., it can be a "handheld" device). A handheld device may have dimensions less than 15 cm×15 cm×15 cm, or less than 15 cm×15 cm×10 cm, or less than 12 cm×12 cm×6 cm. In other embodiments, the test device 4000 can be a self-contained, single-use device. In some embodiments, the test device 4000 can be configured with lock-outs or other mechanisms to prevent re-use or attempts to re-use the device.

Further, in some embodiments, the device 4000 can be a CLIA-waived device and/or can operate in accordance with methods that are CLIA waived. Similarly stated, in some embodiments, the device 4000 (and any of the other devices shown and described herein) is configured to be operated in a sufficiently simple manner, and can produce results with sufficient accuracy to pose a limited likelihood of misuse and/or to pose a limited risk of harm if used improperly. In some embodiments, the device 4000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 4000 can be configured for long term storage in a manner that poses a limited likelihood of misuse (spoilage of the reagent(s), expiration of the reagents(s), leakage of the reagent(s), or the like). In some embodiments, the molecular diagnostic test device 4000 is configured to be stored for up to about 36 months, up to about 32 months, up to about 26 months, up to about 24 months, up to about 20 months, up to about 48 months, or any values there between.

The test device 4000 is configured to manipulate a biological sample S1 to produce one or more output signals associated with a target cell. Specifically, the device 4000 includes a sample preparation module 4200, an inactivation module 4300 (also referred to as a lysing module), a fluidic drive (or fluid transfer) module 4400, a mixing chamber 4500, an amplification module, a detection module and a power and control module (not shown). The test device and certain components therein can be similar to any of the molecular test devices shown and described herein or in International Patent Publication No. WO2016/109691, entitled "Devices and Methods for Molecular Diagnostic Testing," which is incorporated herein by reference in its entirety. Accordingly, a detailed description of certain modules (e.g., the fluidic drive module 4400) is not provided herein. A description of each of the modules is provided below.

Figure 14:
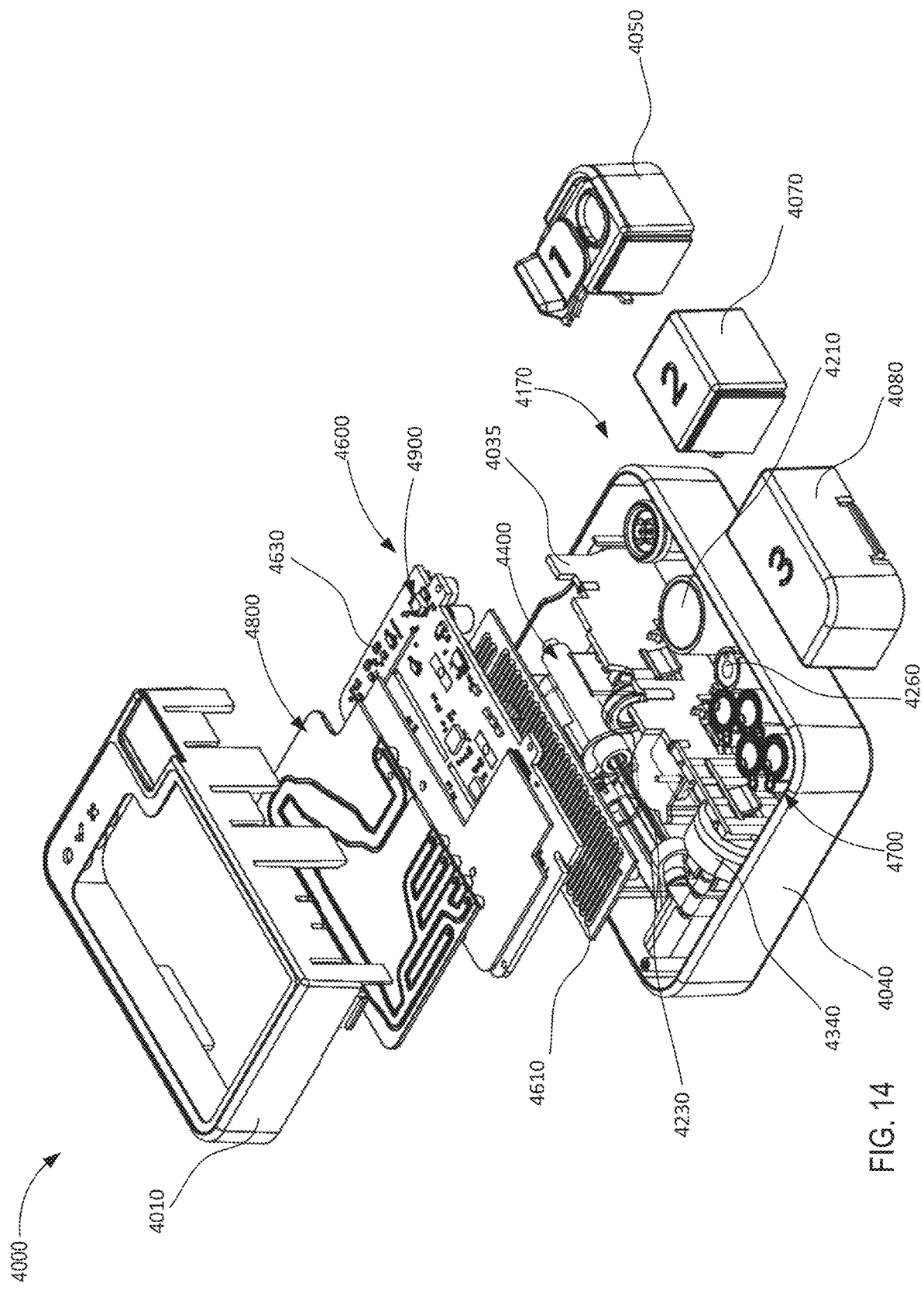
FIG. 14 is an exploded view of the molecular diagnostic test device shown in FIGS. 10 and 11.
Figure 65:
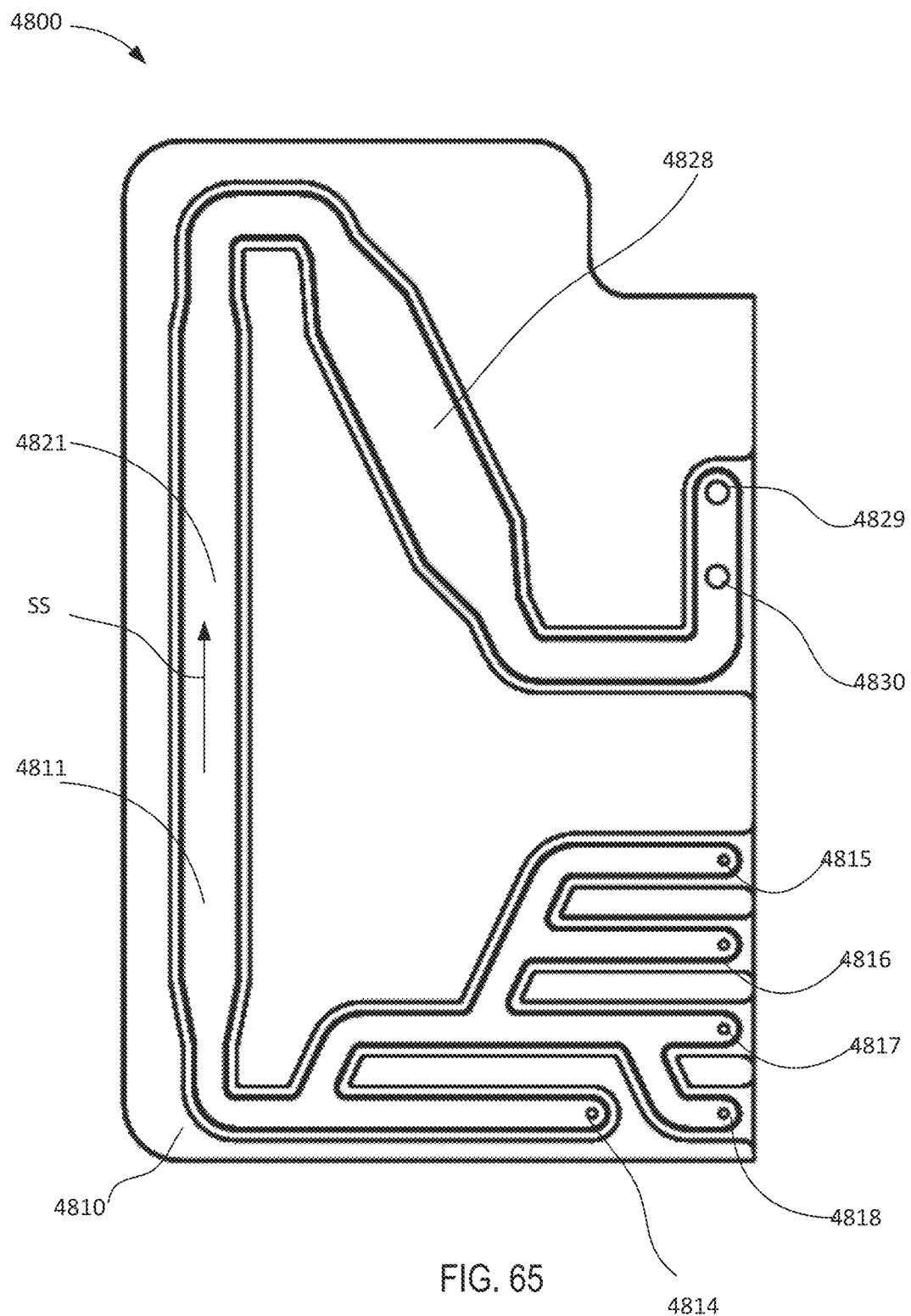

FIGS. 10-65 show various views of the molecular diagnostic test device 4000. The test device 4000 is configured to manipulate an input sample to produce one or more output signals associated with a target cell, according to any of the methods described herein. The diagnostic test device 4000 includes a housing 4001 (including a top portion 4010 and a bottom portion 4030), within which the modules described herein are fully or partially contained. Similarly stated, the housing 4001 (including the top portion 4010 and/or the bottom portion 4030) at least partially surround and/or enclose the modules. As shown in FIG. 14, the device 4000 includes a sample input module 4170, a sample preparation module 4200, an inactivation module 4300, a fluidic drive (or fluid transfer) module 4400, a mixing chamber 4500, an amplification module 4600, a detection module 4800, a reagent storage module 4700, a rotary venting valve 4340, and a power and control module 4900. In some embodiments, the sample preparation module 4200 can be considered as including the sample input module 4170 and/or the inactivation (also referred to as the lysing) module 4300, but in other embodiments, these modules can be considered as distinct from the sample preparation module 4200. A description of the housing assembly 4001 if followed by a description of each module and/or subsystem.

The housing assembly 4001 includes the top housing 4010, the bottom housing 4040, the vertical manifold 4035 (see FIGS. 18 and 19), the sample transfer manifold 4100. As shown, the top housing 4010 includes a label 4020 that defines a series of detection openings 4011 that are aligned with the detection module 4800. In this manner, the signal produced by and/or on each detection surface of the detection module 4800 is visible through the appropriate detection opening 4011. In some embodiments, the top housing 4010 and/or the label 4020 is opaque (or semi-opaque), thereby "framing" or accentuating the detection openings. In some embodiments, for example, the top housing 4010 can include markings 4017 (e.g., thick lines, colors or the like) to highlight the detection opening 4011. For example, in some embodiments, the top housing 4010 can include indicia 4017 identifying the detection opening to a specific disease (e.g., *Chlamydia trachomatis* (CT), *Neisseria gonorrhea* (NG) and *Trichomonas vaginalis* (TV)) or control. In other embodiments, the top housing 4010 can include a series of color spots having a range of colors associated with a range of colors that is likely produced by the signals produced during the test. In this manner, the housing and/or the label 4020 can contribute to reducing the amount of user judgment required to accurately read the test.

Figure 52:
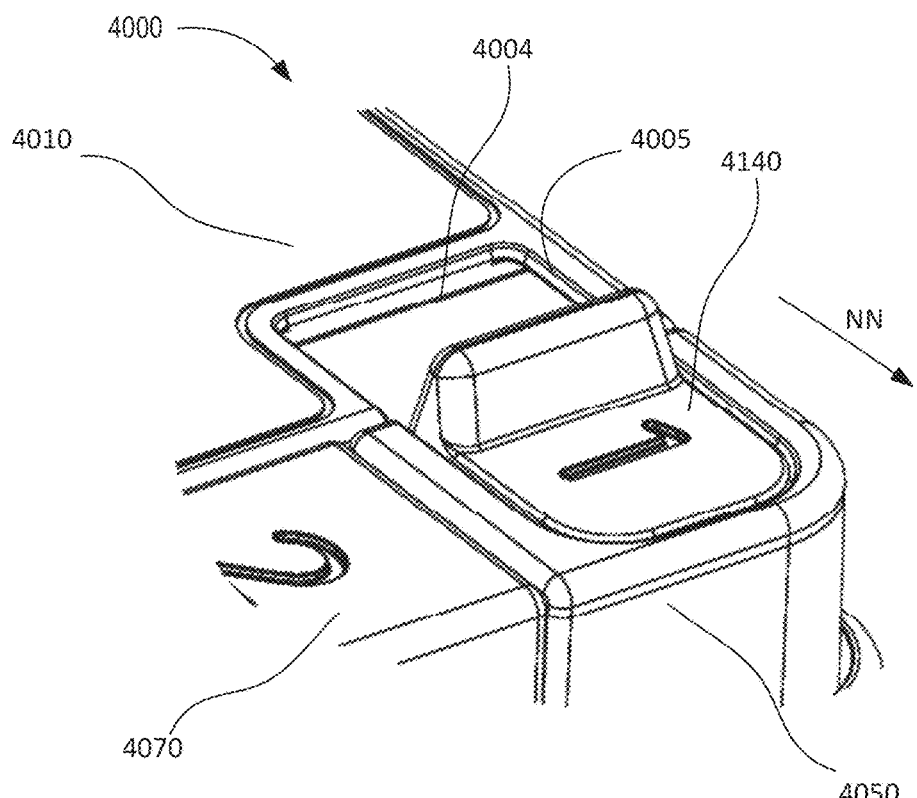
FIG. 52 is an enlarged view of a portion of the top housing of the molecular diagnostic test device shown in FIGS. 10 and 11, showing the lid in a closed position.
Figure 53:
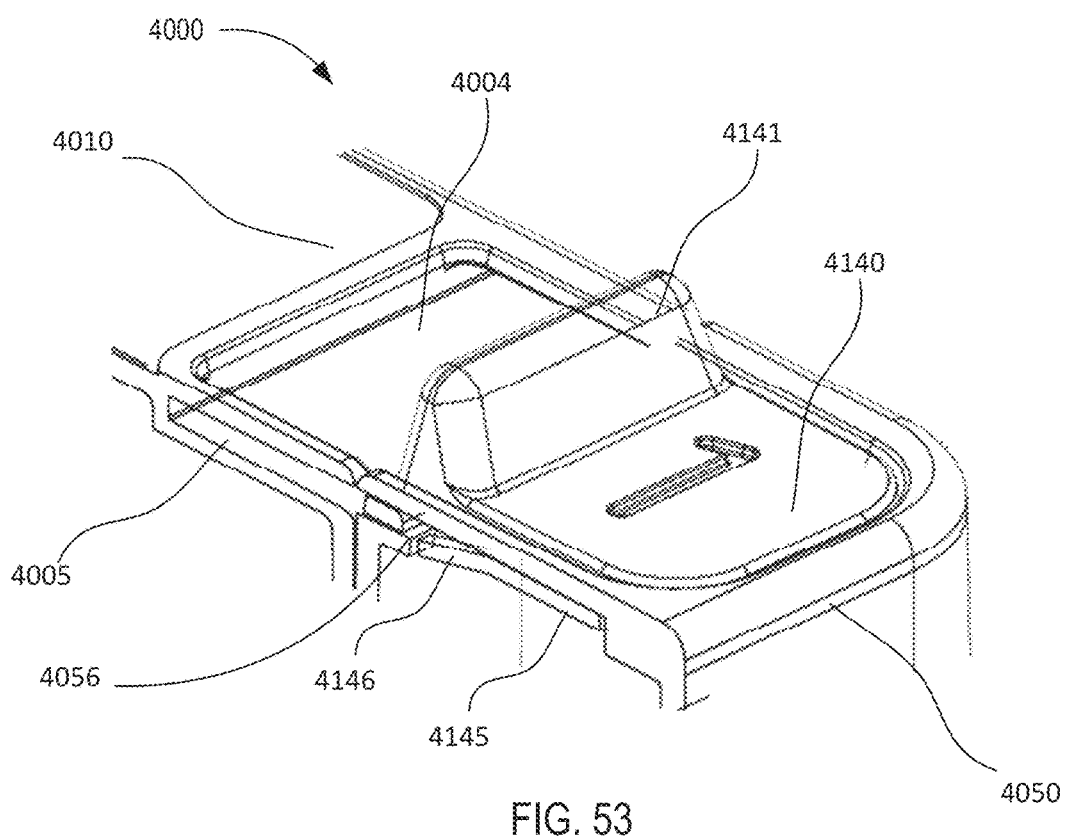
FIG. 53 is perspective cross-sectional view of a portion of the top housing of the molecular diagnostic test device shown in FIGS. 10 and 11, showing the lid in the closed position.
Figure 54:
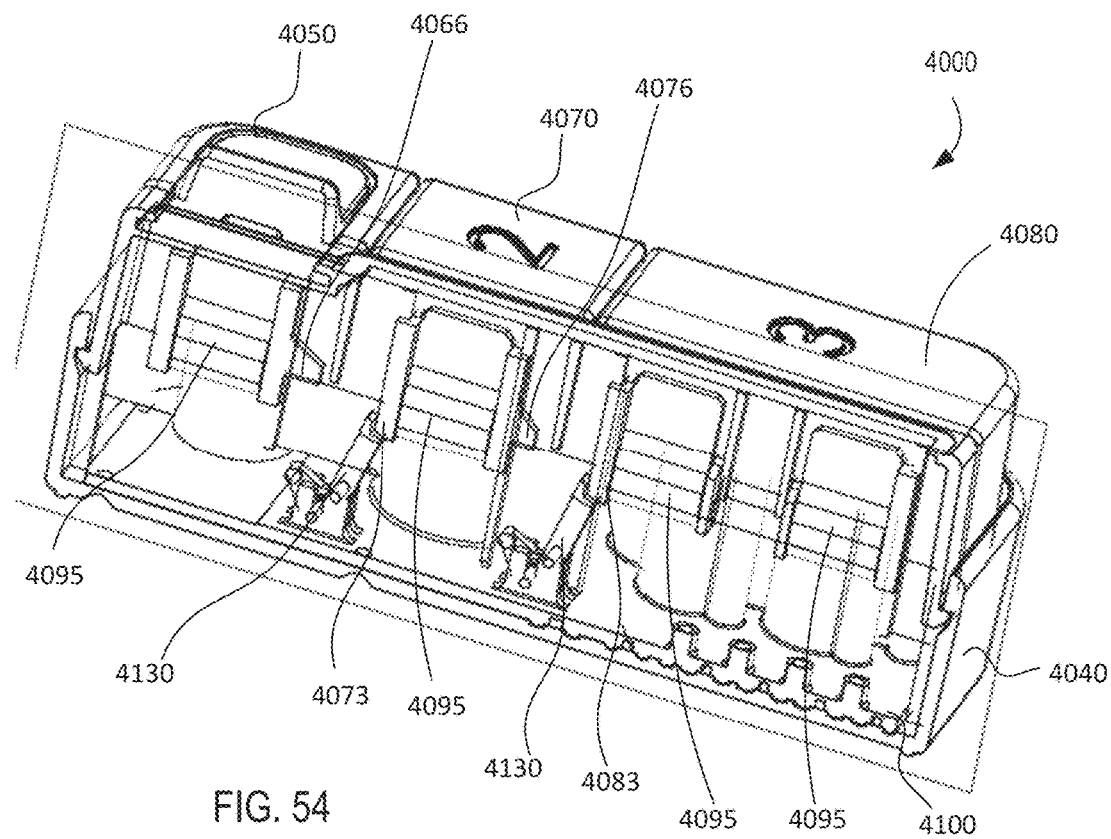
FIGS. 54 and 55 are a perspective cross-sectional view and a rear view, respectively, of a portion of the molecular diagnostic test device shown in FIGS. 10 and 11, showing the lid in the closed position and the sample input actuator in its first position.

Referring to FIGS. 12, 15, 52 and 53, the top housing 4010 includes a lid portion 4004 to which the sample lid 4140 is movably coupled. The lid portion 4004 includes a recessed surface against which the lid 4140 can be moved, and defines a series of channels 4005. As shown in FIGS. 52 and 53, the channels 4005 slidably receive the rails (also referred to as protrusions) 4145 of the lid 4140. In this manner, as described below, when the lid 4140 is in the first lid (i.e., "opened") position, the rails 4145 engage a shoulder or lock surface that defines the channels 4005 thereby preventing movement of the lid 4140 and a direction non-parallel to the direction shown by the arrow NN in FIG. 52. In this manner, the top housing 4010 includes a lock surface to which the lid 4140 engages to prevent downward motion of the lid 4140 and the sample input actuator 4050 when the lid 4140 is in the opened position.

Figure 15:
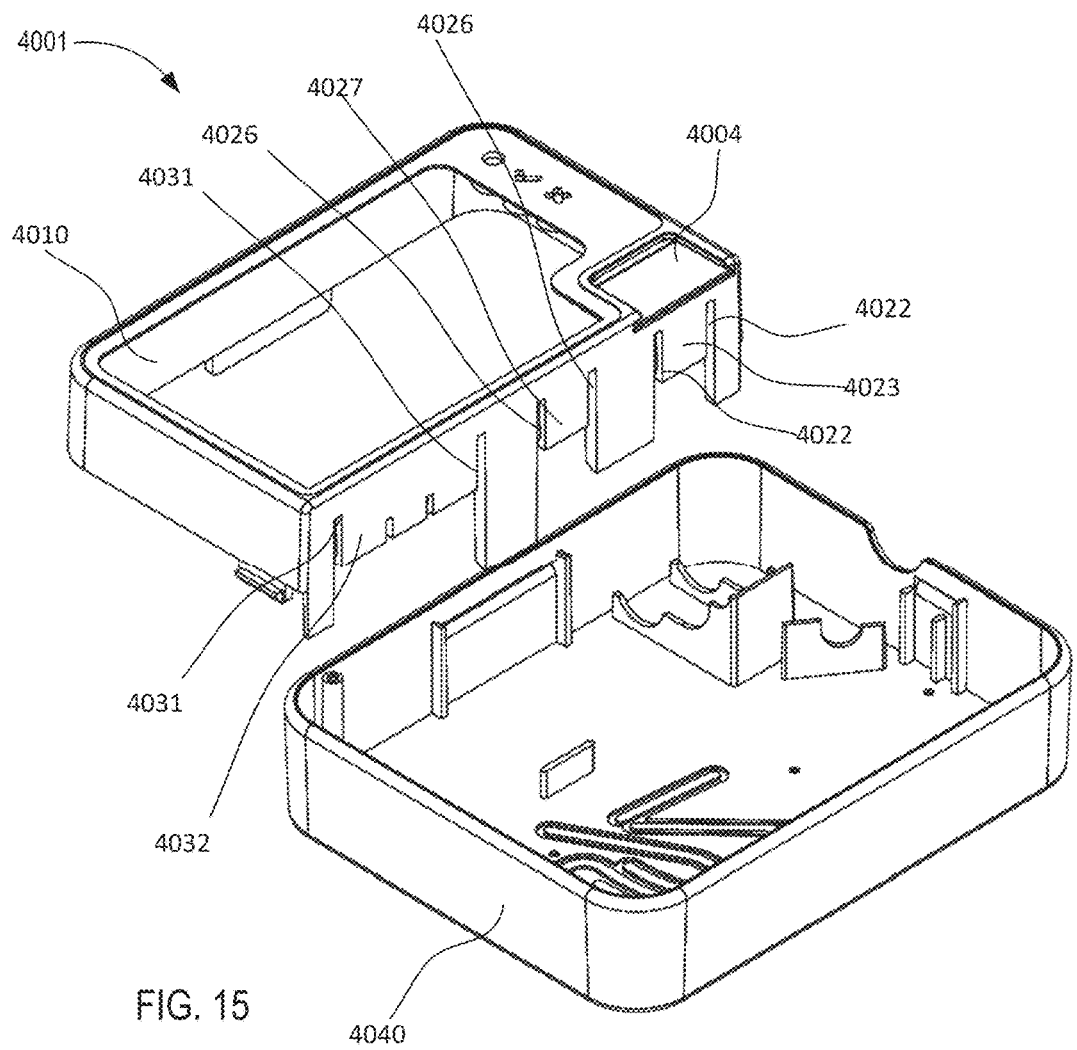
FIG. 15 is a top perspective exploded view of a portion of the housing assembly of the molecular diagnostic test device shown in FIGS. 10 and 11.
Figure 16:
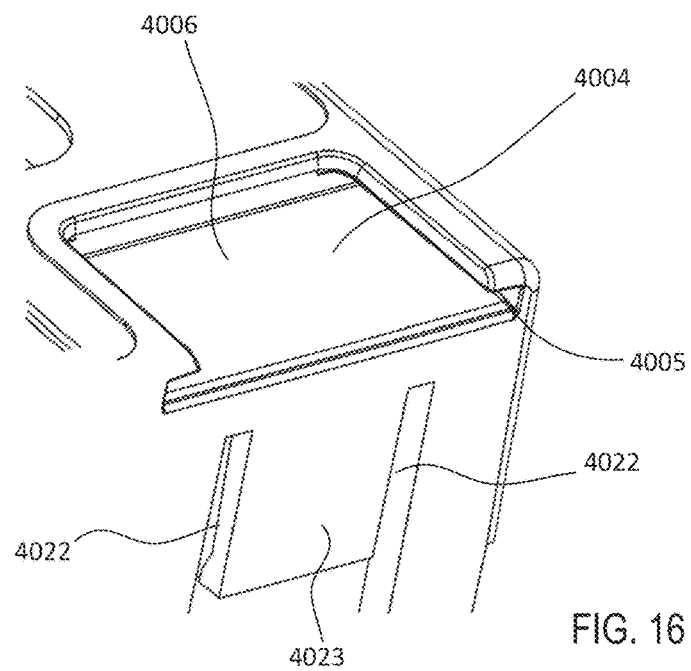
FIG. 16 is an enlarged view of a portion of the top housing shown in FIG. 15, showing lid engagement portion.
Figure 17:
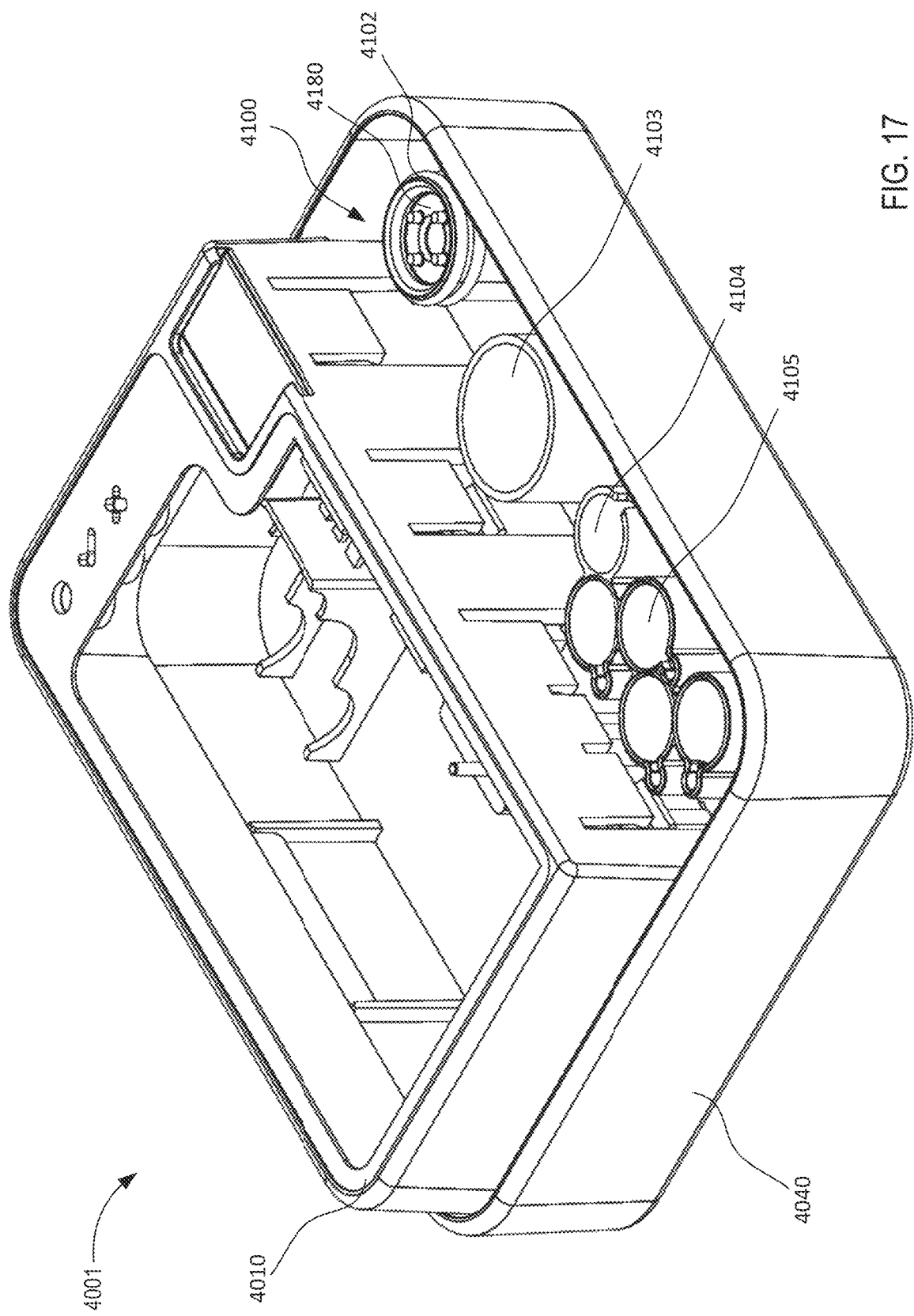
FIGS. 17 and 18 are a front perspective view and a rear perspective view, respectively, of the housing assembly of the molecular diagnostic test device shown in FIGS. 10 and 11.

Referring to FIG. 15, the top housing 4010 defines a series of actuator guide slots, each pair of which engages one of the actuator buttons, as described herein. In particular, the top housing 4010 defines a first pair of actuator guide slots 4022 that slidingly receive the mounting protrusions 4063 of the first (or sample input) actuator 4050. The top housing 4010 includes a lock protrusion 4023 between the two guide slots 4022 that engages the spring clip 4095 coupled to the first actuator 4050 when the first actuator 4050 is in its second (or actuated) position. In this manner, the top housing 4010 includes a lock surface (i.e., the lock protrusion 4023) that maintains the first actuator 4050 in its second (or actuated) position to prevent reuse of the diagnostic device 4000, transfer of additional samples into the sample input module 4170, or attempts to actuate the first actuator 4050 multiple times. The top housing 4010 defines a second pair of actuator guide slots 4026 that slidingly receive the mounting protrusions 4073 of the second (or wash) actuator 4070. The top housing 4010 includes a lock protrusion 4027 between the two guide slots 4026 that engages the spring clip 4095 coupled to the second actuator 4070 when the second actuator 4070 is in its second (or actuated) position. In this manner, the top housing 4010 includes a lock surface (i.e., the lock protrusion 4027) that maintains the second actuator 4070 in its second (or actuated) position to prevent reuse of the diagnostic device 4000, or attempts to actuate the second actuator 4070 multiple times. The top housing 4010 defines a third pair of actuator guide slots 4031 that slidingly receive the mounting protrusions 4083 of the third (or reagent) actuator 4080. The top housing 4010 includes a pair of lock protrusions 4032 between the two guide slots 4031 that engage the spring clips 4095 coupled to the third actuator 4080 when the third actuator 4080 is in its second (or actuated) position. In this manner, the top housing 4010 includes a lock surface (i.e., the lock protrusions 4032) that maintain the third actuator 4080 in its second (or actuated) position to prevent reuse of the diagnostic device 4000, or attempts to actuate the third actuator 4080 multiple times.

Figure 18:
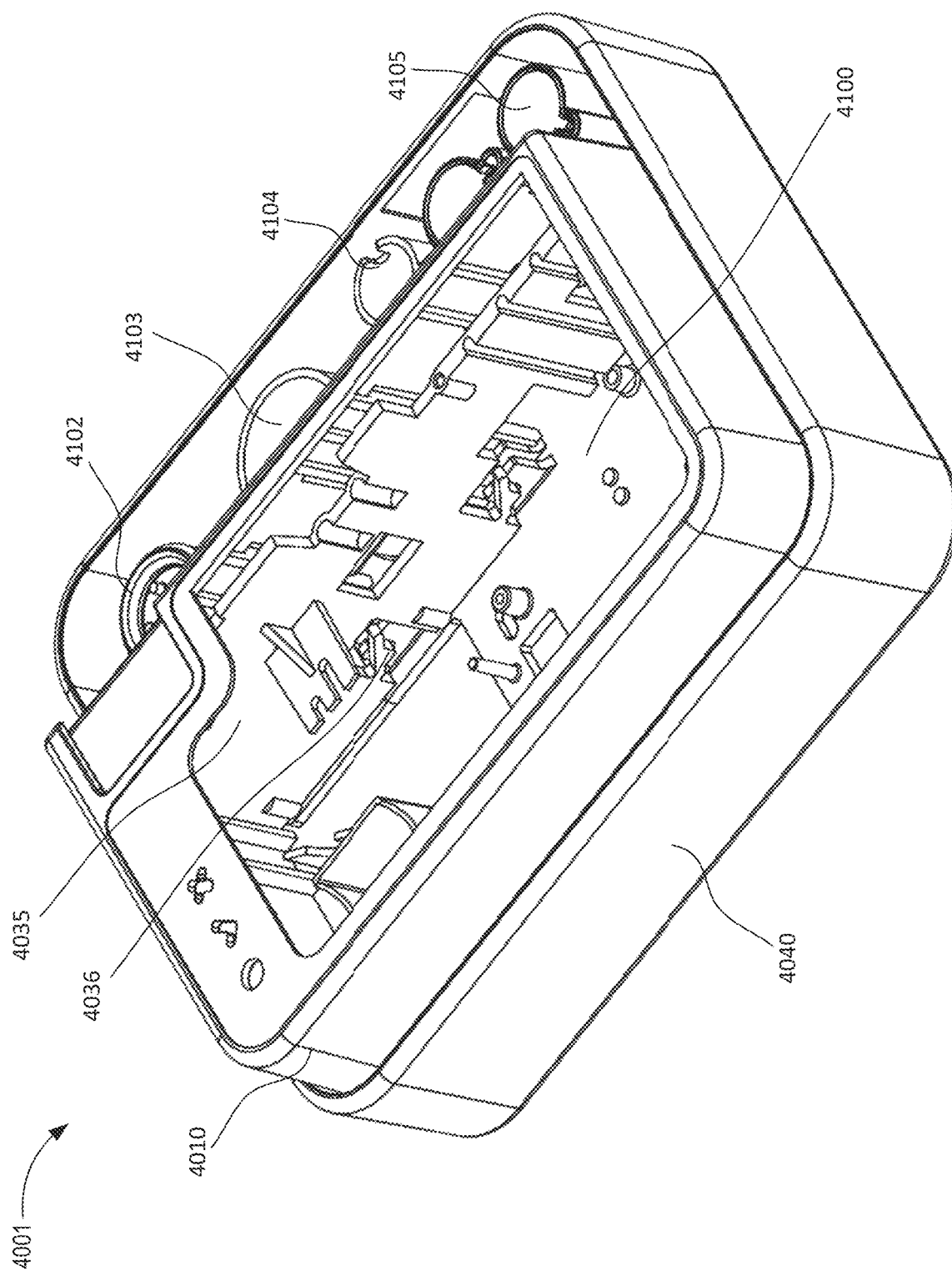
Figure 19:
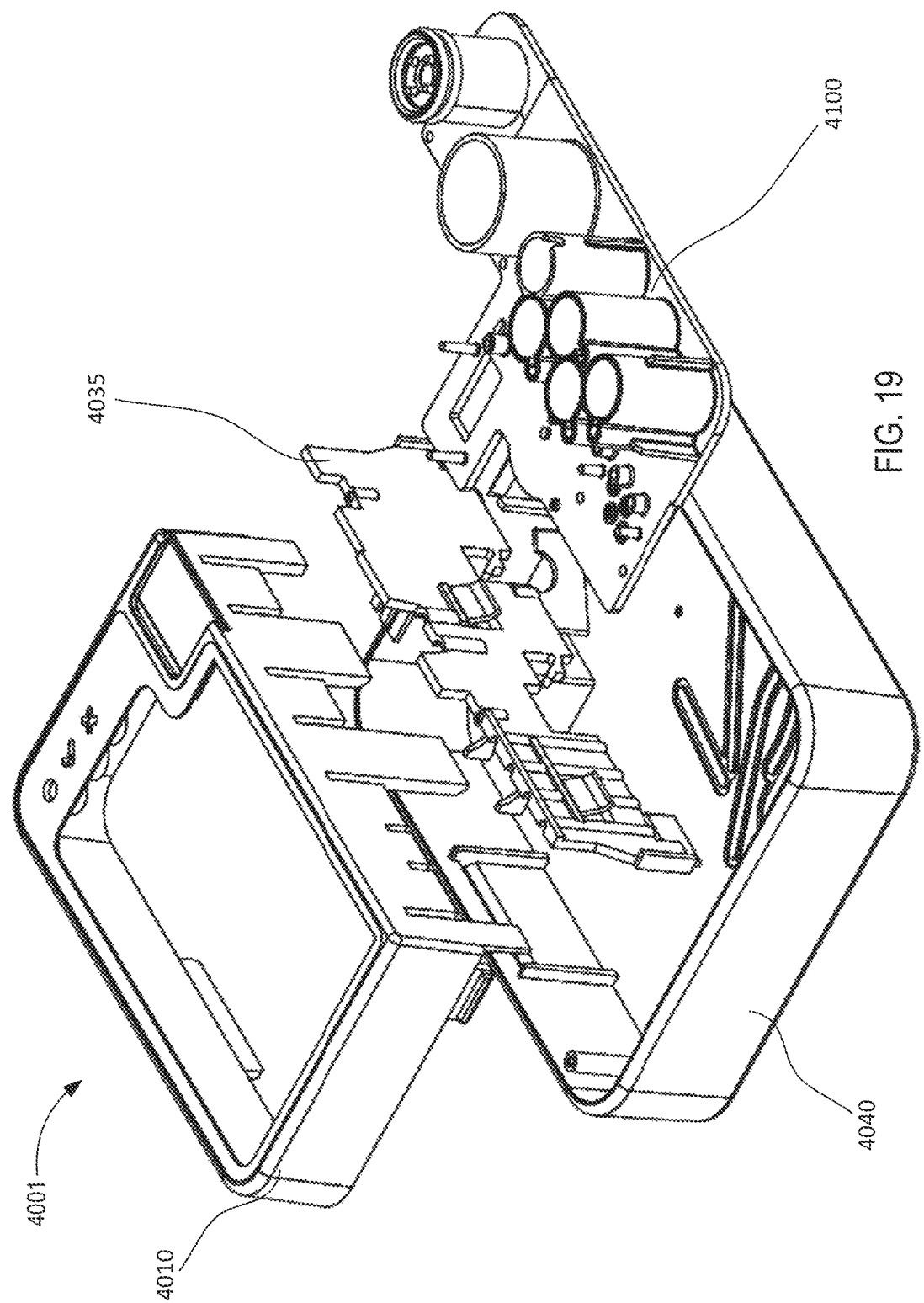
FIG. 19 is a perspective exploded view of the housing assembly shown in FIGS. 17 and 18.
Figure 20:
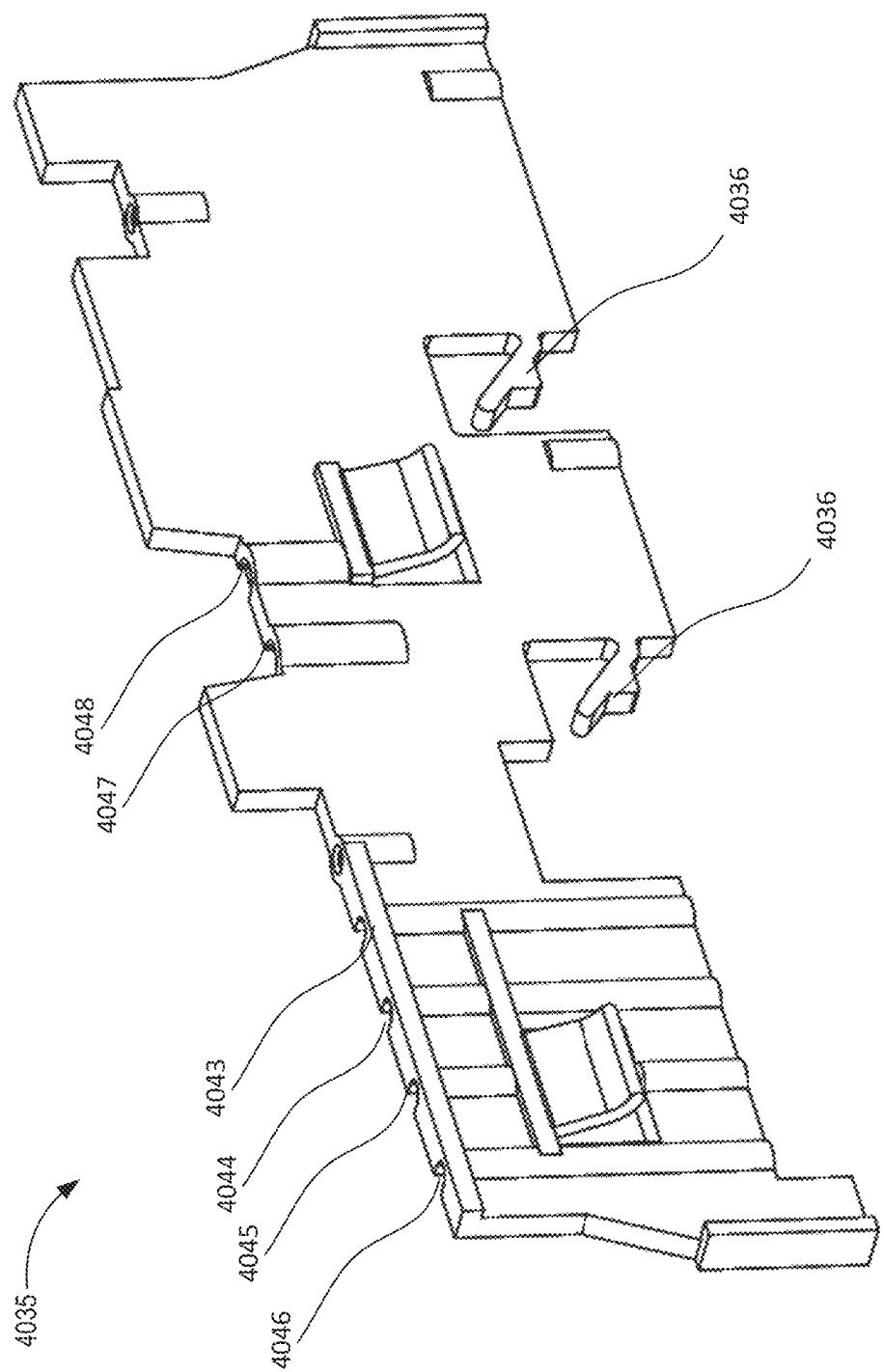
FIG. 20 is a perspective view of the vertical manifold of the housing assembly shown in FIGS. 17 and 18.
Figure 21:
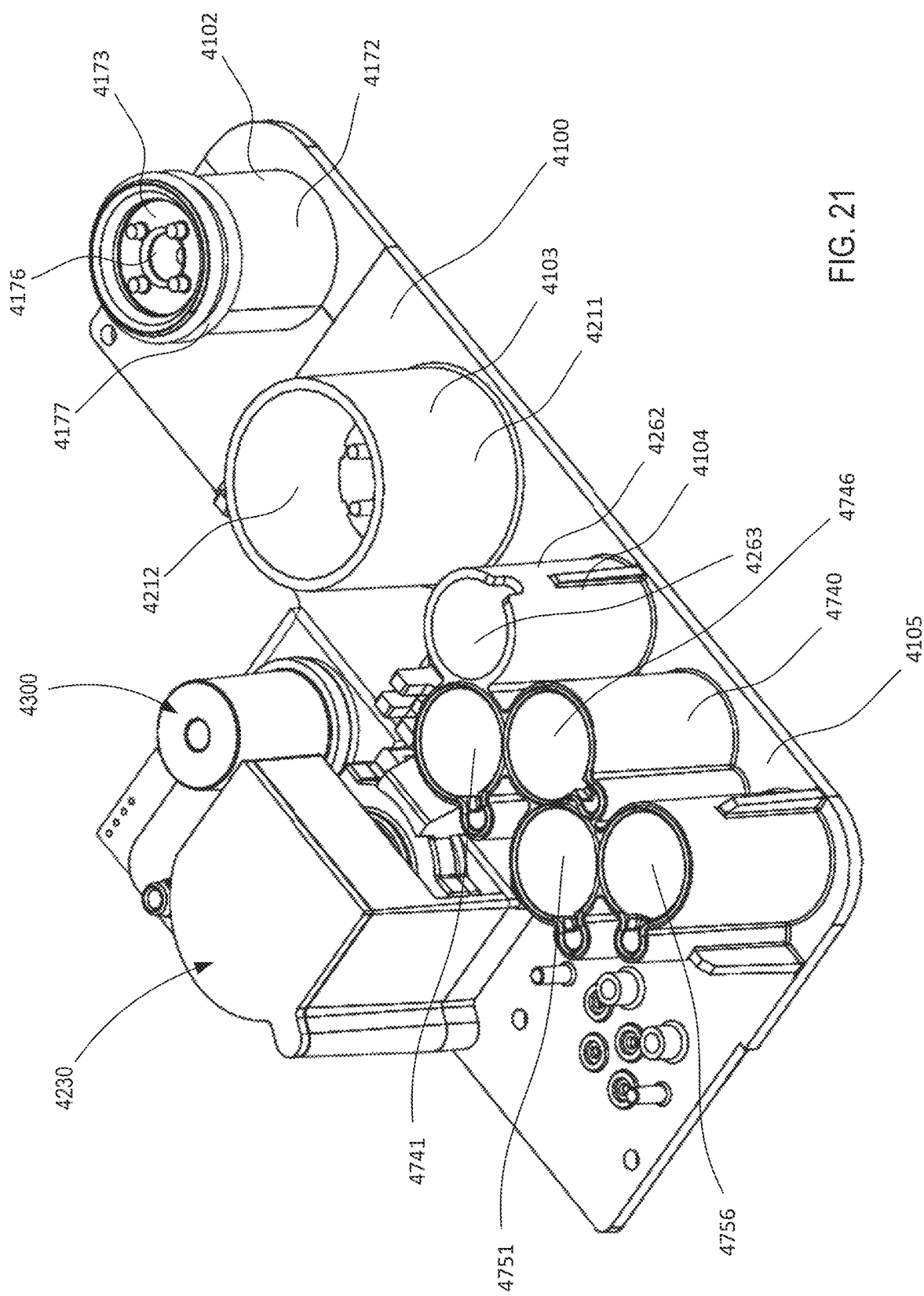
FIG. 21 is a perspective view of the sample transfer manifold of the housing assembly shown in FIGS. 17 and 18, including a filter assembly and an inactivation assembly coupled thereto.
Figure 22:
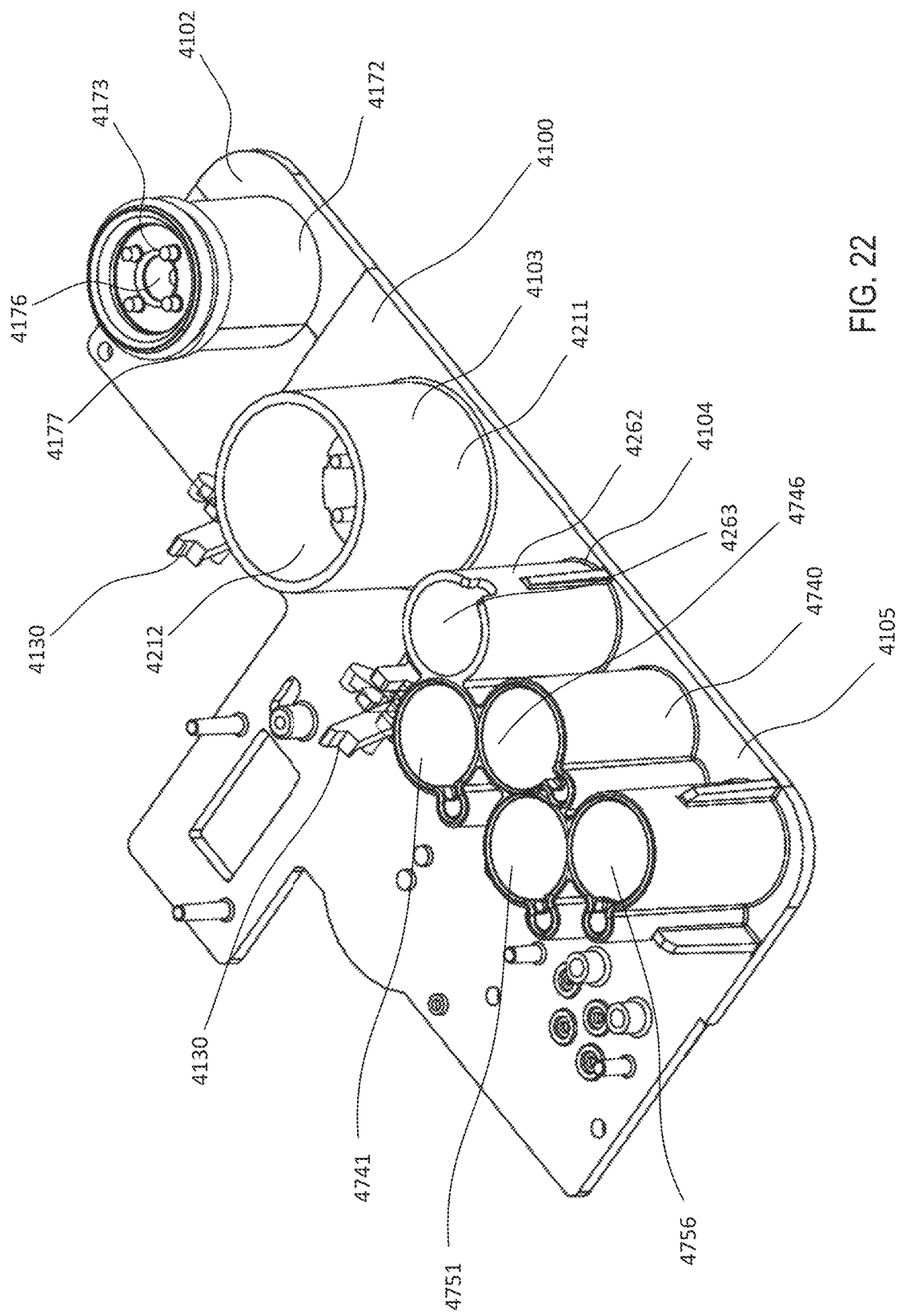
FIGS. 22-25 are a front perspective view, a rear perspective view, a bottom view, and a top view, respectively, of the sample transfer manifold of the housing assembly shown in FIGS. 17 and 18.
Figure 23:
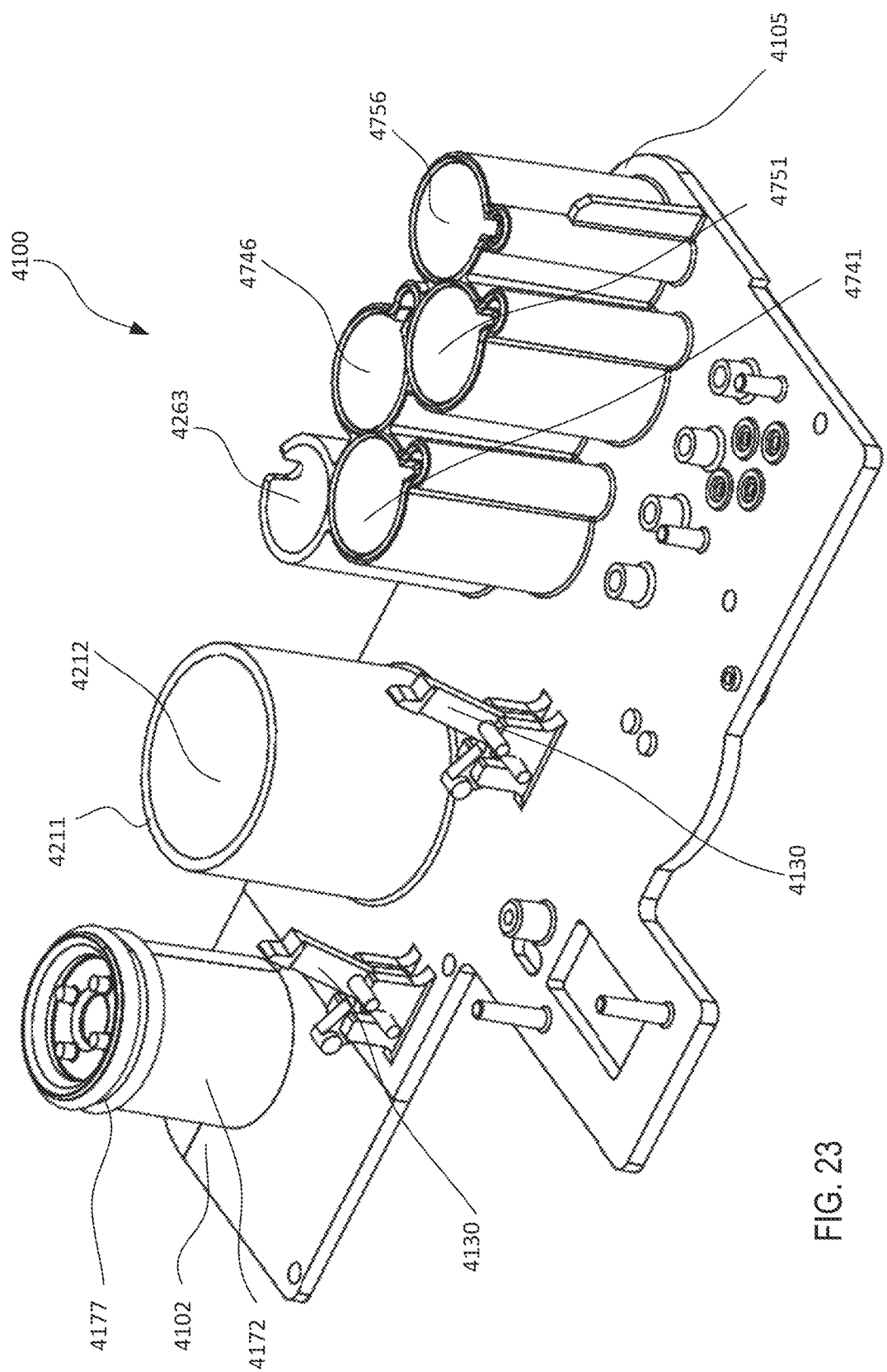
Figure 55:
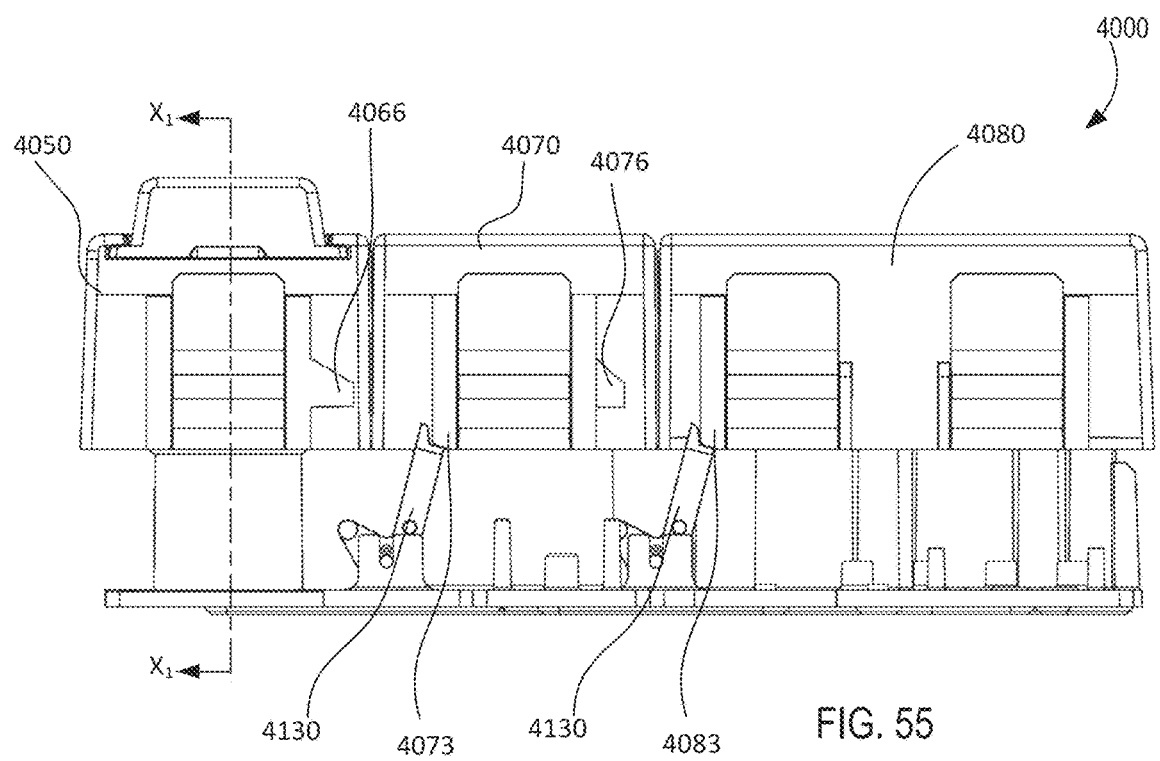
Figure 57:
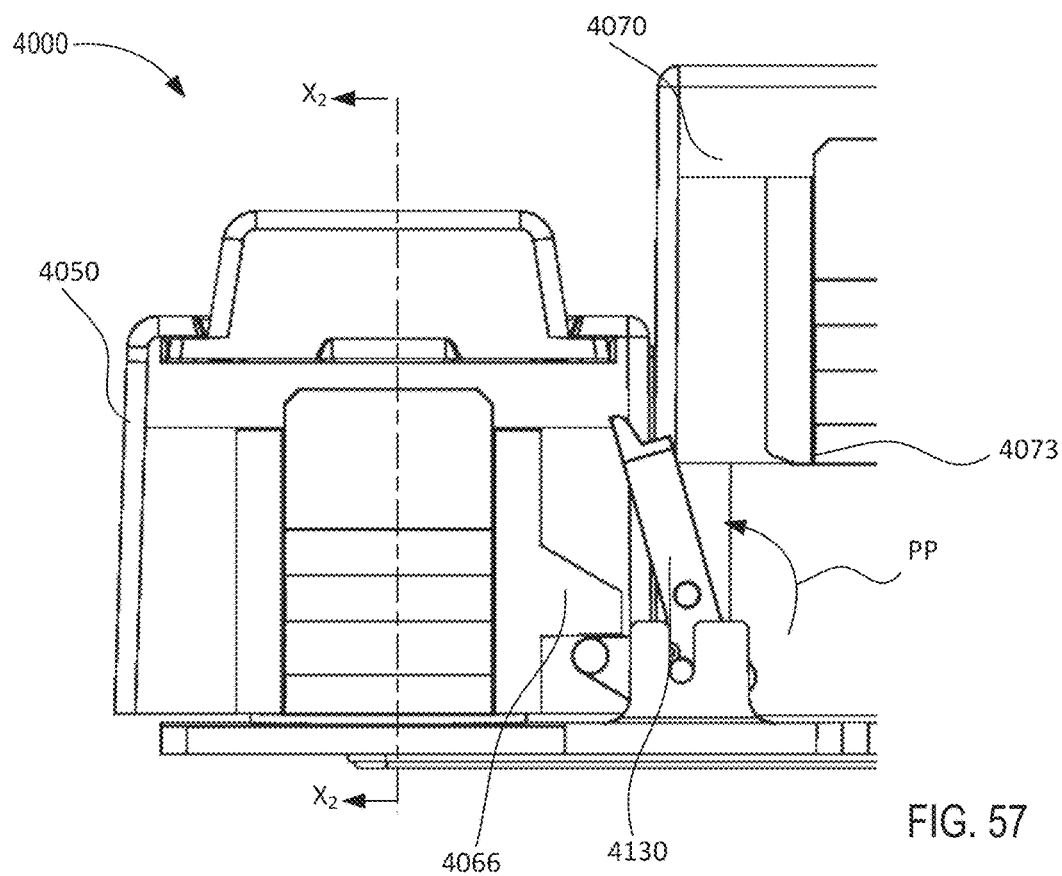

Referring to FIG. 20, the housing assembly 4001 includes the vertical manifold 4035, which provides both structural support and defines flow paths for various fluids that are conveyed within the device 4000. In particular, the vertical manifold 4035 includes two lock arms 4036. As shown in FIG. 18, the lock arms 4036 are positioned against the reagent locks (or lock levers) 4130 (see FIGS. 55 and 57) to maintain the reagent locks 4130 in their locked positions. The vertical manifold 4035 defines a series of reagent passages through which reagents are conveyed from the reagent module 4700 to the detection module 4800. Specifically, the vertical manifold 4035 defines a first reagent passage 4043 through which a first reagent (e.g., a wash) can flow into the detection module 4800, a second reagent passage 4044 through which a second reagent (e.g., a detection reagent) can flow into the detection module 4800, a third reagent passage 4045 through which a third reagent (e.g., a detection reagent, such as a substrate) can flow into the detection module 4800, and a fourth reagent passage 4046 through which a fourth reagent (e.g., a second volume of a detection reagent, such as a substrate) can flow into the detection module 4800. Additionally, the vertical manifold 4035 defines a first vent passage 4047 and a second vent passage 4048.

Although described as being in a particular order or defining a passage through which a particular reagent can flow, any of the reagents described herein can be conveyed into the detection module 4800 via any of the reagent passages. Moreover, in some embodiments, two successive volumes of the same reagent can be conveyed into the detection module via two different reagent passages. For example, in some embodiments, a substrate reagent formulated to enhance, catalyze and/or promote the production of the signal OP1 from the detection reagent (e.g., similar to the reagent R2 described above) can be stored in two independent volumes. In use, a first volume of the substrate reagent can be conveyed into the detection module 4800 via the third reagent passage 4045 at a first time, and a second volume of the substrate reagent can be conveyed into the detection module 4800 via the fourth reagent passage 4046 at a second time.

The housing assembly 4001 includes the sample transfer manifold 4100, which provide both structural support and defines flow paths for various fluids that are conveyed within the device 4000. In particular, the sample transfer manifold 4100 includes a sample input portion 4102, a wash portion 4103, an elution portion 4104, and a reagent portion 4105. Details of each of these portions is discussed below in conjunction with the various modules of the device 4000.

The sample preparation module 4200 includes a sample input module 4170, a wash module 4210, an elution module 4260, a filter assembly 4230, and various fluidic conduits (e.g., tubes, lines, valves, etc.) connecting the various components. The device 4000 also includes the lysing module 4300, which, together with the sample preparation module 4200, performs the nucleic acid extraction according to any of the methods described herein. Thus, although the sample preparation module 4200, the sample input module 4170, and the inactivation module 4300 are described as separate modules, in other embodiments, the structure and function of the sample preparation module 4200 can be included within or performed by the inactivation module 4300 and/or the sample input module 4170, and vice-versa. Similarly stated, any of the sample input modules, sample preparation modules, inactivation modules and/or lysing modules described herein can include any of the structure and/or perform any of the functions of the other modules to perform any of the methods of sample preparation or nucleic acid extraction described herein. By eliminating the need for external sample preparation and a cumbersome instrument, the device 4000 is suitable for use within a point-of-care setting (e.g., doctor's office, pharmacy or the like) or at the user's home, and can receive any suitable biological sample S1. The biological sample S1 (and any of the input samples described herein) can be, for example, blood, urine, male urethral specimens, vaginal specimens, cervical swab specimens, and/or nasal swab specimens gathered using a commercially available sample collection kit.

Figure 59:
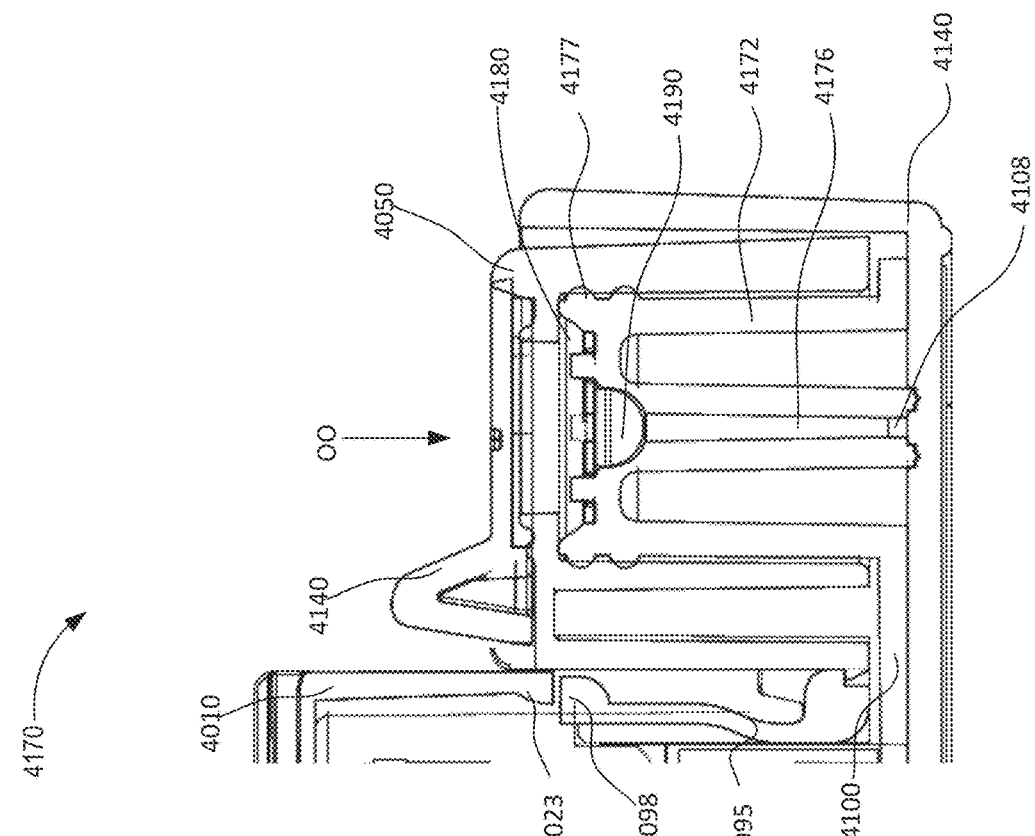
FIGS. 58 and 59 are cross-sectional views of a portion of the molecular diagnostic test device shown in FIGS. 10 and 11 with the sample input actuator in its second position taken along line $X_1$-$X_1$ in FIG. 55 and line $X_2$-$X_2$ in FIG. 57, respectively.
Figure 58:
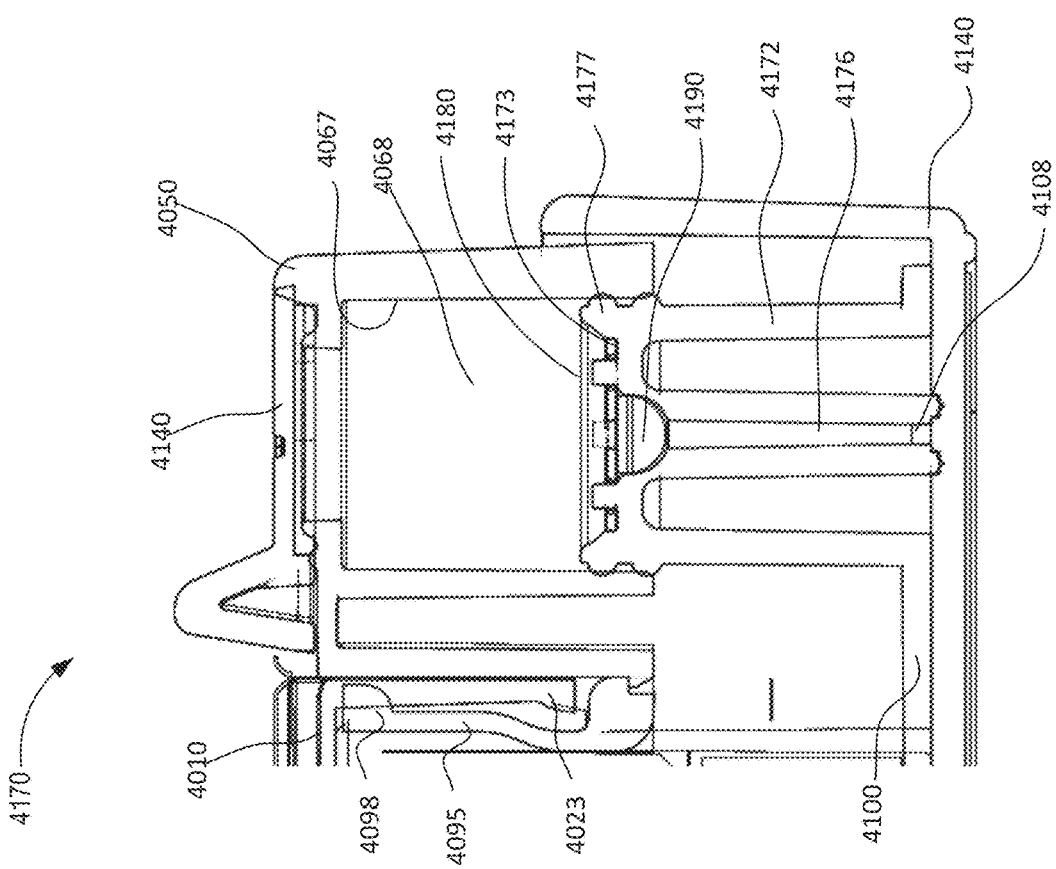

The sample input module 4170 is configured to receive a biological sample S1 containing a biological entity, and convey the biological sample toward the remaining elements of the sample preparation module 4200 (e.g., the filter assembly 4230). The biological sample S1 can be any of the sample types described herein, and the biological entity can be any of the entities described herein. The sample input module 4170 includes the sample input portion 4102 of the sample transfer manifold 4100, the sample input (or first) actuator 4050, and the lid 1140. Referring to FIGS. 21-26, the sample input portion 4102 of the sample transfer manifold 4100 includes a cylindrical housing 4172 and a cover 4180. As shown in FIGS. 58 and 59, the top surface of the cylindrical housing 4172 (including the top surface 4173 and/or portions of the cover 4180) and the inner surface 4067 of the first actuator 4050 define a sample input volume 4068, within which the biological sample is conveyed at the start of a test. The outer portion of the cylindrical housing 4172 includes one or more seals 4177 slidingly engage the inner surface 4067 of the first actuator 4050 to form a fluid-tight seal.

The cylindrical housing 4172 includes the top surface 4173 (see FIG. 26) that defines a reagent volume 4175 within which a lyophilized reagent 4190 is contained. In particular, the lyophilized bead 4190 is retained within the reagent volume 4175 by the cover 4180, which defines a series of openings. In this manner, the biological sample can be conveyed through the openings of the cover 4180 and into the reagent volume 4175 to mix with and reconstitute the lyophilized reagent 4190. Thus, the sample input module 4170 functions both to convey the sample into the device and also to ensure that the desired reagents are mixed into the biological sample.

The lyophilized reagent 4190 can be any of the reagents described herein. In some embodiments, the lyophilized reagent 4190 can be a positive control organism, such as *Aliivibrio fischeri, N. subflava*, or any other suitable organism. Specifically, *Aliivibrio fischeri* is suitable because it is gram negative, nonpathogenic, bio safety level 1, not harmful to the environment, and is extremely unlikely to be found on a human. The positive control surface within the detection module contains capture probes for both the control organism (e.g., *A. fischeri*) as well as each of the target organisms. This arrangement ensures that the positive control surface always produces color if the device functions correctly. If only the control organism were present, a very strong positive for one of the target organisms could "swamp out" or "outcompete" the amplification of the control organism during PCR. Under such circumstances, the positive control spot would not produce a color change which would be confusing for the user. This arrangement facilitates the detection method and the device 4000 being operated by a user with minimal (or no) scientific training, in accordance with methods that require little judgment.

Figure 25:
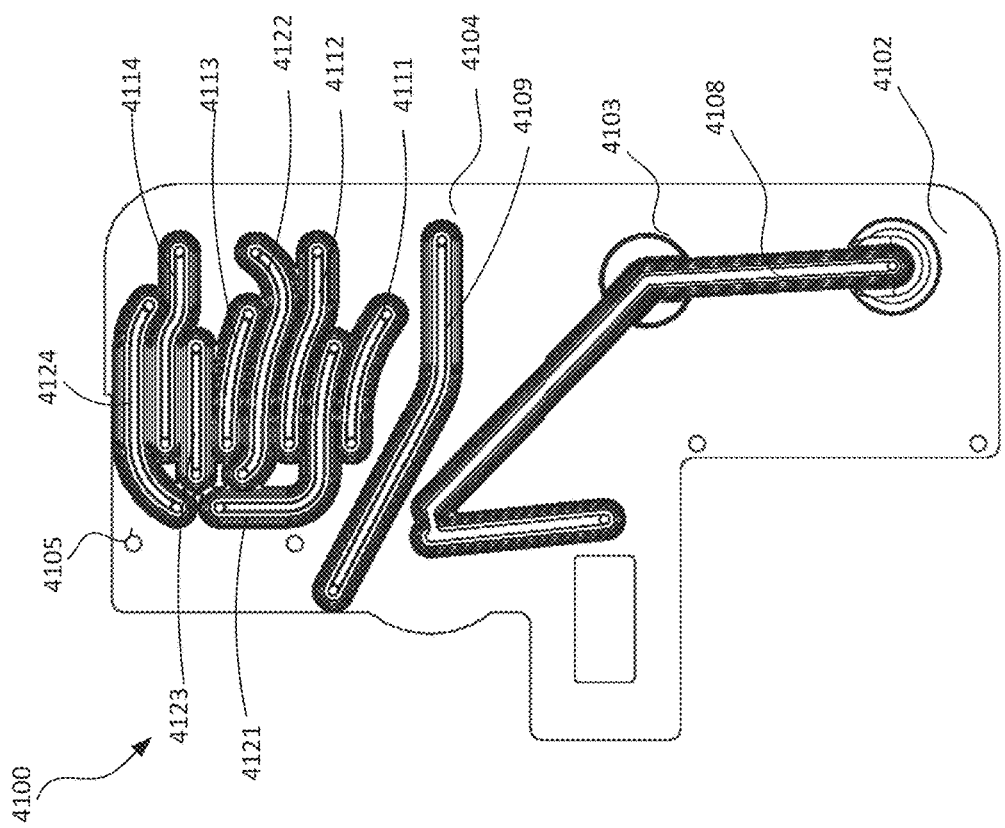
Figure 24:
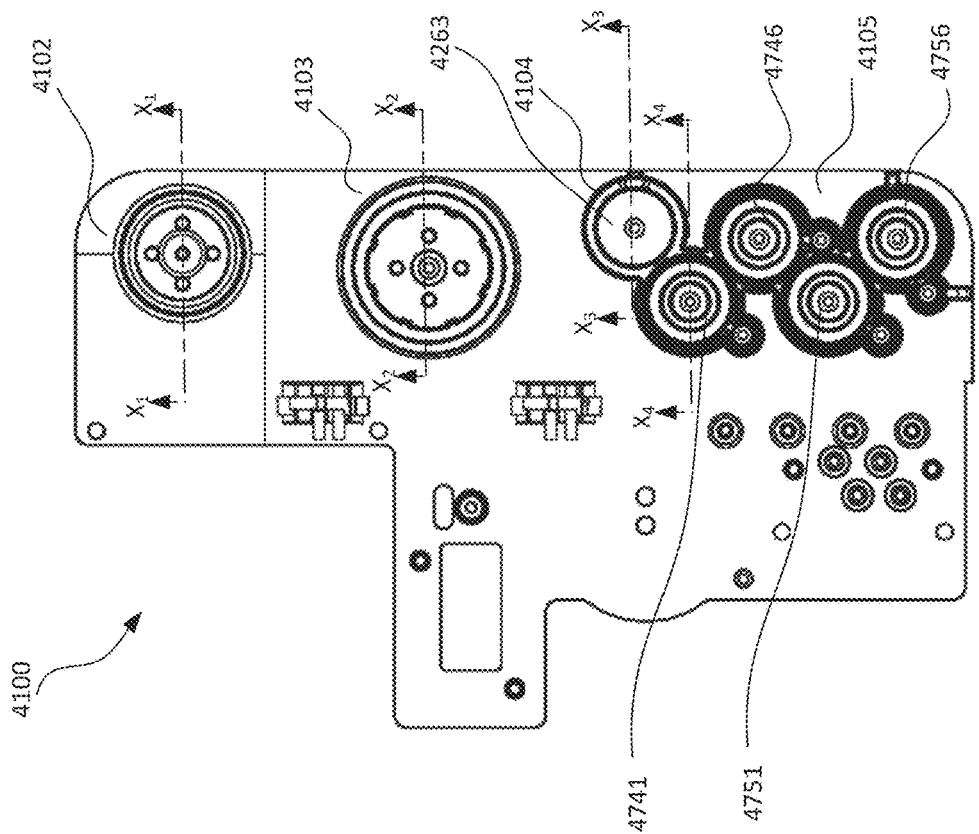
Figure 26:
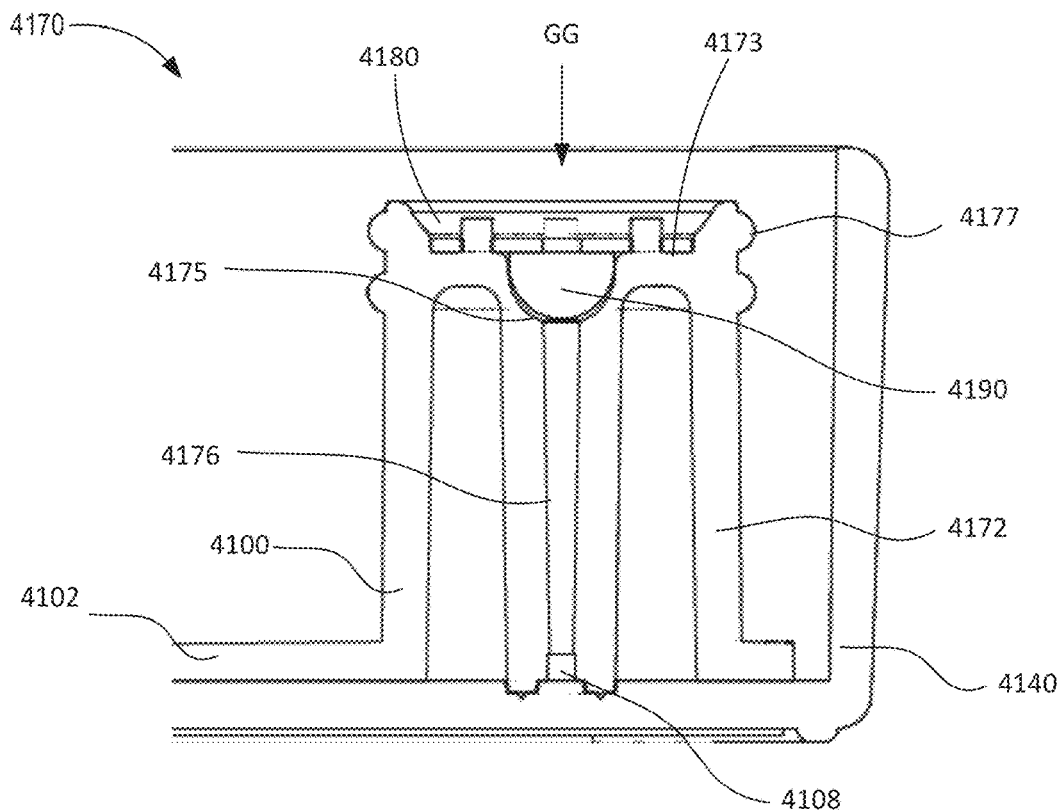
FIGS. 26-29 are cross-sectional views of the sample transfer manifold shown in FIGS. 22-25 taken along line $X_1$-$X_1$, $X_2$-$X_2$, $X_3$-$X_3$, and $X_4$-$X_4$, respectively.

The cylindrical housing 4172 defines a first (or vertical) fluid passage 4176 that is between (and fluid communication with) a sample input passage 4108 defined by the sample transfer manifold 4100 (see also FIG. 25, which shows the various fluid passages). The sample input passage 4108 is in fluid communication with the wash module 4210 and the filter assembly 4230. In this manner, when the biological sample is compressed by the first actuator 4050 it is conveyed from the sample input volume 4068, through the reagent volume 4175, through the first fluid passage 4176 and into the sample input passage 4108, as shown by the arrow GG in FIG. 26. In some embodiments, the sample is conveyed in this manner to the filter assembly 4230.

Figure 30:
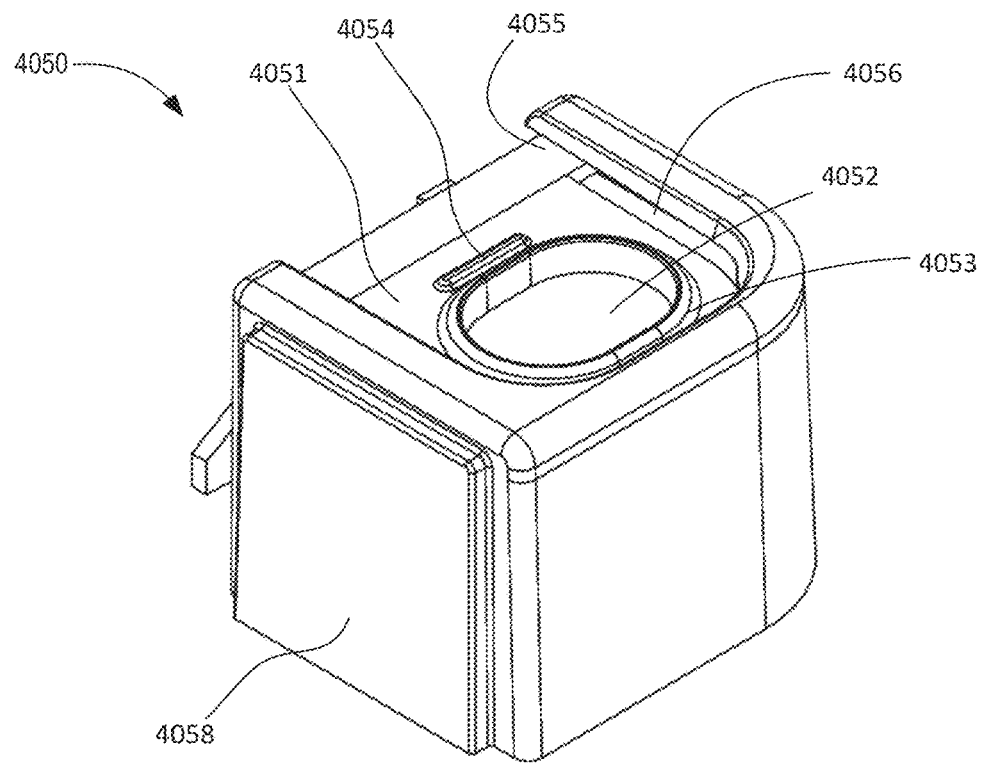
FIGS. 30-32 are a top perspective view, a bottom perspective view, and a side perspective view, respectively, of a sample input actuator of the molecular diagnostic test device shown in FIGS. 10 and 11.
Figure 31:
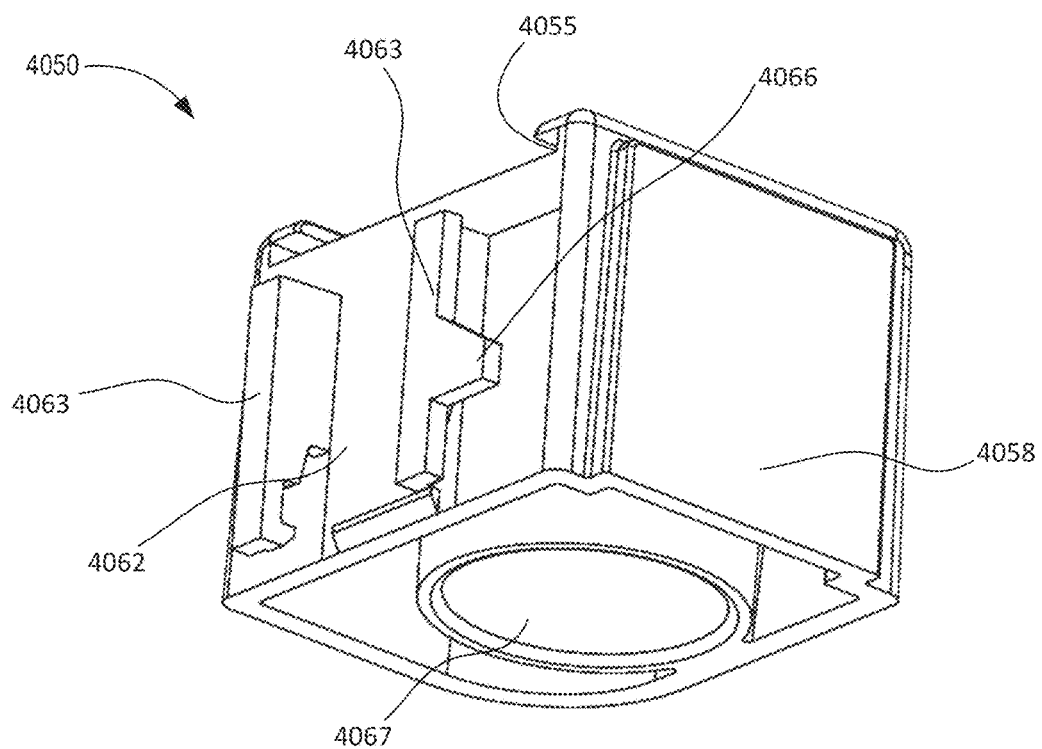
Figure 32:
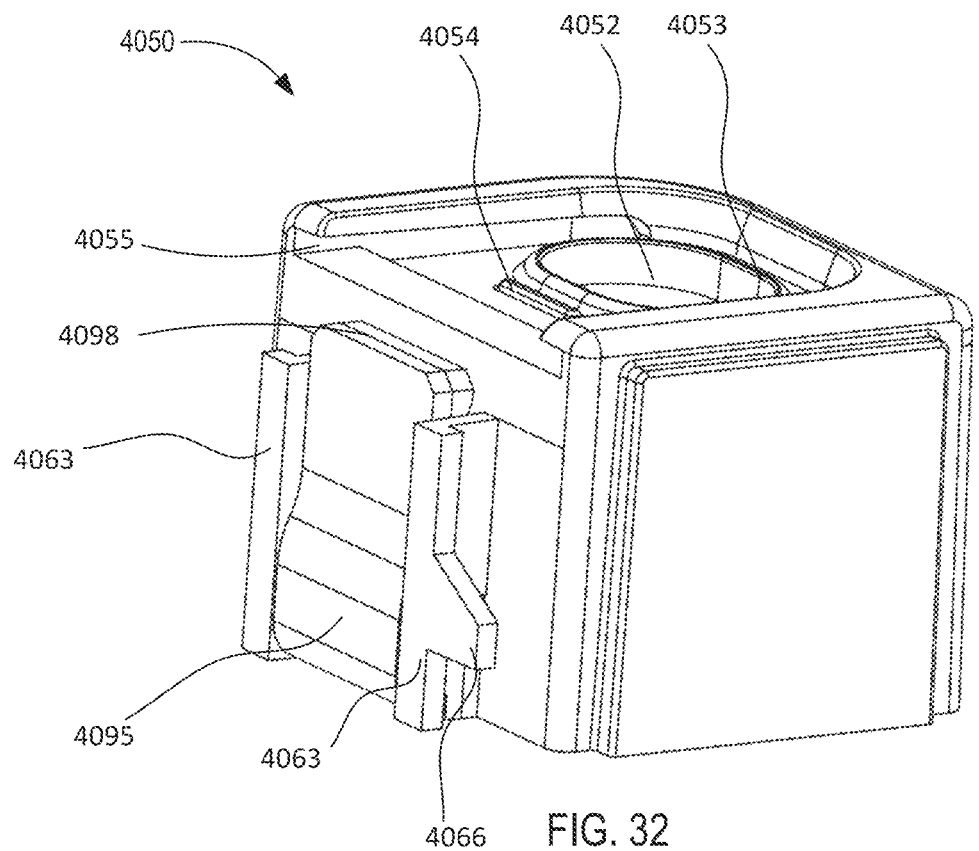

Referring to FIGS. 30-32, the sample input (or first) actuator 4050 includes a top surface 4051, a side surface 4058, a back surface 4062, and an inner surface 4067. The top surface 4051 defines an opening 4052 into the sample input volume 4068. The top surface 4051 also includes a seal 4053 surrounding the opening 4052. In this manner, when the lid 4140 is in its first lid position (opened), the biological sample can be conveyed through the opening 4052 and into the sample input volume 4068. The lid 4140 can then be sealed about the opening. The seal 4053 can be an elastomeric seal, such as an O-ring or the like, and can produce a substantially fluid-tight seal to protect against spilling or leaking during the test. The seal 4053 also fluidically isolates the sample input volume 4068 such that the pressure generated therein can be maintained to convey the biological sample through the passage 4108 (rather than leaking out via the opening 4052).

The top surface 4051 includes a protrusion 4054 and defines two side slots 4055 and two lock openings 4056. The protrusion 4054 is in contact with the end of the lid 4140 when the lid 4140 is in its opened position. In this manner, the protrusion 4054 acts as a detent to limit movement of the lid 4140 from its opened position (FIG. 10) to its closed position (FIG. 52). Similarly stated, the protrusion 4054 can offer resistance against the movement of the lid 4140 towards the second (or closed) position, thereby limiting the likelihood that a user will inadvertently close the lid 4140 before desired.

The side slots 4055 are aligned with the channels 4005 of the top housing 4010, and slidably receive the rails (also referred to as protrusions) 4145 of the lid 4140. In particular, when the lid 4140 is moved from the first lid position (opened) to the second lid position (closed), the rails 4145 move from the channels 4005 and into the side slots 4055 of the first actuator 4050. When the lid 4140 is in the opened position, because the rails 4145 are disengaged from the top housing 4010, the lid 4140 (and therefore the first actuator 4050) are free to move relative to the top housing 4050. Said another way, when the lid 4140 is in the closed position, the lid 4140 is sealed about the opening 4052 and the first actuator 4050 can be moved from its first position to its second position. The two lock openings 4056 are "through openings" beneath two side slots 4055, and define a volume within which the lock portions 4146 of the lid 4140 can expand (or deform) when the lid 4140 is in the closed position (see FIG. 53). In this manner, the lock portions 4146 engage a shoulder that borders the two lock openings 4056 to prevent the lid 4140 from being moved from its closed position back towards its opened position.

The side surface 4058 includes a raised surface that matingly engages with a side surface 4059 of the second (wash) actuator 4070. In this manner, when the second actuator 4070 is moved to its second position, the side surface 4058 of the first actuator 4050 guides the movement of the second actuator 4070. As described above, the inner surface 4067 defines a portion of a boundary of the sample input volume 4068.

Figure 40:
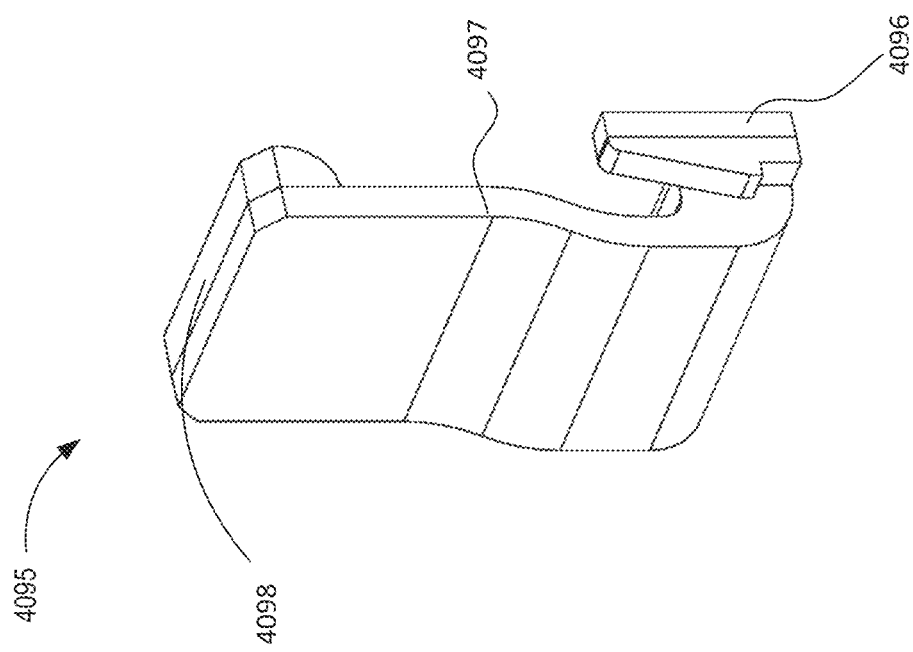
FIG. 40 is a perspective view of a spring clip that can be coupled to the sample input actuator, as shown in FIG. 32.
Figure 43:
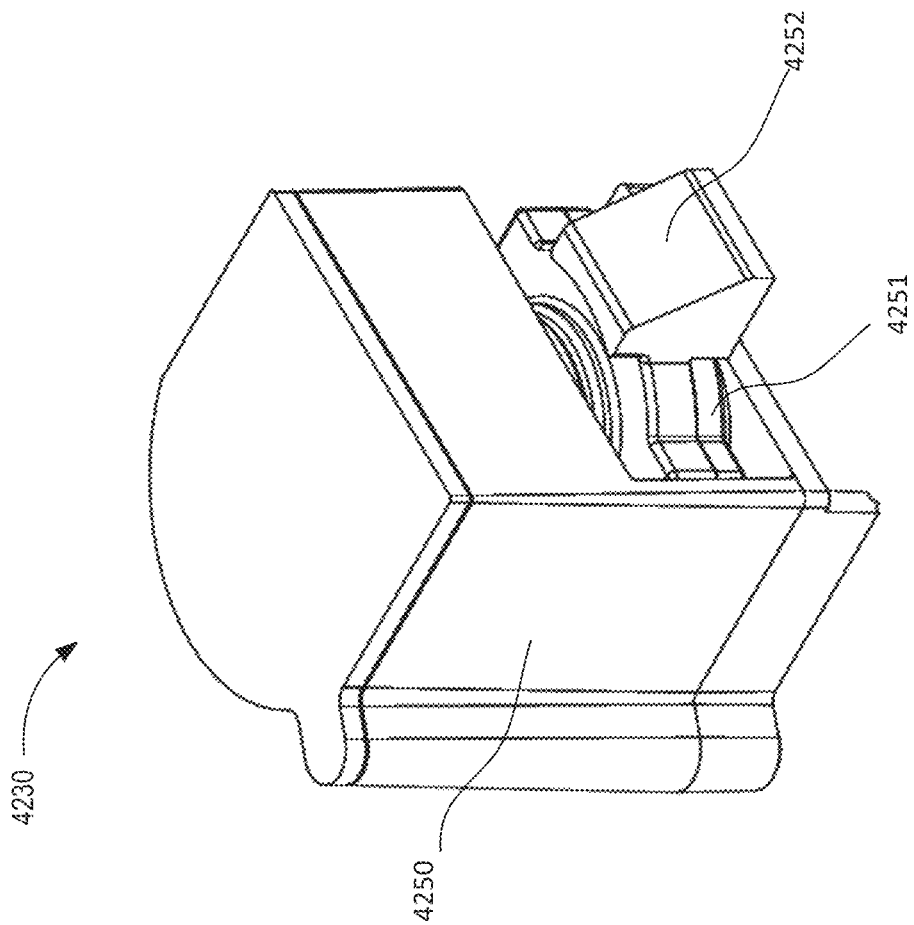
FIGS. 43 and 44 are a perspective view and a top view, respectively, of a filter assembly of the molecular diagnostic test device shown in FIGS. 10 and 11.
Figure 42:
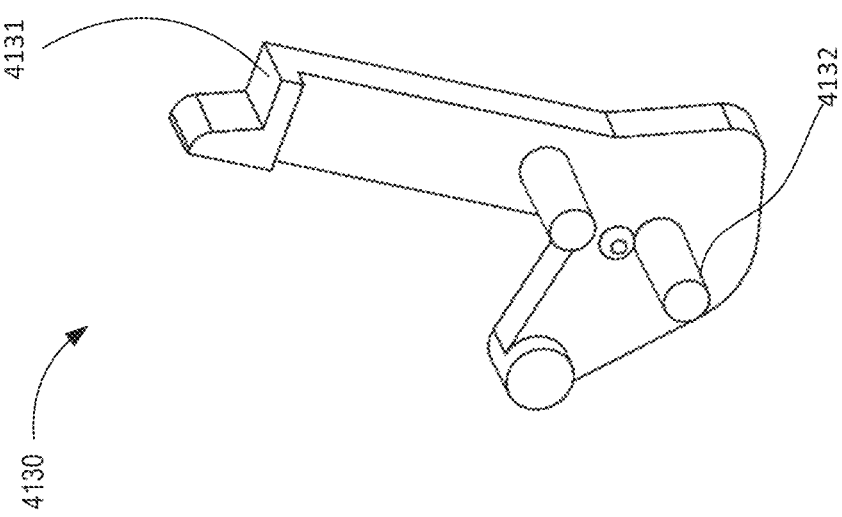
Figure 44:
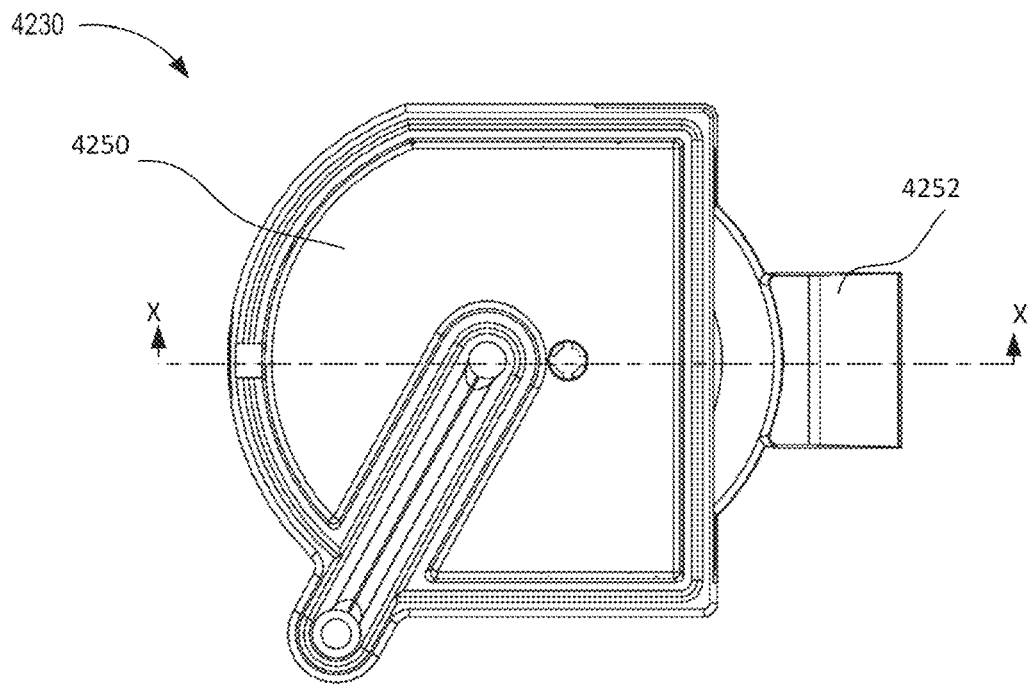
Figure 45:
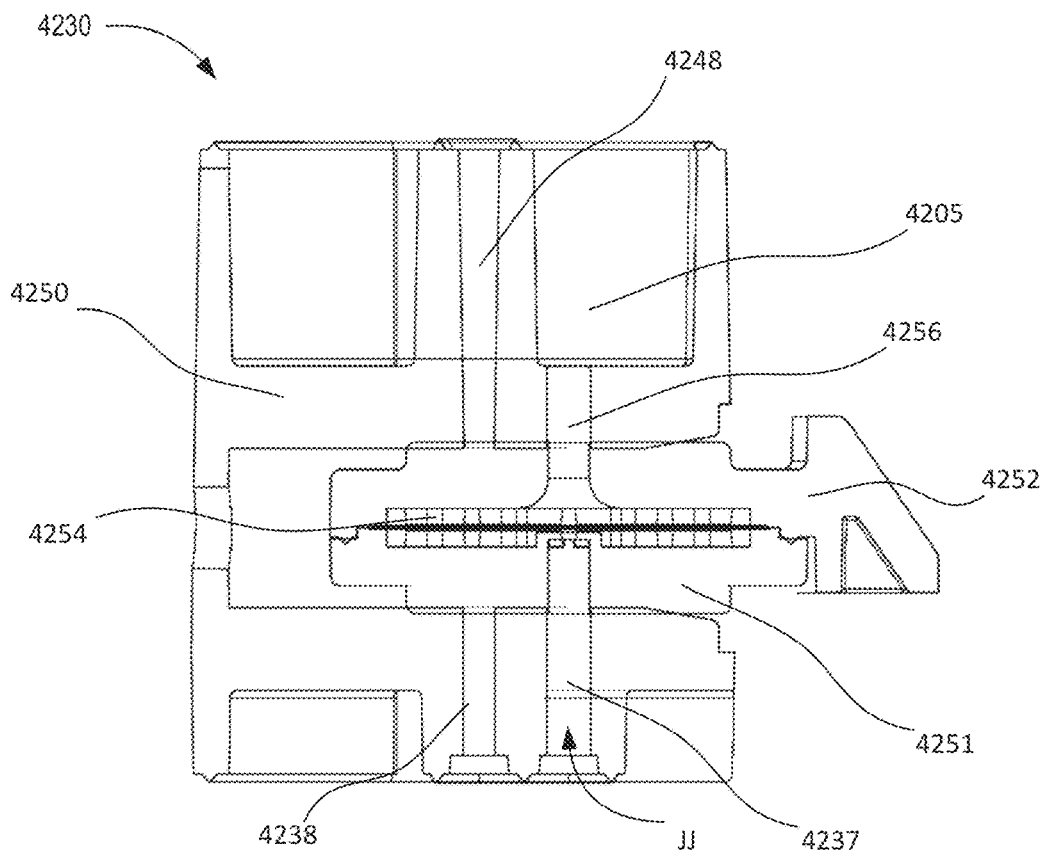
FIGS. 45 and 46 are cross-sectional views of the filter assembly shown in FIGS. 43 and 44 taken along line X-X in FIG. 44, with the filter assembly in a first configuration and a second configuration, respectively.

The back surface 4062 includes a pair of mounting protrusions 4063. The mounting protrusions 4063 are received within the actuator guide slots 4022, as described above. Additionally, the mounting protrusions 4063 each include a connection portion that is connected to the base 4096 of the spring clip 4095 (see FIGS. 32 and 40). In particular, the spring clip 4095 is coupled to the mounting protrusions 4063 such that when the first actuator 4050 is in its first position, the lock protrusion 4023 of the housing (i.e., between the two actuator guide slots 4022) is between the spring clip 4095 and the back surface 4062 (see FIG. 58). As shown in FIG. 40, the spring clip 4095 includes a resilient portion 4097 that biases the lock portion 4098 of the spring clip 4095 against the lock protrusion 4023. As shown in FIG. 59, when the first actuator 4050 is moved to its second (or actuated) position, the lock portion 4098 becomes disengaged with the lock protrusion 4023 of the housing, and contacts the back surface 4062 of the first actuator 4050. In this manner, the lock portion 4098 will engage the shoulder of the lock protrusion 4023 if the first actuator 4050 is moved back towards its first position. In this manner, the first actuator 4050 is retained in its second position.

As shown in FIG. 31, the inboard mounting protrusion 4063 (i.e., the protrusion adjacent the second actuator 4070) includes an actuation protrusion 4066. As described in more detail below, the actuation protrusion 4066 is configured to contact the reagent lock 4130 that is in contact with the second actuator 4070 (see FIGS. 55 and 57). When the first actuator 4050 is in its first position, the reagent lock 4130 is in contact with the second actuator 4070, thereby preventing the second actuator 4070 from being moved. When the first actuator 4050 moves from its first position (FIG. 55) to its second position (FIG. 57), the actuation protrusion 4066 causes the reagent lock 4130 to rotate as shown by the arrow PP in FIG. 57 to release the reagent lock 4130 from the second actuator 4070. In this manner, the second actuator 4070 cannot be depressed (or moved) before the first actuator 4050 is moved to its second (or actuated) position.

Figure 33:
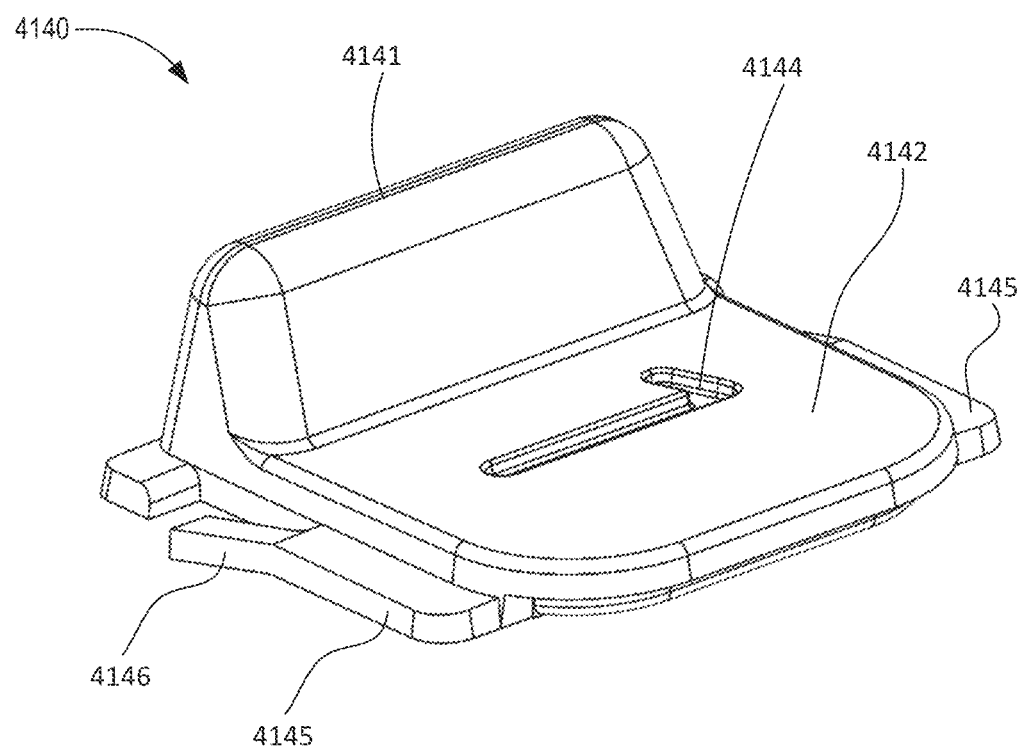
FIGS. 33 and 34 are a top perspective view and a bottom perspective view, respectively, of a sample lid of the molecular diagnostic test device shown in FIGS. 10 and 11.
Figure 34:
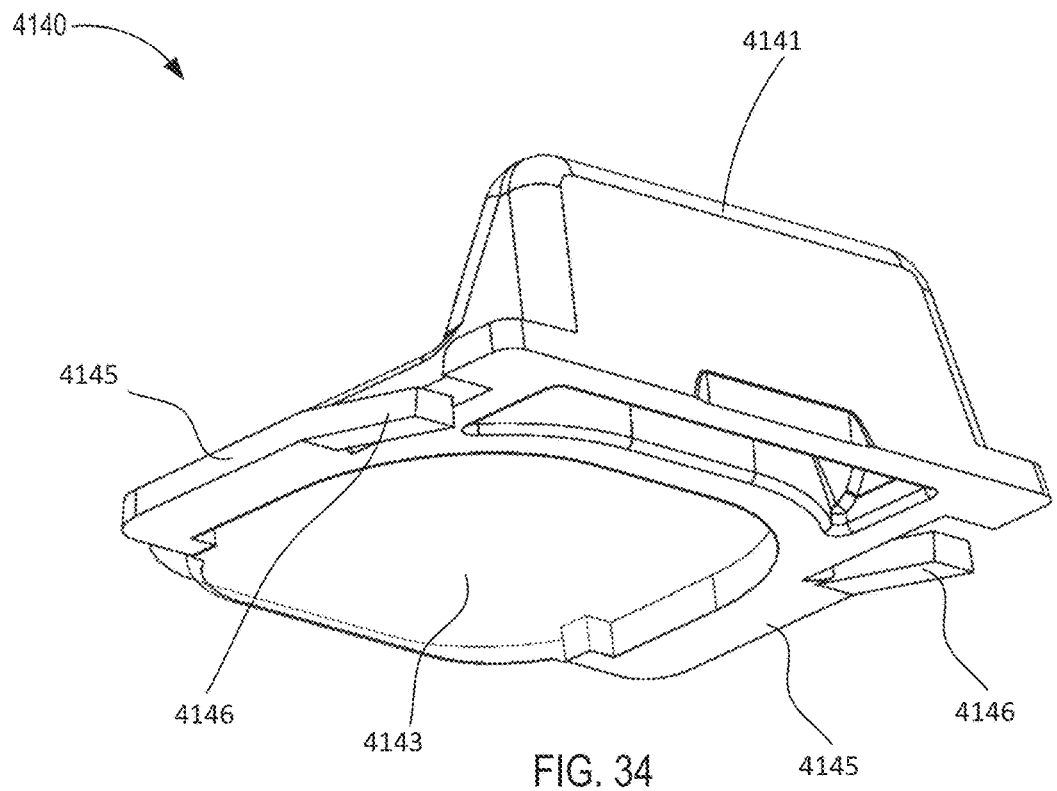

As shown in FIGS. 33 and 34, the lid 4140 includes a top portion 4141, a cover portion 4142, and a pair of side rails 4145. The top portion 4141 extends above the surface of the top housing 4010 and can be manipulated or grasped by the user to move the lid 4140 from the first lid position to the second lid position. The cover portion 4142 includes an indicator 4144 (i.e., "1") to guide a user in the correct sequence of steps for use of the apparatus 4000. The bottom surface 4143 (or seal surface 4143) of the cover portion 4142 engages the seal 4053 when the lid 4140 is in the closed position to produce a substantially fluid-tight seal to protect against spilling or leaking during the test. As describe above the side rails 4145 each include a lock portion 4146. The lock portions 4146 are deformed when the lid 4140 is in its opened position such that the side rails 4145, including the lock portions 4146, are within the channels 4005 of the top housing 4010. When the lid 4140 is moved to the closed position, the lock portions 4146 expand or deform to their natural condition (as shown) and extend within the two lock openings 4056 to prevent the lid 4140 from being moved from its closed position back towards its opened position (see FIG. 53).

The wash module 4210 is configured to convey a wash solution toward the remaining elements of the sample preparation module 4200 (e.g., the filter assembly 4230). Importantly, as described herein, the wash module 4210 is configured such that it cannot be actuated out of the desired sequence of operations. Specifically, the wash module 4210 is configured to be locked until after the biological sample has been conveyed to the sample preparation module 4200. The wash module 4210 includes the wash portion 4103 of the sample transfer manifold 4100, the wash (or second) actuator 4070, and a wash container 4220. Referring to FIGS. 21-25, and 27, the wash portion 4103 of the sample transfer manifold 4100 includes a cylindrical housing 4211 and a top surface (or cover) 4123.

Figure 27:
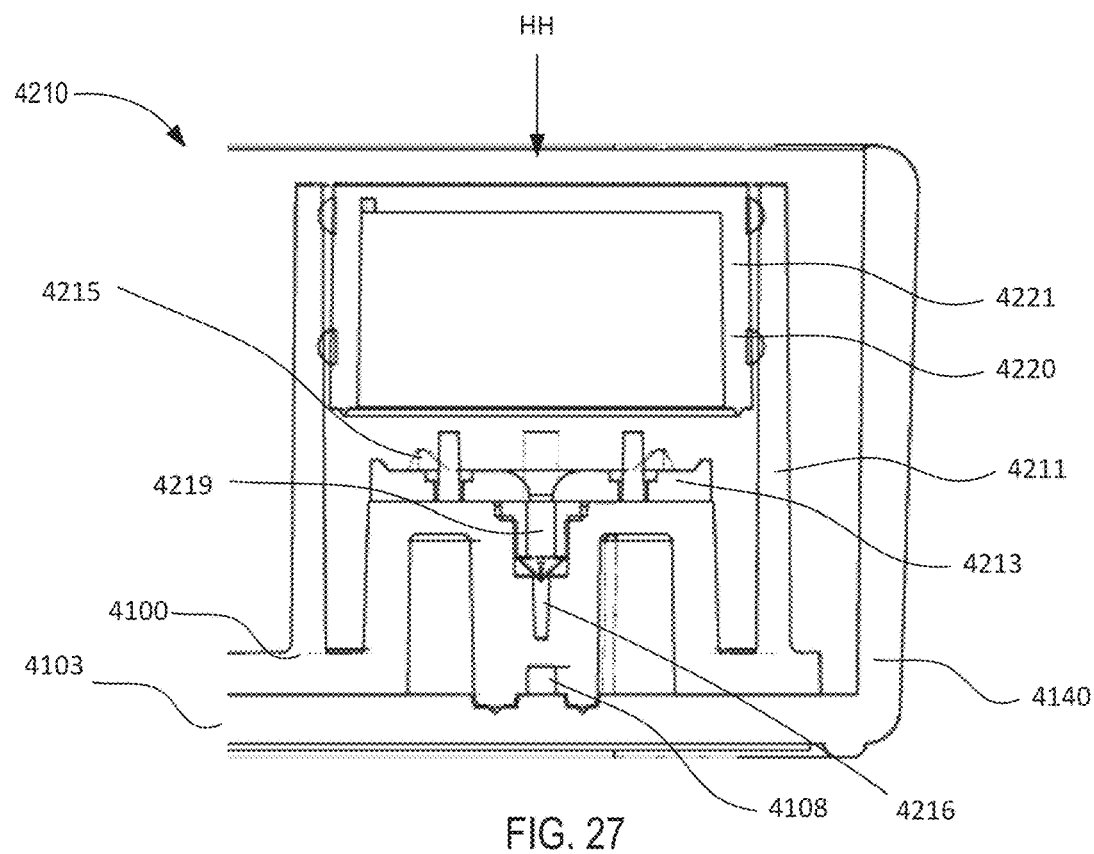

The upper portion of the cylindrical housing 4211 defines a volume 4212 within which the wash container 4220 is disposed. As shown in FIG. 27, the wash container 4220 includes a side wall 4221 that is sealingly engaged with in inner side wall of the cylindrical housing 4211. The wash container 4220 can include any number of seals (e.g., O-rings, gaskets, or the like) to fluidically isolate the volume 4212 from the external volume of the device 4000. In this manner, the sealed wash container 4220 can limit backflow of the wash solution out of the device 4000. The lower portion of the wash container 4220 is sealed with a frangible member to define a sealed container suitable for long-term storage of the wash solution. As described below, the frangible seals are punctured upon actuation of the wash module 4210 allow the wash solution within the container 4220 to be conveyed to the filter assembly 4230. The frangible seals can be, for example, a heat-sealed BOPP film (or any other suitable thermoplastic film). Such films have excellent barrier properties, which prevent interaction between the fluids within the canister and external humidity, but also have weak structural properties, allowing the films to be easily broken when needed.

The wash solution within the wash container 4220 can be any suitable solution. In some embodiments, the wash solution is preceded by the trapped air between the frangible seal and the cover 4123. By including a gas (or air) wash, the amount of liquid constituents from the input sample and wash solution (within the container 4220) conveyed to the filter assembly 4230 can be reduced. Said another way, after delivery of the input sample to the filter assembly 4230 by actuation of the sample input module 4170, the filter assembly 4230 will retain the desired sample cells and some amount of residual liquid. By forcing the first, gaseous wash composition through the filter (i.e., an "air wash"), the amount of residual liquid can be minimized. This arrangement can reduce the amount of liquid wash (e.g., the wash composition within the wash container 4220) needed to sufficiently prepare the sample particles. Reducing the liquid volume contributes to the reduction size of the device 4000 and also reduces the likelihood of potentially harmful shearing stress when the liquid wash is flowed through the filter assembly.

The lower portion of the cylindrical housing 4211 defines a second (or vertical) fluid passage 4216 that is between (and fluid communication with) the sample input passage 4108. A check valve 4219 is included within the second passage 4216, and is retained in place by the cover 4123. The check valve 4219 prevents backflow from the sample input passage 4108 upward into the volume 4212 (i.e., in a direction opposite the direction shown by arrow HH). The cover 4123 also includes a series of puncturers 4215 (only one is identified in FIG. 27). In use, when the wash container 4220 is moved downward (in the direction shown by the arrow HH), the puncturers rupture the frangible membrane to release the wash solution from within the wash container 4220. Moreover, the housing 4211 defines an annular groove or opening that receives the side wall of the wash container 4220 after it has been punctured and moved downward. In this manner, the dead volume produced by the interface between the wash container 4220 and the housing 4211 is minimized.

As described above, the sample input passage 4108 extends from the sample input module 4170 to the wash module 4210, and on to the filter assembly 4230. In this manner, after the biological sample is conveyed from the sample input volume 4068 to the filter assembly 4230, the wash solution (described herein) can be conveyed along a portion of the same path (the sample input passage 4108) to the filter assembly 4230. Specifically, the wash solution can be conveyed from the wash container 4220 and through the second fluid passage 4216, as shown by the arrow HH in FIG. 27.

Figure 35:
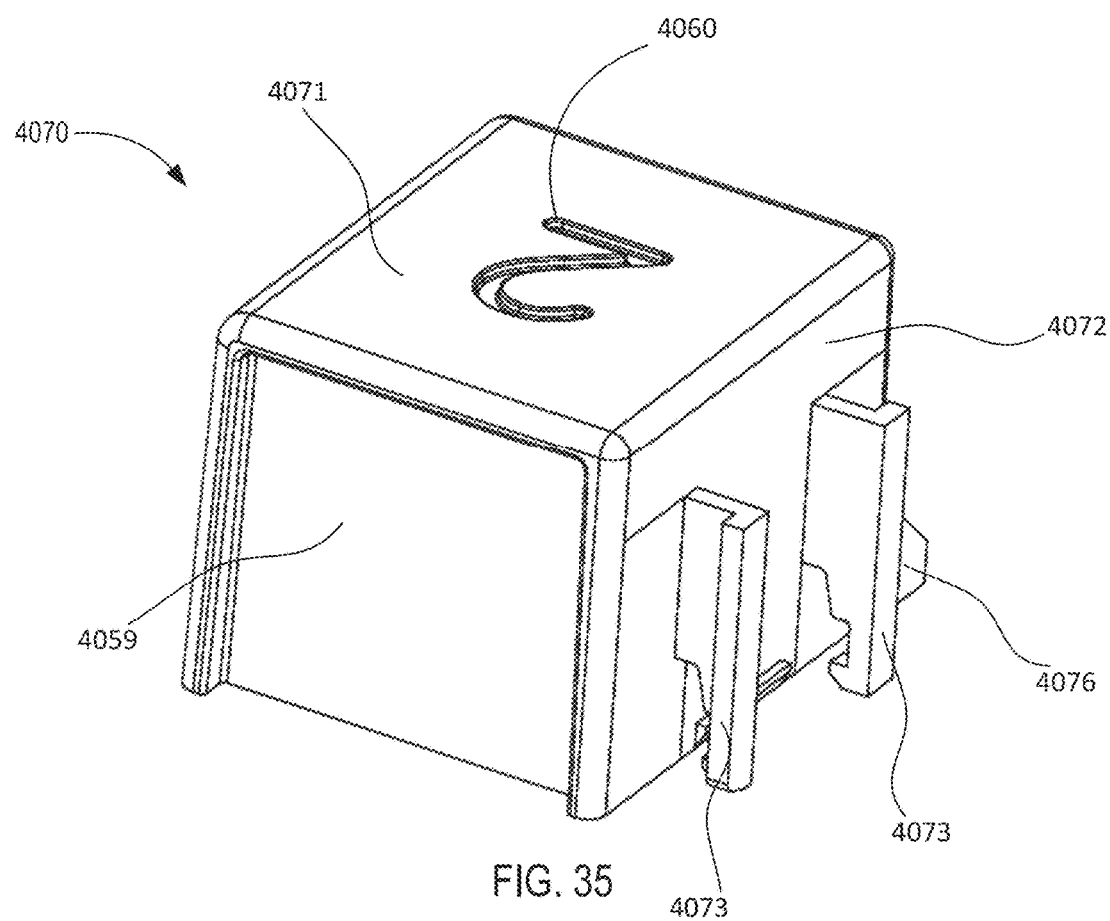
FIGS. 35-37 are a side perspective view, a bottom perspective view, and a rear perspective view, respectively, of a first reagent actuator of the molecular diagnostic test device shown in FIGS. 10 and 11.
Figure 36:
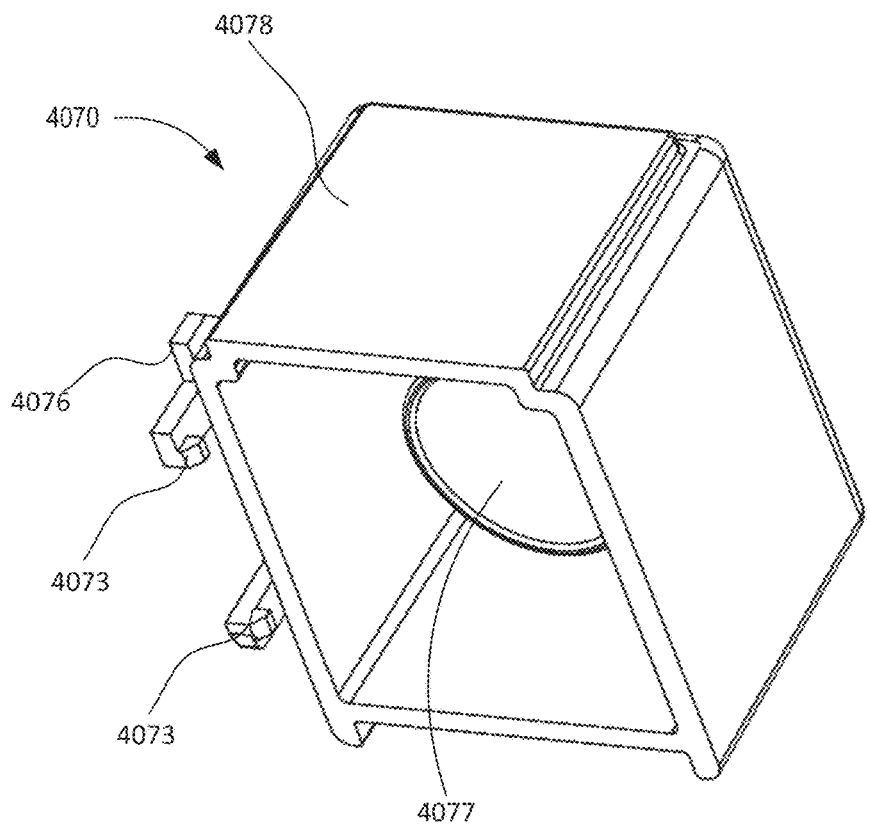
Figure 37:
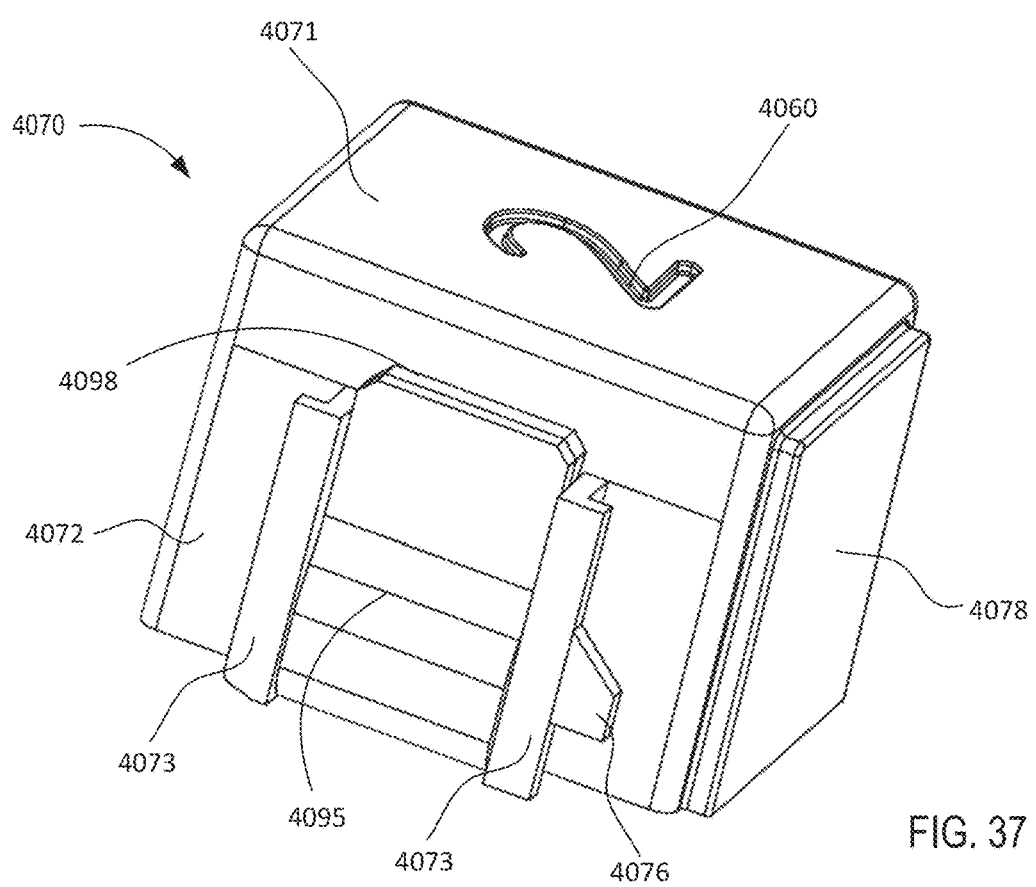

The wash module 4210 is actuated by the wash (or second) actuator 4070. Referring to FIGS. 35-37, the wash (or second) actuator 4070 includes a top surface 4071, a first side surface 4059, a second side surface 4078, a back surface 4072, and an inner surface 4077. The top surface 4071 includes an indicator 4060 (i.e., "2") to guide a user in the correct sequence of steps for use of the apparatus 4000. The first side surface 4059 includes a recessed area that matingly engages with the side surface 4058 of the first actuator 4050. In this manner, when the second actuator 4070 is moved to its second position, the side surface 4058 of the first actuator 4050 guides the movement of the second actuator 4070. The second side surface 4078 includes a raised surface that matingly engages with a side surface 4090 of the third (reagent) actuator 4080. In this manner, when the third actuator 4080 is moved to its second position, the side surface 4078 of the second actuator 4070 guides the movement of the third actuator 4080. The inner surface 4077 includes a protrusion that engages the side wall of the wash container 4220 and moves the wash container 4220 against the puncturers 4215, as described herein.

The back surface 4072 includes a pair of mounting protrusions 4073. The mounting protrusions 4073 are received within the actuator guide slots 4026. Additionally, the mounting protrusions 4073 each include a connection portion that is connected to the base 4096 of the spring clip 4095 (see FIGS. 37 and 40). In particular, the spring clip 4095 is coupled to the mounting protrusions 4073 such that when the second actuator 4070 is in its first position, the lock protrusion 4027 of the housing (i.e., between the two actuator guide slots 4026) is between the spring clip 4095 and the back surface 4072 (similar to the arrangement shown in FIG. 58). As shown in FIG. 40, the spring clip 4095 includes a resilient portion 4097 that biases the lock portion 4098 of the spring clip 4095 against the lock protrusion 4027. Similar to the arrangement shown in FIG. 59, when the second actuator 4070 is moved to its second (or actuated) position, the lock portion 4098 becomes disengaged with the lock protrusion 4027 of the housing, and contacts the back surface 4072 of the second actuator 4070. In this manner, the lock portion 4098 will engage the shoulder of the lock protrusion 4027 if the second actuator 4070 is moved back towards its first position. In this manner, the second actuator 4070 is retained in its second position.

Figure 56:
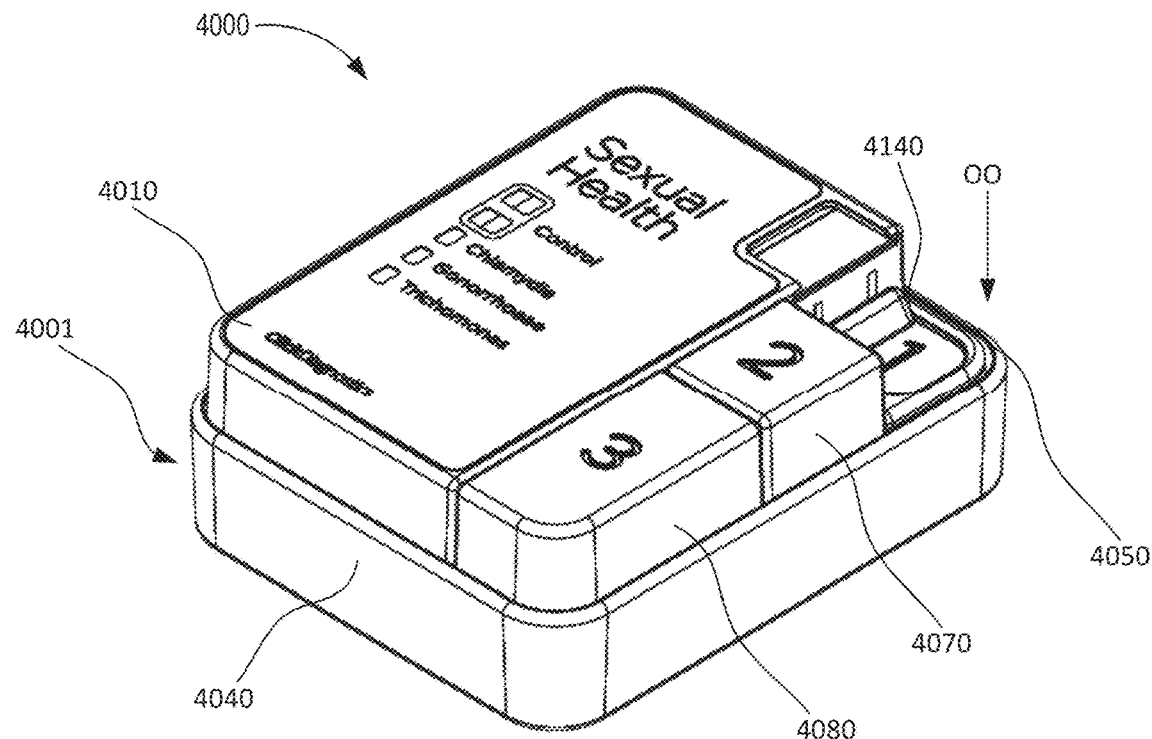
FIGS. 56 and 57 are a perspective view and a rear view, respectively, of the molecular diagnostic test device shown in FIGS. 10 and 11, showing the lid in the closed position and the sample input actuator in its second position.
Figure 60:
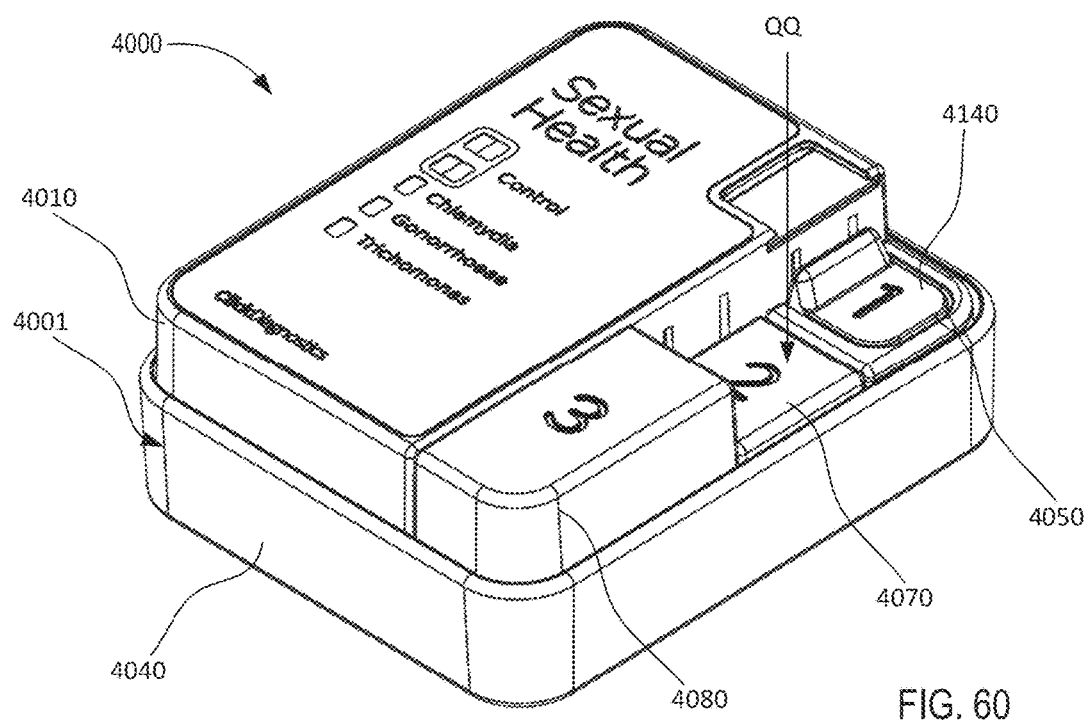
FIGS. 60 and 61 are a perspective view and a rear view, respectively, of the molecular diagnostic test device shown in FIGS. 10 and 11, showing the sample input actuator in its second position and the first reagent actuator in its second position.
Figure 61:
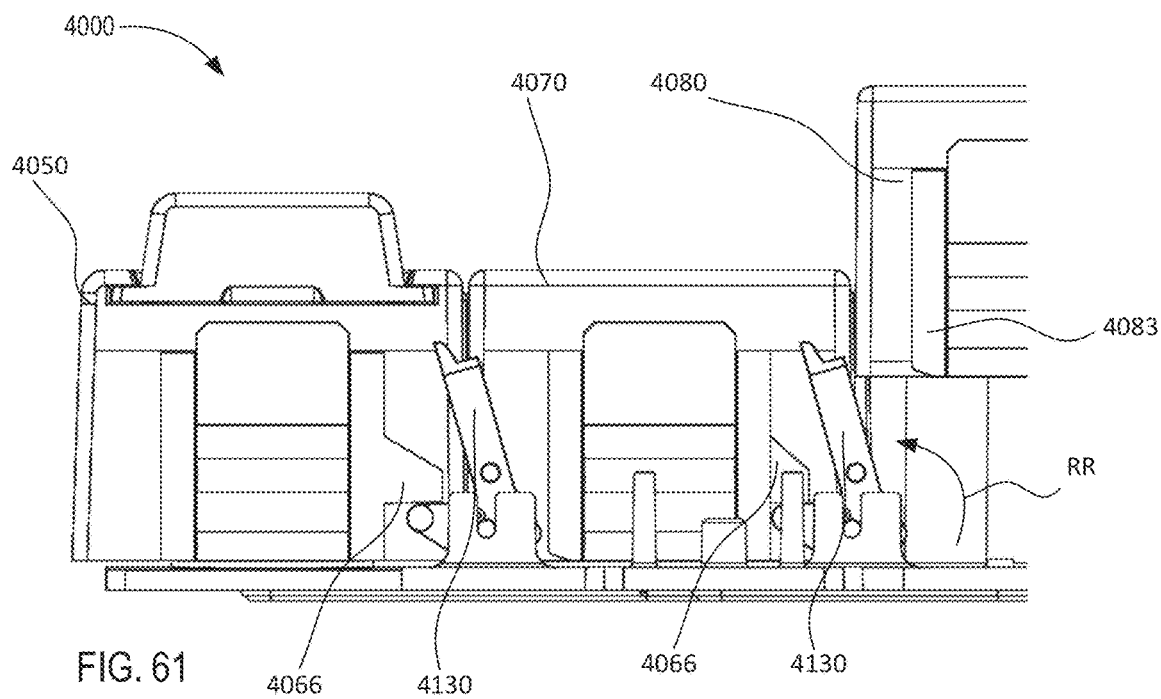

As shown in FIG. 37, the inboard mounting protrusion 4073 (i.e., the protrusion adjacent the third actuator 4080) includes an actuation protrusion 4076. As described in more detail below, the actuation protrusion 4076 is configured to contact the reagent lock 4130 that is in contact with the third actuator 4080 (see FIGS. 55 and 61). Thus, when the second actuator 4070 is in its first position, the reagent lock 4130 is in contact with the third actuator 4080, thereby preventing the third actuator 4080 from being moved. When the second actuator 4070 moves from its first position (FIG. 56) to its second position (FIG. 60), the actuation protrusion 4076 causes the reagent lock 4130 to rotate as shown by the arrow RR in FIG. 61 to release the reagent lock 4130 from the third actuator 4080. In this manner, the third actuator 4080 cannot be depressed (or moved) before the first actuator 4050 and the second actuator 4070 have both been actuated.

As described herein, the biological sample and the wash solution are conveyed through the filter assembly 4230. The filter assembly is configured to receive an elution buffer (via a backflush operation) to convey the desired particles (and the elution buffer) to the lysing module 4300. The filter assembly 4230 is shown in FIGS. 43-46. The filter assembly 4230 includes a filter housing 4250, a first plate 4251, a second plate 4252, and a filter membrane 4254. As described herein, the filter assembly 4230 is configured to filter and prepare the input sample (via the sample input operation and the sample wash operation), and to allow a back-flow elution operation to deliver captured particles from the filter membrane 4254 and deliver the eluted volume to the target destination (e.g., towards the amplification module 4600).

The filter housing 4250 contains the first plate 4251 and the second plate 4252, with the filter membrane 4254 disposed therebetween. As described herein, the second plate 4252 can move relative to the first plate 4251 to allow the filter to toggle between various flow conditions. The filter housing 4250 defines a sample inlet port 4237, a sample outlet port 4238, an elution inlet port 4248, and a waste reservoir 4205. The sample inlet port 4237 allows communication from the sample input passage 4108 and through the filter membrane 4254, as shown by the arrow JJ in FIG. 45. When the filter assembly 4230 is in its first configuration (i.e., the "sample flow" configuration, see FIG. 45), the flow port 4256 of the second plate 4252 is in fluid communication with the waste reservoir 4205. Thus, when the filter assembly 4230 is in its first configuration, the sample and wash solutions flow (towards the waste reservoir 4205), as indicated by the arrow JJ in FIG. 45.

Figure 46:
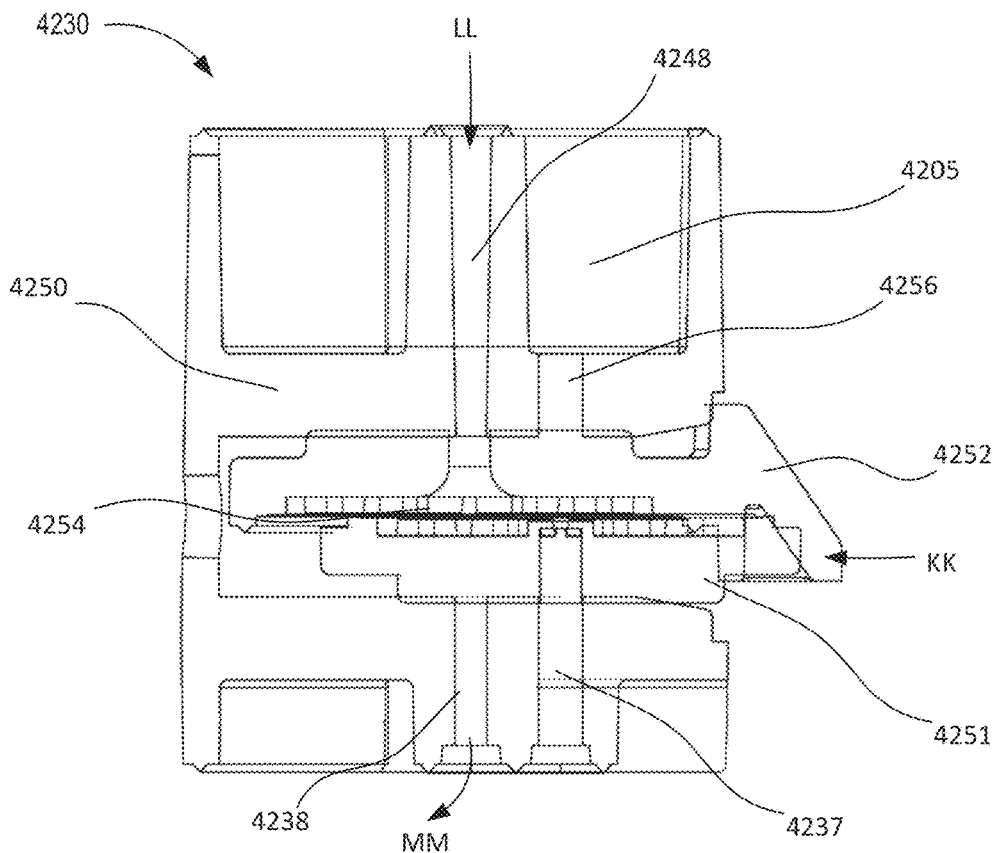
Figure 47:
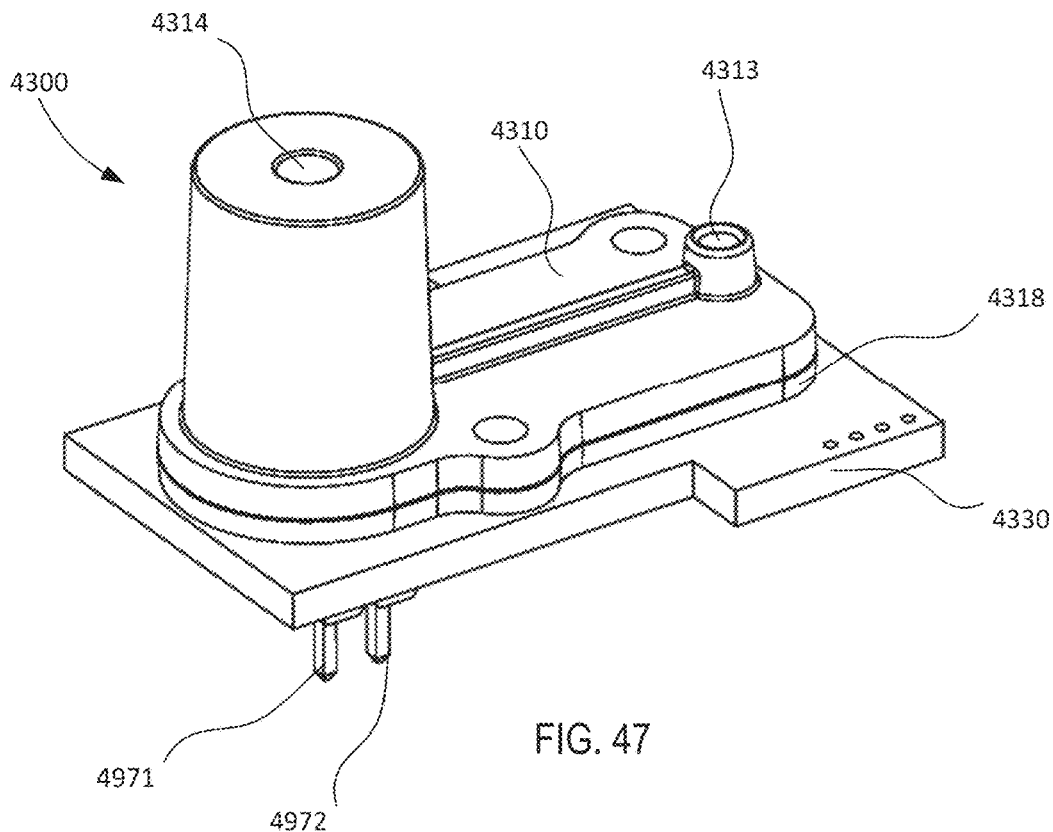
FIGS. 47-49 are a top perspective view, a bottom perspective view, and a bottom view, respectively, of a lysing module of the molecular diagnostic test device shown in FIGS. 10 and 11.
Figure 48:
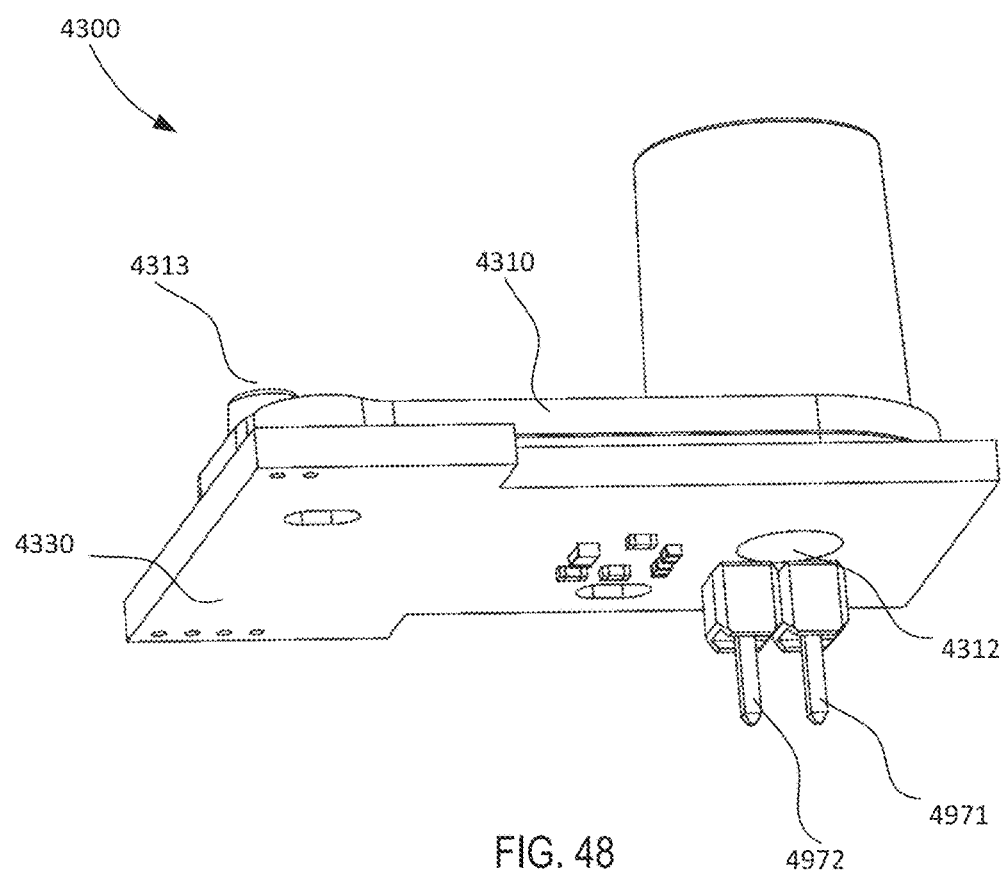
Figure 49:
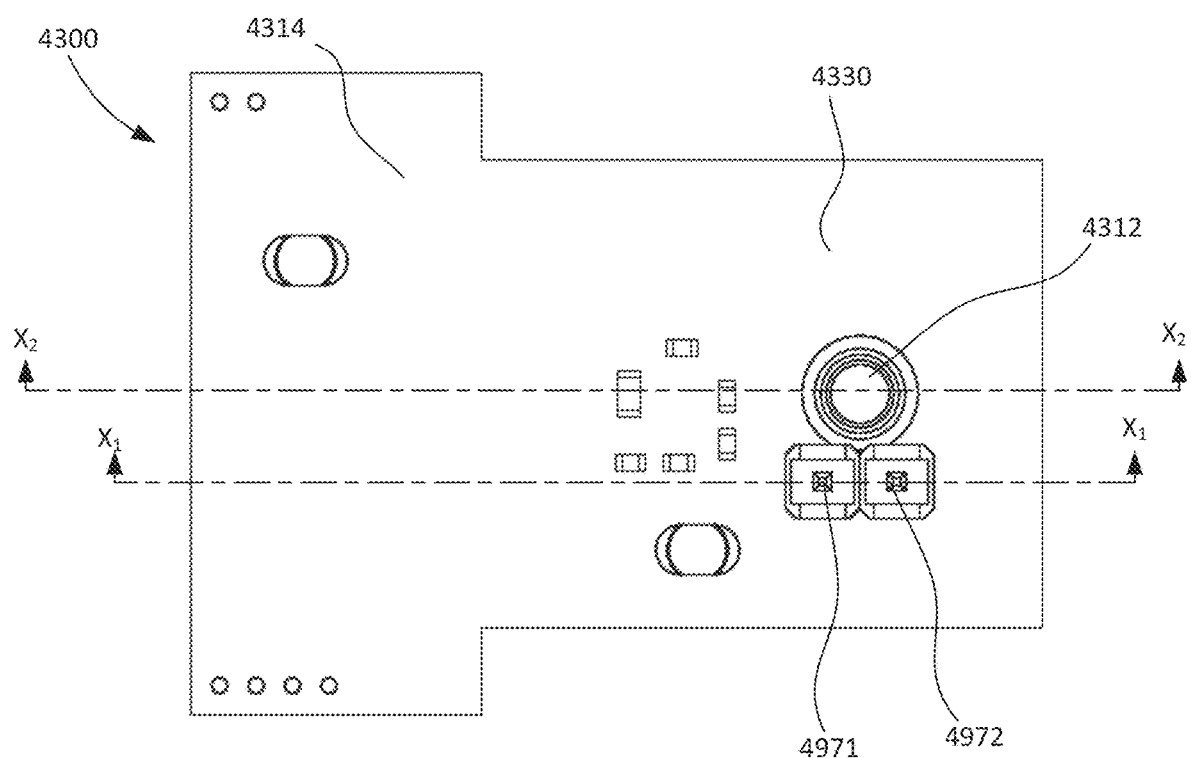
Figure 50:
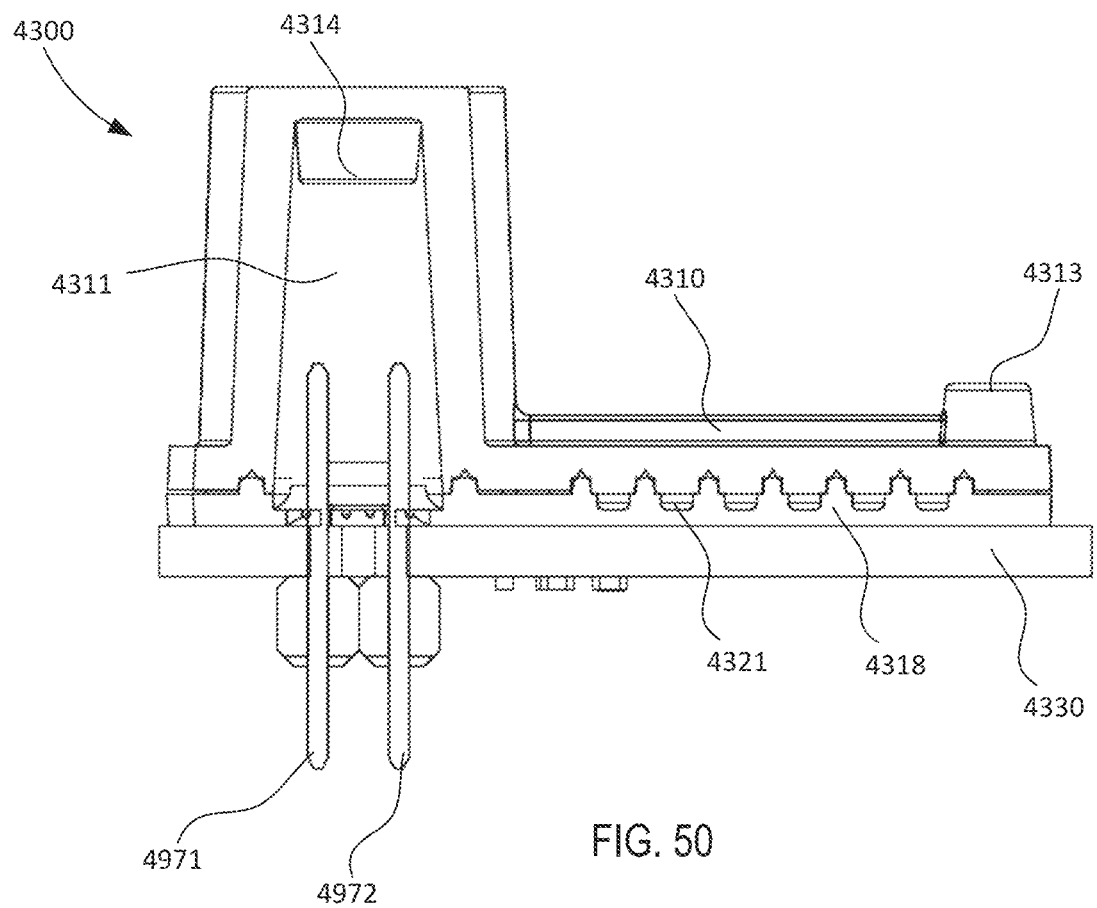
FIGS. 50 and 51 are cross-sectional views of the lysing module shown in FIGS. 47 and 48 taken along line $X_1$-$X_1$ and line $X_2$-$X_2$ in FIG. 49, respectively.
Figure 51:
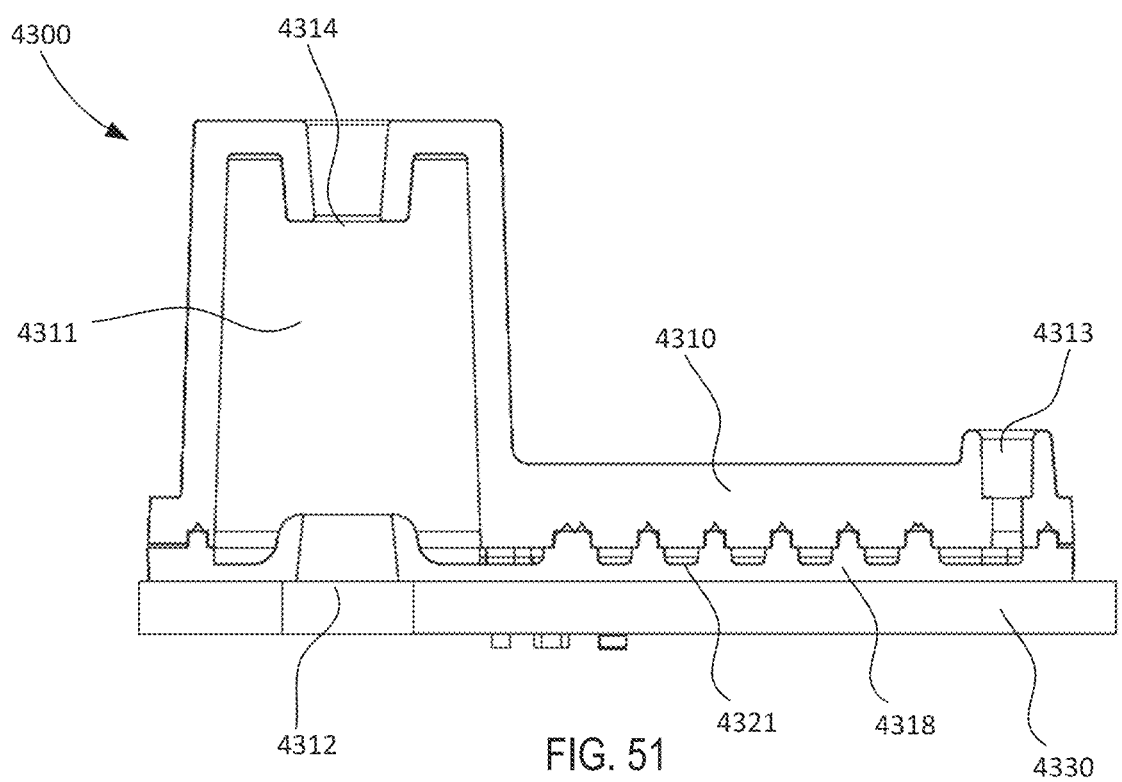
Figure 63:
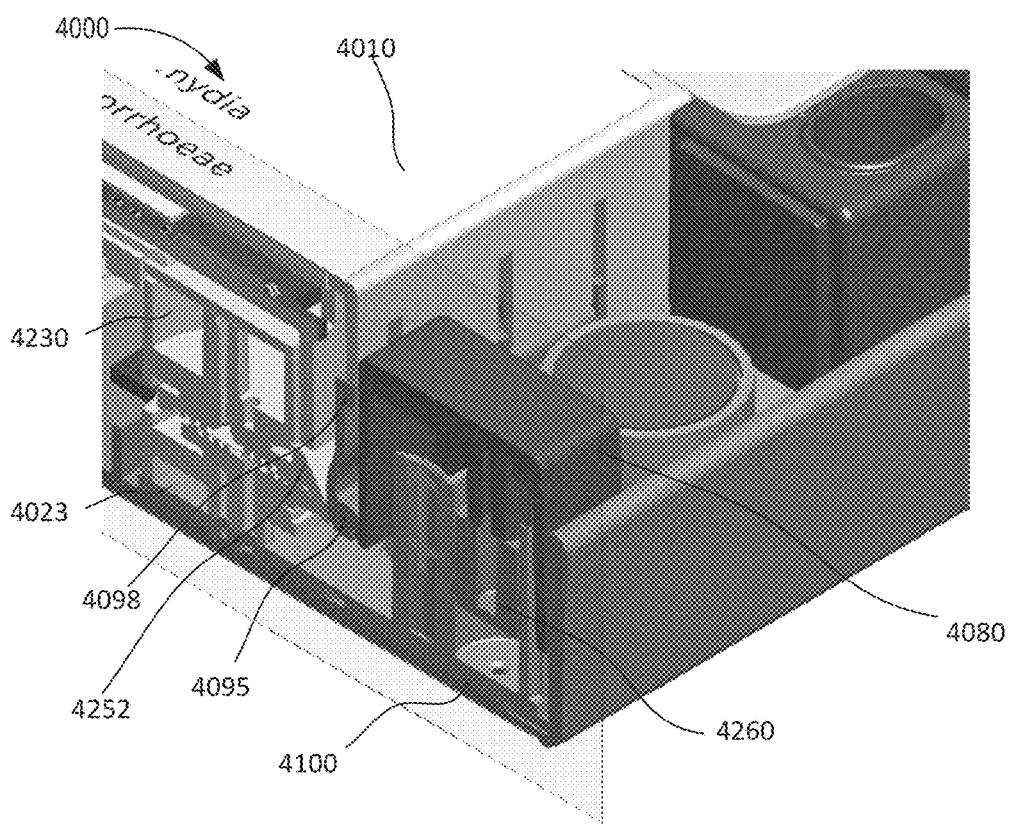

After the wash operation, the filter assembly is moved from its first configuration to its second configuration (FIG. 46). Specifically, the second plate 4252 is moved relative to the first plate 4251, as shown by the arrow KK in FIG. 46. The second plate 4252 includes a tapered actuation surface that is moved when the third actuator 4080 is moved from its first position to its second position. As shown in FIG. 63, the back surface 4082 and/or the spring clips 4095 of the third actuator 4080 contact the tapered surface and move the second plate 4252 to transition the filter assembly 4230 to its second configuration. When the filter assembly 4230 is in its second configuration (i.e., the "elution flow" configuration, see FIG. 46), the flow port 4256 of the second plate 4252 is in fluid communication with the elution inlet port 4248. Thus, when the filter assembly 4230 is in its second configuration, the elution buffer can flow from the elution module 4260 (described below) and through the filter membrane 4254, as indicated by the arrow LL in FIG. 46. The elution buffer and the captured particles flow out of the filter assembly 4230 and toward the lysing module 4300 via sample outlet port 4238.

The filter membrane 4254 captures the target organism/entity while allowing the bulk of the liquid within the sample and the wash composition to flow through into the waste reservoir 4205. The filter membrane 4254 (and any of the filter membranes described herein) can be any suitable membrane and or combination of membranes. For example, in some embodiments, the filter membrane 4254 is a woven nylon filter membrane with a pore size of about 1 μm (e.g., 0.8 μm, 1.0 μm, 1.2 μm) enclosed between the first plate 4251 and the second plate 4252 such that there is minimal dead volume. In such embodiments, the particle capture can be achieved primarily through a binding event. Such pore sizes and filter construction can lead to reduced fluid pressure during the sample delivery, wash and the elution operations. Such designs, however, may also allow target organisms to flow through the filter membrane 4254, potentially resulting in lower efficiency of capture. Furthermore, the target organism may be harder to remove on the elution step (e.g., the backwash) due to the nature of the binding. However, the resulting eluent solution is "cleaner" as more of the unwanted material gets washed away through the filter membrane 4254. Thus, the filter member 4254 and size thereof can be selected to be complimentary to and/or consistent with the target organism. For example, the filter membrane 4254 can be constructed and/or formulated to capture target specimens through either size exclusion (where anything smaller than the target organism is allowed to flow through the membrane), or via binding the target to the filter membrane through a chemical interaction (and later removing the target from the membrane with the elution solution).

For example, in some embodiments, the filter membrane 4254 can be a cellulose acetate filters with a pore size of approximately 0.35 μm, and can be constructed to achieve particle capture by size exclusion. Such filter construction, however, can tend to clog more easily, thus generating higher pressures during sample delivery, wash and the elution operations. In some embodiments, the internal pressures can be reduced by altering the diameter of the filter membrane 4254 and/or reducing the total volume of sample to be conveyed through the filter assembly 4230. In some embodiments, the filter membrane 4254 is a woven nylon filter membrane with a pore size of about 4 μm (e.g., 0.8 μm, 4.0 μm, 4.2 μm) enclosed between various plates of the filter assembly 4230 such that there is minimal dead volume.

The elution module (or assembly) 4260 of the sample preparation module 4200 is contained within the housing, and defines an elution volume within which an elution composition is stored. The elution composition can be any of the elution compositions described herein. In some embodiments, the elution composition can include proteinase K, which allows for the release of any bound cells and/or nucleic acid molecules (e.g., DNA) from the filter membrane. The output from the elution module 4260 can be selectively placed in fluid communication with the filter assembly 4230, when the filter assembly is toggled into its second (or backflow) configuration, as described above. Thus, the elution module 4260 can include any suitable flow control devices, such as check valves, duck-bill valves, or the like to prevent flow back towards and/or into the elution volume.

Importantly, as described herein, the elution module 4260 is configured such that it cannot be actuated out of the desired sequence of operations. Specifically, the elution module 4260 is configured to be locked until after the biological sample has been conveyed to the sample preparation module 4200 and the wash operation (described above) has occurred. The elution module 4260 includes the elution portion 4104 of the sample transfer manifold 4100, the reagent (or third) actuator 4080, and an elution plunger 4270. Referring to FIGS. 21-25, and 28, the elution portion 4104 of the sample transfer manifold 4100 includes a cylindrical housing 4262 that defines an elution volume 4263 within which the elution buffer (or composition) is contained.

Figure 28:
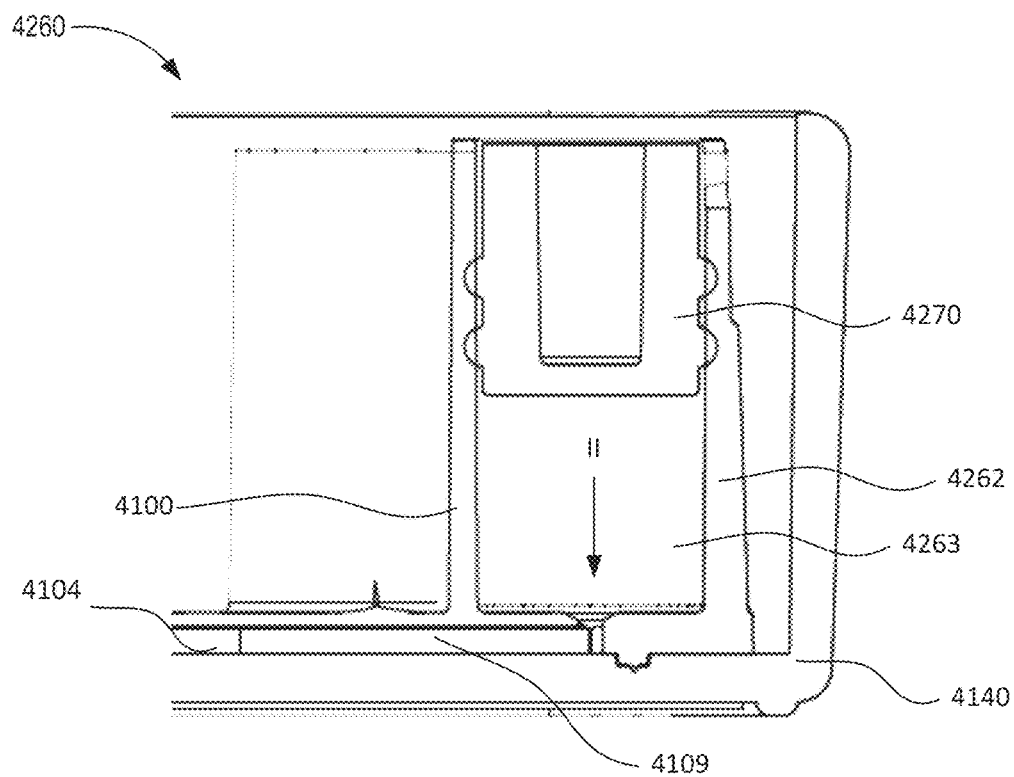
Figure 29:
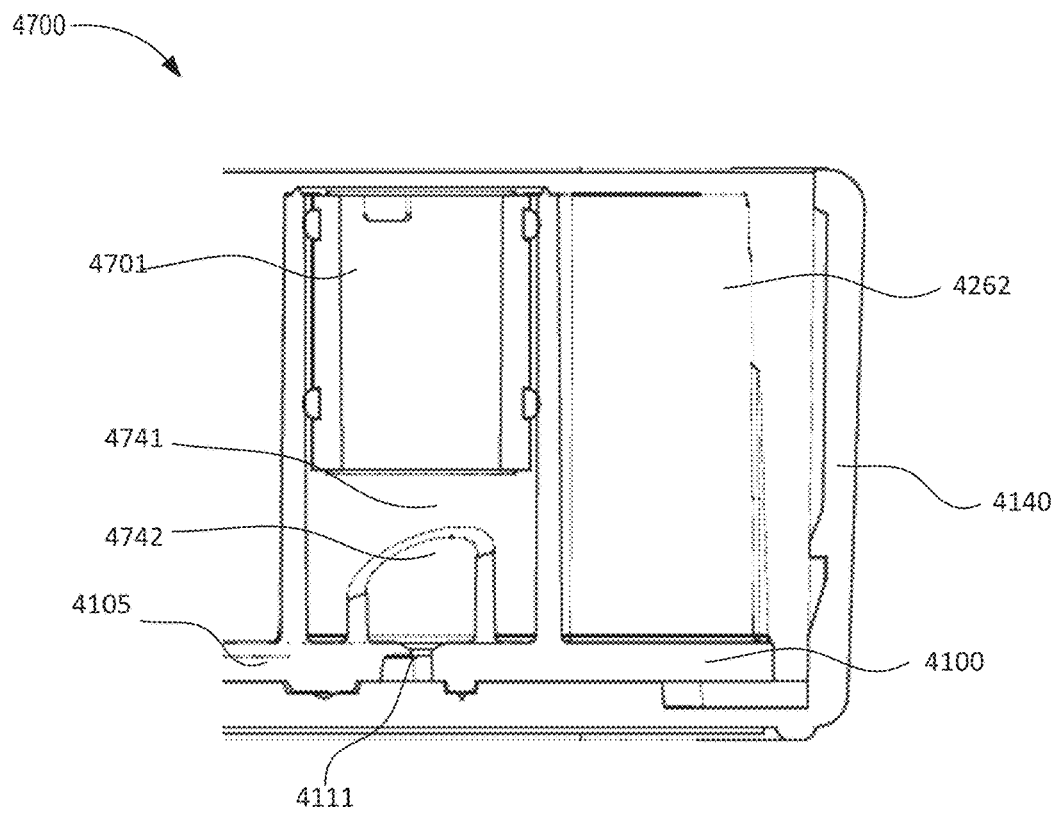

As shown in FIG. 28, the elution plunger 4270 is sealingly engaged with in inner side wall of the cylindrical housing 4262. The elution plunger 4270 can include any number of seals (e.g., O-rings, gaskets, elastomeric portions, or the like) to fluidically isolate the volume 4263 from the external volume of the device 4000. In some embodiments, the elution plunger can include a vent opening to allow controlled fluid communication of the volume 4263 with an external volume. The elution composition within the volume 4263 can be any suitable solution of the types described herein.

The lower portion of the cylindrical housing 4262 defines an opening into the elution input passage 4109. In use, when the elution plunger 4270 is moved downward (in the direction shown by the arrow II), the elution composition is moved from within the volume 4263 to the elution input passage 4109. The elution input passage 4109 extends to the filter assembly 4230, and is communication with the elution input port 4248 described above. In this manner, after the biological sample and the wash solution are conveyed from the sample input volume 4068 to the filter assembly 4230, an elution composition can be backflushed through the filter assembly 4230, as described above.

Figure 38:
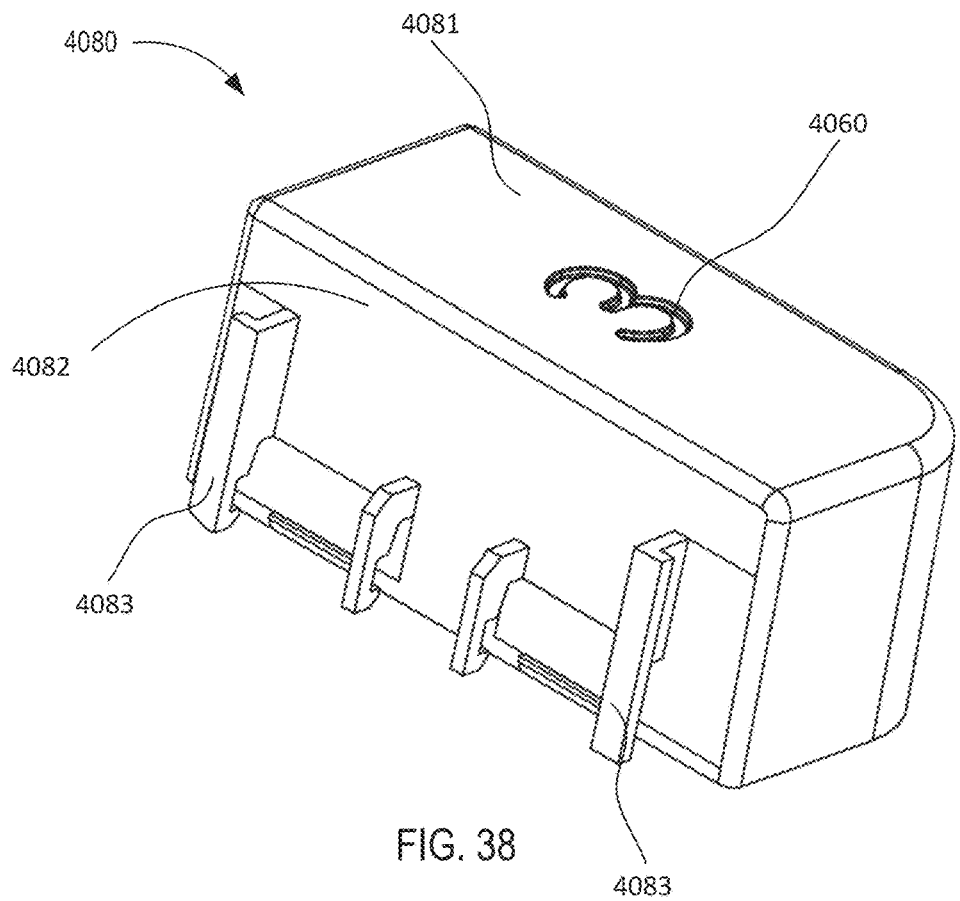
FIGS. 38 and 39 are a rear perspective view and a bottom perspective view, respectively, of a second reagent actuator of the molecular diagnostic test device shown in FIGS. 10 and 11.
Figure 39:
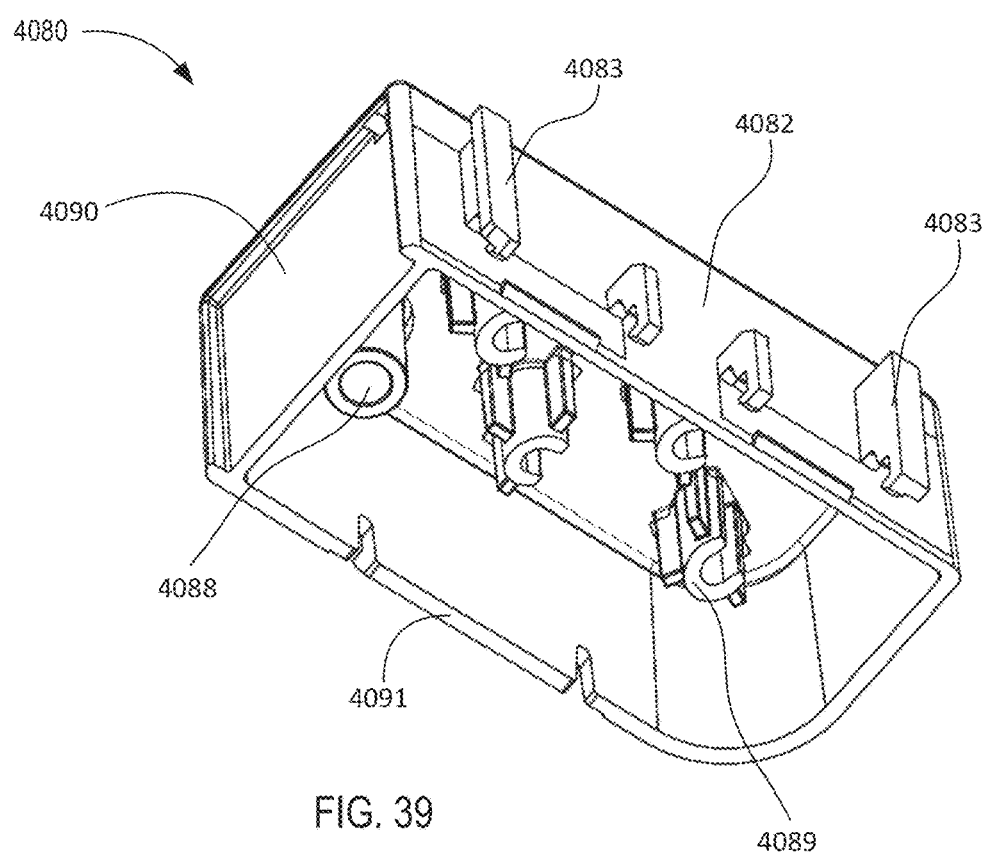
Figure 41:
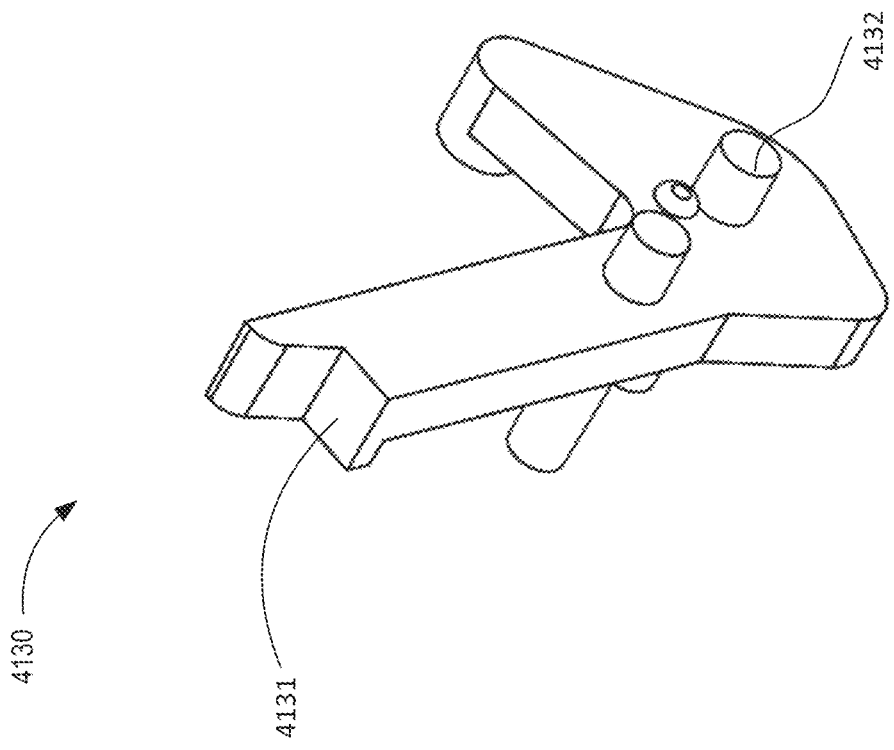
FIGS. 41 and 42 are a front perspective view and a rear perspective view, respectively, of a lock lever coupled to the sample transfer manifold shown in FIG. 23.

The elution module 4260 is actuated by the reagent (or third) actuator 4080. Referring to FIGS. 38-39, the reagent (or third) actuator 4080 includes a top surface 4081, a front surface 4091, a side surface 4090, a back surface 4082, and an inner surface. The top surface 4081 includes an indicator 4060 (i.e., "3") to guide a user in the correct sequence of steps for use of the apparatus 4000. The side surface 4090 includes a recessed area that matingly engages with the side surface 4078 of the second actuator 4050. In this manner, when the third actuator 4080 is moved to its second position, the side surface 4078 of the second actuator 4070 guides the movement of the third actuator 4080. The front surface 4091 includes a protrusion that engages the side wall of the lower housing 4040 to lock and/or retain the third actuator 4080 in its second position. The inner surface includes a protrusion 4088 that engages the elution plunger 4270 and moves the elution plunger 4270, as described herein. The inner surface includes four reagent protrusions 4089 that each engage a reagent canister within the reagent module 4700 to puncture the reagent canisters when the third actuator 4080 is moved.

The back surface 4082 includes a pair of mounting protrusions 4083. The mounting protrusions 4083 are received within the actuator guide slots 4031. Additionally, the mounting protrusions 4083 each include a connection portion that is connected to the base 4096 of the spring clips 4095 (see FIG. 40) coupled to the third actuator 4080. In particular, two spring clips 4095 are coupled to the mounting protrusions 4083 such that when the third actuator 4080 is in its first position, the lock protrusion 4032 of the housing (i.e., between the two actuator guide slots 4031) is between the spring clips 4095 and the back surface 4082 (similar to the arrangement shown in FIG. 58). The resilient portion 4097 of each spring clip 4095 biases the lock portion 4098 of each spring clip 4095 against the lock protrusion 4032. Similar to the arrangement shown in FIG. 59, when the third actuator 4080 is moved to its second (or actuated) position, the lock portions 4098 becomes disengaged with the lock protrusion 4032 of the housing, and contact the back surface 4082 of the third actuator 4080. In this manner, the lock portions 4098 will engage the shoulder of the lock protrusion 4032 if the third actuator 4080 is moved back towards its first position. In this manner, the third actuator 4080 is retained in its second position.

As described above, the back surface 4083 also functions to actuate the filter assembly 4230 when the third actuator 4080 is moved to its second position. In some embodiments, the back surface 4083 can include specific protrusions and/or surfaces to ensure that the filter assembly 4230 is actuated at the proper time relative to the movement of the elution plunger 4270.

FIGS. 47-52 show various views of the lysing module 4300 (also referred to as an inactivation module). The lysing module 4300 includes a chamber body 4310, a bottom lid 4318, a heater 4330, and an electrode assembly. The chamber body 4310 and the bottom lid 4318 can be referred to as a flow member. Although the flow member is shown as being constructed from two pieces (the body 4310 and the bottom lid 4318) that are coupled together, in other embodiments, the flow member can be monolithically constructed. The chamber body 4310 and the bottom lid 4318 define an input port 4312, a first (or holding) volume 4311, a vent 4314, a second (or inactivation) volume 4321, and an output port 4313. The input port 4312 can receive the eluent from the elution chamber and/or directly from the filter assembly 4230. In other embodiments, however, the input port 4312 can be fluidically coupled to a sample input module without the biological input being conveyed through a filter. In use, the eluent can flow into the lysing module 4300 and be collected in the holding volume 4311. The sample can be lysed within the holding volume 4311. For example, in some embodiments, the eluent containing the target organisms can be heated by the heater 4330 to maintain the eluent at or above a target lysing temperature. Similarly stated, in some embodiments, the heater 4330 can be coupled to the chamber body 4310 and/or the bottom lid 4318 such that the heater 4330 can convey thermal energy into the lysing module 4300 to produce a lysing temperature zone within the holding volume 4311. The lysing temperature zone can maintain the eluent at any of the temperatures and for any of the time periods described herein.

The vent opening 4314 is in fluid communication with the first volume 4311, and thus allows air to flow into or out of the lysing module 4300 (including the first volume 4311 and the second volume 4321) as sample is conveyed into and/or out of the lysing module 4300. The vent 4314 can also relieve pressure within either of the first volume 4311 or the second volume 4321 when the eluent is heated. Although shown as being a permanent vent (i.e., a vent having a fixed opening), in some embodiments, the lysing module 4300 (or any of the lysing modules described herein) can have an active vent. For example, in some embodiments, the lysing module 4300 (or any of the lysing modules described herein) can include a valve that controls the venting of pressure and/or air from within the lysing module 4300.

The first volume 4311 is in fluid communication with the second volume 4322. In this manner, the eluent can flow from the first (or holding) volume 4311 through the second (or inactivation) volume 4321 of the lysing module 4300. More specifically, when a pressure gradient is applied across the input port 4312 and the output port 4313, the eluent can flow from the holding volume 4311 (first volume) through the second volume 4322. The pressure gradient can be applied by any suitable mechanism, such as for example, a pump (e.g., the fluidic drive module 1400). As shown, the second volume 4321 is a serpentine channel that provides a high surface area to volume ratio. This arrangement allows for rapid inactivation of the lysis enzymes in the eluent. The eluent, after being flowed through the inactivation segment, may be flowed into the output port 4313 to be collected and/or conveyed to an amplification module (not shown).

As described above, the flow member is in contact with a heating element 4330, which can be, for example, a printed circuit board (PCB) heater. The heating element 4330 may function to heat the eluent as it flows through the second volume 4311 at a high temperature sufficient to inactivate the one or more lysis enzymes contained within the eluent. For example, the heating element may heat the eluent to about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C. or greater than 100° C. By heating the liquid eluent to a high temperature, the lysis enzymes as well as any other enzymes present can be deactivated. In some embodiments, the sample can be heated to about 95 C for about 4 minutes.

In some embodiments, the heater on the PCB 4330 is specifically designed to heat the serpentine portion of the lysing module 4300 (i.e., the second volume 4321) while not heating the holding volume 4311. Because the lid 4318 of the lysing module 4300 is thick, the heater surface may be heated well above the desired temperature of the fluid. Since the electrodes 4971, 4972 (described in more detail below) are thermally conductive and come into direct contact with the fluid, the fluid surrounding the electrodes 4971, 4972 will experience the same temperature as the heater surface, which may cause evaporation. To minimize the heating of the holding volume 4311, a slot (not shown) may be cut in the PCB 4330 to isolate the heater from the portion of the PCB adjacent and/or in contact with the holding volume 4311. For example, in some embodiments, the heater 4330 can include a series of slots and/or openings as described in U.S. patent application Ser. No. 15/494,145, entitled "Printed Circuit Board Heater for an Amplification Module," which is incorporated herein by reference in its entirety. Moreover, in some embodiments, the heating element of the heater 4330 is located on an internal layer so the top copper pour (not shown) can be used as a heat spreader to minimize temperature variation along the serpentine path. The six wires soldered to the PCB 4330 may remove heat from the surrounding area, creating temperature gradients across the heater surface. To minimize this effect, wires may be soldered on both sides of the heater surface so the temperature roll off is symmetrical.

In some embodiments, the lysing module 4300 can determine whether there is liquid in the first volume 4311 and/or the second volume 4321. Specifically, the lysing module 4300 includes electrical probes to determine electrical resistance of the fluid within the first volume. In some embodiments, the molecular diagnostic device (e.g., the device 1000) can include an electronic controller configured to determine when the user has actuated the elution module (e.g., by pressing the reagent actuator 4080 described above) by detecting the presence of liquid in the first volume 4311. In this manner, the introduction of liquid into the first volume 4311 can trigger the start of the device.

Specifically, the control system and/or the lysing module 4300 includes two electrodes 4971, 4972 inside the first volume 4311. The electrodes 4971, 4972 are connected to circuitry (e.g., a controller, not shown) that detects a resistance change between the two electrodes 4971, 4972. Fluid may be reliably detected between the electrodes 4971, 4972 due to the high gain of the circuit, which may easily differentiate between an open circuit condition (no fluid) and a non-negligible resistance across the electrodes 4971, 4972 (fluid detected). Use of a sample matrix with high salt concentration increases the conductivity of the fluid, which may make the fluid easily detectable even with variation across samples.

The electrodes 4971, 4972 and the circuitry (not shown) are designed to detect fluid without impacting the biological processes that take place in the device. For example, the electrodes 4971, 4972 are specifically chosen so as not inhibit PCR reactions. In some embodiments, the electrodes 4971, 4972 are gold plated.

Both DNA and cells have a net charge so they may migrate in the presence of an electric field. Because the resistance change between the electrodes 4971, 4972 is determined by measuring a change in electric potential, precautions may be taken to minimize the impact of this electromotive force. For example, once fluid is detected voltage may be removed from the electrodes 4971, 4972 and they may be electrically shorted together. This ensures there is no potential difference between the electrodes 4971, 4972 and the charged particles (DNA, cells, salts, etc.) will not bind to the electrodes, which would prevent them from entering the amplification module (not shown).

As described, the solution within the second volume 4321 is rapidly heated to temperatures of up to about 100 degrees Celsius. The lysing module 4300 and/or the formulation of the input solution (e.g., the eluent), however, can collectively reduce the likelihood that the liquid portion of the input solution will boil during the lysing/inactivation operations. Such boiling can produce undesirable bubbles and/or air pockets and can reduce the repeatability of the lysing and/or inactivation operations. Moreover, to facilitate use of the device at a variety of different altitudes, the lysing module 4300 and/or the formulation of the input solution can collectively reduce the likelihood that the liquid portion of the input solution will boil at a temperature of 99 degrees Celsius or higher, 98 degrees Celsius or higher, 96 degrees Celsius or higher, 94 degrees Celsius or higher, 92 degrees Celsius or higher, 90 degrees Celsius or higher, or 88 degrees Celsius or higher. For example, in some embodiments, the input solution can include salts and/or sugars to raise the boiling temperature of the input solution. In other embodiments, the lysing module 4300 can include one or more vent openings into either the first volume 4311 or the second volume 4321 or both (to limit pressure build-up during heating).

After the lysing and inactivation operations, the output from the lysing module 4300 can be conveyed into the mixing module (also referred to as simply the mixing chamber) 4500, which mixes the output of inactivation module 4300 with the reagents to conduct a successful amplification reaction. Similarly stated, the mixing module 4500 is configured to reconstitute the reagent in a predetermined input volume, while ensuring even local concentrations of reagents in the entirety of the volume. In some embodiments, the mixing chamber module 4500 is configured to produce and/or convey a sufficient volume of liquid for the amplification module 4600 to provide sufficient volume output to the detection module 4800. The mixing module 4500 can be any suitable mixing module, such as those shown and described in International Patent Publication No. WO2016/109691, entitled "Devices and Methods for Molecular Diagnostic Testing," which is incorporated herein by reference in its entirety The fluidic drive (or transfer) module 4400 can be a pump or series of pumps configured to produce a pressure differential and/or flow of the solutions within the diagnostic test device 4000. Similarly stated, the fluid transfer module 4400 is configured to generate fluid pressure, fluid flow and/or otherwise convey the biological sample and the reagents through the various modules of the device 4000. The fluid transfer module 4400 is configured to contact and/or receive the sample flow therein. Thus, in some embodiments, the device 4000 is specifically configured for a single-use to eliminate the likelihood that contamination of the fluid transfer module 4400 and/or the sample preparation module 4200 will become contaminated from previous runs, thereby negatively impacting the accuracy of the results. The fluid transfer module 4500 can be any suitable fluid transfer module, such as those shown and described in International Patent Publication No. WO2016/109691, entitled "Devices and Methods for Molecular Diagnostic Testing," which is incorporated herein by reference in its entirety.

After being mixed within the mixing module 4500, the prepared sample is then conveyed to the amplification module 4600 (as shown by the arrow EE in FIG. 9). The amplification module 4600 includes a flow member 4610 and a heater 4630. The flow member 4610 can be any suitable flow member that defines a volume or a series of volumes within which the that prepared solution S3 can flow and/or be maintained to amplify the target nucleic acid molecules within the solution S3. The heater 4630 can be any suitable heater or group of heaters coupled to the flow member 4610 that can heat the prepared solution within the flow member 4610 to perform any of the amplification operations as described herein. For example, in some embodiments, the amplification module 4600 (or any of the amplification modules described herein) can be similar to the amplification modules shown and described in U.S. patent application Ser. No. 15/494,145, entitled "Printed Circuit Board Heater for an Amplification Module," which is incorporated herein by reference in its entirety. In other embodiments, the amplification module 4600 (or any of the amplification modules described herein) can be similar to the amplification modules shown and described in International Patent Publication No. WO2016/109691, entitled "Devices and Methods for Molecular Diagnostic Testing," which is incorporated herein by reference in its entirety.

In some embodiments, the flow member 4610 defines a single volume within which the prepared solution is maintained and heated to amplify the nucleic acid molecules within the prepared solution. In other embodiments, the flow member 4610 can define a "switchback" or serpentine flow path through which the prepared solution flows. Similarly stated, the flow member 4610 defines a flow path that is curved such that the flow path intersects the heater 4630 at multiple locations. In this manner, the amplification module 4600 can perform a "flow through" amplification reaction where the prepared solution flows through multiple different temperature regions.

The flow member 4610 (and any of the flow members described herein) can be constructed from any suitable material and can have any suitable dimensions to facilitate the desired amplification performance for the desired volume of sample. For example, in some embodiments, the amplification module 4600 (and any of the amplification modules described herein) can perform 4000× or greater amplification in a time of less than 45 minutes. For example, in some embodiments, the flow member 4610 (and any of the flow members described herein) is constructed from at least one of a cyclic olefin copolymer or a graphite-based material. Such materials facilitate the desired heat transfer properties into the flow path. Moreover, in some embodiments, the flow member 4610 (and any of the flow members described herein) can have a thickness of less than about 0.5 mm. In some embodiments, the flow member 4610 (and any of the flow members described herein) can have a volume about 450 microliters or greater, and the flow can be such that at least 40 microliters of sample is amplified. In other embodiments, at least 20 microliters of sample are amplified by the methods and devices described herein. In other embodiments, at least 30 microliters of sample are amplified by the methods and devices described herein. In yet other embodiments, at least 50 microliters of sample are amplified by the methods and devices described herein.

The heater 4630 can be any suitable heater or collection of heaters that can perform the functions described herein to amplify the prepared solution. In some embodiments, the heater 4630 can establish multiple temperature zones through which the prepared solution flows and/or can define a desired number of amplification cycles to ensure the desired test sensitivity (e.g., at least 30 cycles, at least 34 cycles, at least 36 cycles, at least 38 cycles, or at least 40 cycles). The heater 4630 (and any of the heaters described herein) can be of any suitable design. For example, in some embodiments, the heater 4630 can be a resistance heater, a thermoelectric device (e.g. a Peltier device), or the like. In some embodiments, the heater 4630 can be one or more linear "strip heaters" arranged such that the flow path crosses the heaters at multiple different points. In other embodiments, the heater 4630 can be one or more curved heaters having a geometry that corresponds to that of the flow member 4610 to produce multiple different temperature zones in the flow path.

Although the amplification module 4600 is generally described as performing a thermal cycling operation on the prepared solution, in other embodiment, the amplification module 4600 can perform any suitable thermal reaction to amplify nucleic acids within the solution. In some embodiments, the amplification module 4600 (and any of the amplification modules described herein) can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process The detection methods enabled by the device 4000 include sequential delivery of the detection reagents and other substances within the device 4000. Further, the device 4000 is configured to be an "off-the-shelf" product for use in a point-of-care location (or other decentralized location), and is thus configured for long-term storage. Accordingly, the reagent storage module 4700 is configured for simple, non-empirical steps for the user to remove the reagents from their long-term storage containers, and for removing all the reagents from their storage containers using a single user action. In some embodiments, the reagent storage module 4700 and the rotary selection valve 4340 are configured for allowing the reagents to be used in the detection module 4800, one at a time, without user intervention.

Specifically, the device 4000 is configured such that the last step of the initial user operation (i.e., the depressing of the reagent actuator 4080) results in dispensing the stored reagents. This action crushes and/or opens the sealed reagent containers present in the assembly and relocates the liquid for delivery. The rotary venting selector valve 4340 allows the reagent module 4700 to be vented for this step, and thus allows for opening of the reagent containers, but closes the vents to the tanks once this process is concluded. Thus, the reagents remain in the reagent module 4700 until needed in the detection module 4800. When a desired reagent is needed, the rotary valve 4340 opens the appropriate vent path to the reagent module 4700, and the fluidic drive module 4400 applies vacuum to the output port of the reagent module 4700 (via the detection module 4800), thus conveying the reagents from the reagent module 4700. The reagent module 4700 and the valve 4340 can be similar to the reagent modules and valves shown and described in International Patent Publication No. WO2016/109691, entitled "Devices and Methods for Molecular Diagnostic Testing," which is incorporated herein by reference in its entirety.

The detection module 4800 is configured to receive output from the amplification module 4600 and reagents from the reagent module 4700 to produce a colorimetric change to indicate presence or absence of target organism in the initial input sample. The detection module 4800 also produces a colorimetric signal to indicate the general correct operation of the test (positive control and negative control). In some embodiments, color change induced by the reaction is easy to read and binary, with no requirement to interpret shade or hue. The detection module 4800 can be similar to the detection modules shown and described in International Patent Publication No. WO2016/109691, entitled "Devices and Methods for Molecular Diagnostic Testing," which is incorporated herein by reference in its entirety.

Figure 64:
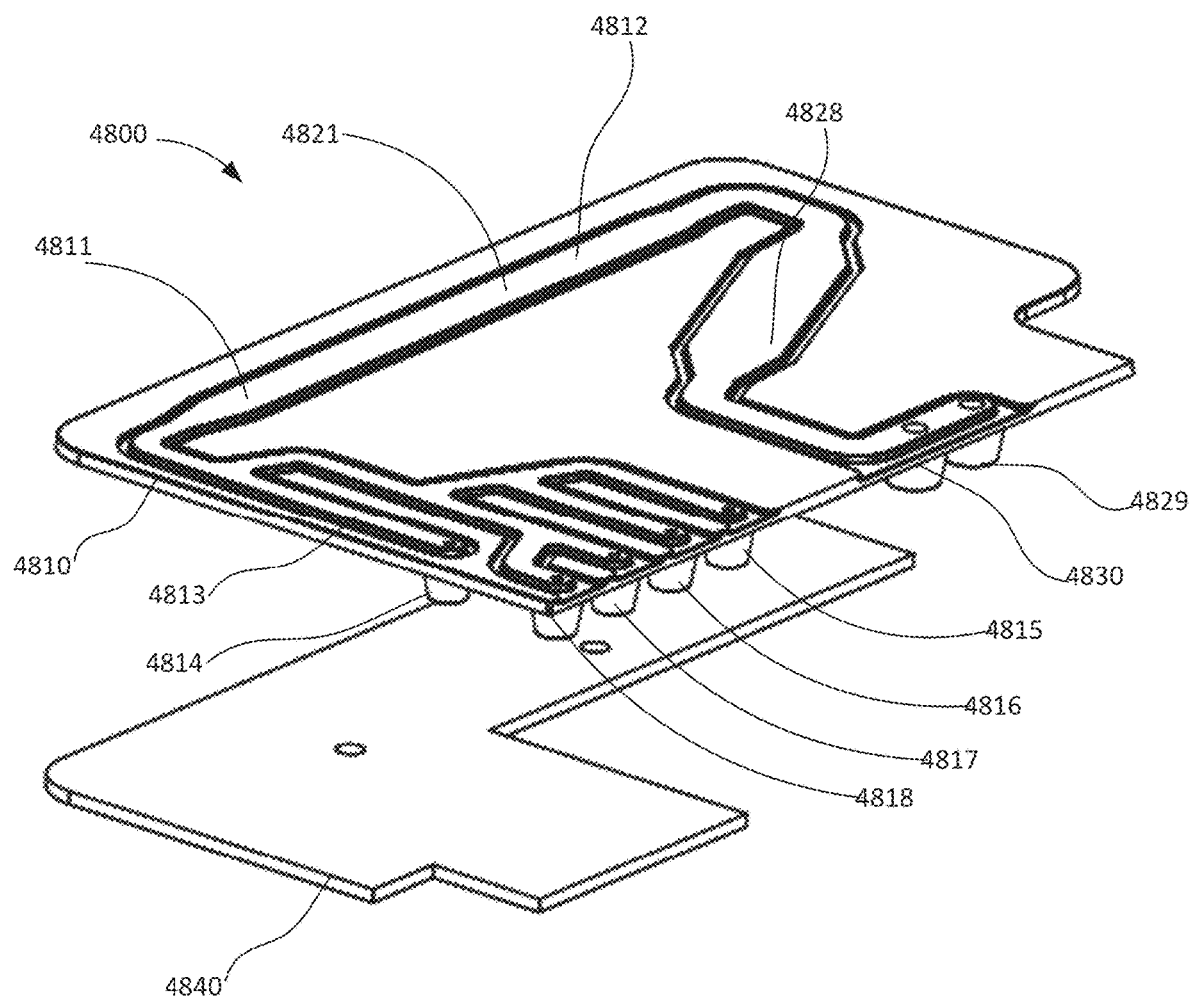
FIGS. 64 and 65 are a perspective exploded view and a front view, respectively, of a detection module of the molecular diagnostic test device shown in FIGS. 10 and 11.

Referring to FIGS. 64 and 65, the detection module includes a lid (not shown, but similar to the lid 2802 shown and described above), a detection housing 4810 and a heater 4840. The heater 4840 can be similar to any of the circuit board heaters described herein and also shown and described in International Patent Publication No. WO2016/109691, entitled "Devices and Methods for Molecular Diagnostic Testing," which is incorporated herein by reference in its entirety.

The lid and the detection housing 4810 form a flow cell for detection. The housing 4810 defines a detection chamber/channel 4812 having a sample inlet portion 4813, a reagent inlet portion, a detection portion 4821, and an outlet portion 4828. The sample inlet portion 4813 includes the sample inlet port 4814, which is fluidically coupled to the outlet of the amplification module 4600 and receives the amplified sample. The reagent inlet portion includes a first reagent inlet port 4815, a second reagent inlet port 4816, a third reagent inlet port 4817, and a fourth reagent inlet port 4818. The first reagent inlet port 4815 is coupled to the reagent module 4700 via the fluid passage 4043 of the vertical manifold 4035. Thus, in use a first reagent (e.g., a detection reagent, such as the first reagent R1 described above with reference to the reagent module 2700) can be conveyed into the detection channel 4812 via the first reagent inlet port 4815. The second reagent inlet port 4816 is coupled to the reagent module 4700 via the fluid passage 4044 of the vertical manifold 4035. Thus, in use a second reagent (e.g., a wash solution) can be conveyed into the detection channel 4812 via the second reagent inlet port 4816. The third reagent inlet port 4817 is coupled to the reagent module 4700 via the fluid passage 4045 of the vertical manifold 4035. Thus, in use a third reagent (e.g., a detection reagent, such as the second reagent R2 described above with reference to the reagent module 2700) can be conveyed into the detection channel 4812 via the third reagent inlet port 4817. The fourth reagent inlet port 4818 is coupled to the reagent module 4700 via the fluid passage 4046 of the vertical manifold 4035. Thus, in use a fourth reagent (e.g., a second flow of a detection reagent, such as the second reagent R2 described above with reference to the reagent module 2700) can be conveyed into the detection channel 4812 via the first reagent inlet port 4818.

The detection channel 4812 includes an entrance portion 4811, a detection portion 4821, and outlet portion 4828. The detection portion (or "read lane") 4821 is defined, at least in part by, and/or includes a series of detection surfaces. The detection surfaces 4821 include a series of capture probes to which the target amplicon can be bound when the detection solution flows across the detection surface 4821. The capture probes can be any suitable probes formulated to capture or bind to the target amplicon, such as those described above with respect to the detection module 2800. Specifically, the detection portion 4821 includes five detection surfaces. Each of the detection surfaces are chemically modified to contain a desired capture probe configuration. Specifically, a first detection surface can include a hybridization probe specific to *Neisseria gonorrhea* (NG). A second detection surface can include a hybridization probe specific to *Chlamydia trachomatis* (CT). A third detection surface can include a hybridization probe specific to *Trichomonas vaginalis* (TV). A fourth detection surface can include non-target probe for a negative control. A fifth detection surface can include a hybridization probe for a positive control (*A. fischeri, N. subflava,* or the like).

The negative control surface 4825 includes a non-target probe and should always appear white (no color). In some embodiments, the negative control surface can be placed as the last spot (i.e., in the direction of flow as indicated by the arrow SS) because this arrangement shows whether the reagent volumes, fluidic movement, and wash steps were working properly.

The size and shape of the detection surfaces can be similar that described above with reference to the detection module 2800. Similarly, the size (width, depth and/or length) of the detection portion 4821 of the channel 4812 can be similar that described above with reference to the detection module 2800. Moreover, in some embodiments, the detection channel 4812 (and any of the detection channels described herein) can be free from a porous material. Said another way, in some embodiments, the detection channel 4812 (and any of the detection channels described herein) can a flow through device that does not include a detection strip (i.e., a porous or membrane-like material, such as cellulose, that wicks or otherwise absorbs the solutions flowed therethrough).

Figure 62:
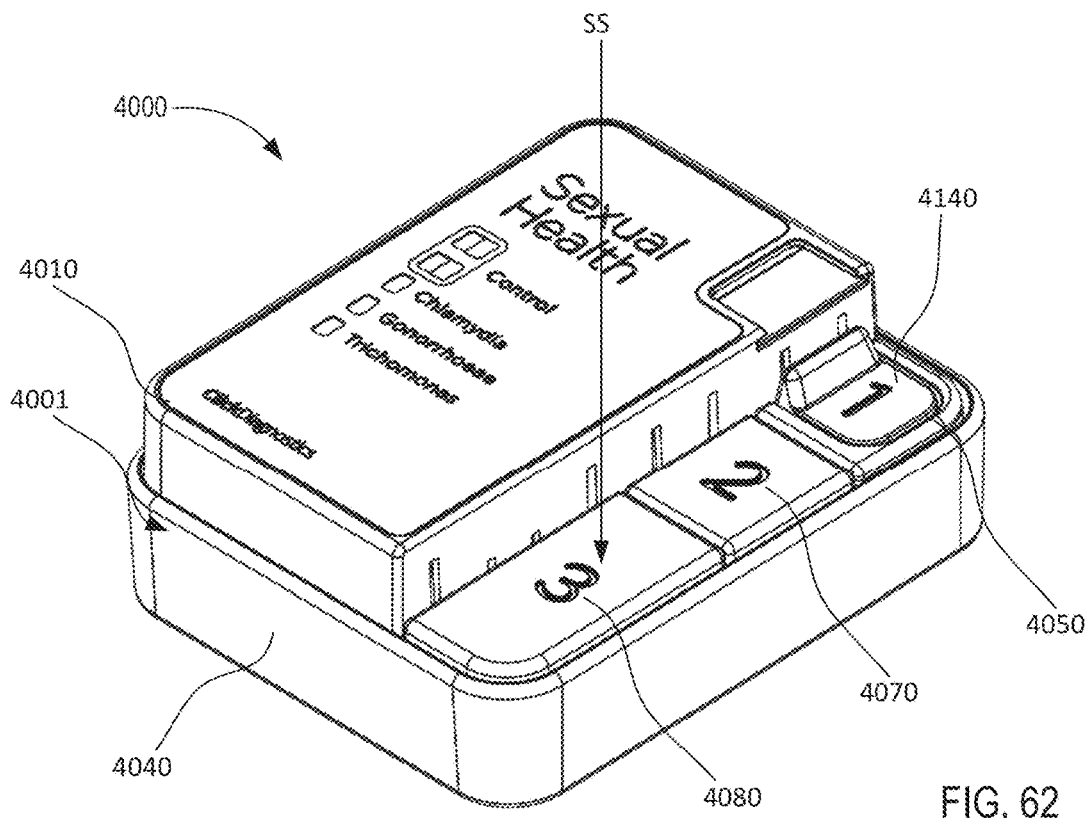
FIGS. 62 and 63 are a perspective view and a side cross-sectional view, respectively, of the molecular diagnostic test device shown in FIGS. 10 and 11, showing the sample input actuator in its second position, the first reagent actuator in its second position, and the second reagent actuator in its second position.

The device 4000 can be used to perform any of the methods described herein. To use the device, a biological sample is first placed into the sample input volume 4068, as described above. The lid 4140 is then moved to it closed position, thereby sealing the sample input volume 4068. After the lid 4140 is closed, the first actuator 4050 can be manipulated to actuate the sample input module 4170, as shown by the arrow OO in FIG. 56. As shown in FIGS. 58 and 59, movement of the first actuator 4050 compresses the sample input volume 4068 and pushes the sample to the filter assembly 4230. The movement of the first actuator 4050 unlocks the second actuator 4070 (by moving the lock 4130, as described above). The second actuator 4070 can then be depressed, as shown by the arrow QQ in FIG. 60. This causes the wash solution to be conveyed into the filter assembly 4230, as described above. The movement of the second actuator 4070 unlocks the third actuator 4080 (by moving the lock 4130, as described above). The third actuator 4080 can then be depressed, as shown by the arrow SS in FIG. 62. This actuates the filter assembly 4230 (to move the second plate 4252, as described above) and also causes the elution solution to be conveyed into the filter assembly 4230, as described above. The movement of the third actuator 4080 also releases the reagents from the reagent canisters.

The eluted solution is flowed in a backflush operation through the filter assembly 4230 and towards the inactivation/lysing module 4300. As described above the lysing module 4300 includes a sensor that actuates the remaining portions of the device 4000, thereby causing the device 4000 to complete the detection operations as describe above.

In one aspect, a device is provided comprising: (a) an input port, configured to receive the biological sample comprising one or more biological cells or biological entities; (b) a filter assembly comprising a filter configured to capture the one or more biological cells or biological entities, wherein the input port is configured to relay the biological sample to the filter assembly; (c) one or more reservoirs comprising a wash solution, a lysis solution, or both, operably coupled to the filter assembly; (d) a waste chamber, operably coupled to the filter assembly and configured to receive waste from the filter assembly; and (e) an elution chamber, operably coupled to the filter assembly and configured to receive an eluent from the filter assembly.

Figure 66:
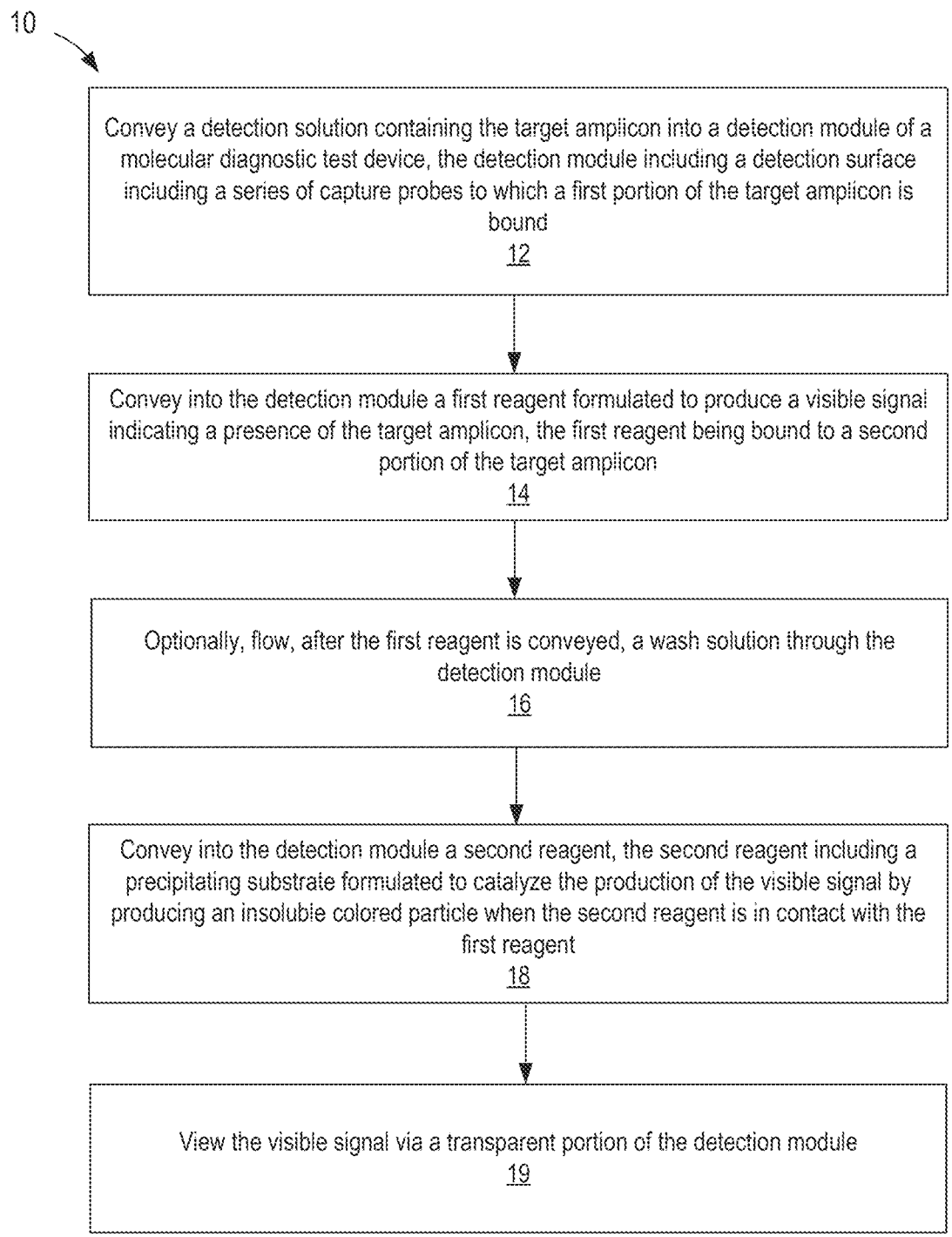
FIG. 66 shows a flow chart of a method of detecting a target organism, according to an embodiment.

FIG. 66 is a flow chart of a method 10 of detecting a target amplicon, according to an embodiment. The method 10 includes conveying a detection solution containing the target amplicon into a detection module of a molecular diagnostic test device, at 12. The detection module, which can be any of the detection modules described herein (e.g., the detection modules 2800, 3800 or 4800) includes a detection surface including a series of capture probes to which a first portion of the target amplicon is bound in response to the conveying.

A first reagent formulated to produce a visible signal indicating a presence of the target amplicon is then conveyed into the detection module, at 14. The first reagent is bound to a second portion of the target amplicon in response to being conveyed. The first reagent can be any of the reagents described herein, including the first reagent R1 described above in connection with the detection module 2800.

In some embodiments, the method optionally includes flowing, after the first reagent is conveyed, a wash solution through the detection module, at 16. The method further includes conveying into the detection module a second reagent, at 18. The second reagent includes a precipitating substrate formulated to catalyze the production of the visible signal by producing an insoluble colored product when the second reagent is in contact with the first reagent. The second reagent can be any of the reagents described herein, including the second reagent R2 described above in connection with the detection module 2800. In some embodiments, the method 10 can optionally include evacuating and/or washing the second reagent from the detection module (e.g., via wash or vacuum operation), thereby leaving the colored product present in the detection module. A visible signal is then viewed via a transparent portion of the detection module, at 19. In some embodiments, the visible signal can persist for viewing for up to one hour, two hours, twelve hours, twenty four hours, or forty eight hours.

Figure 67:
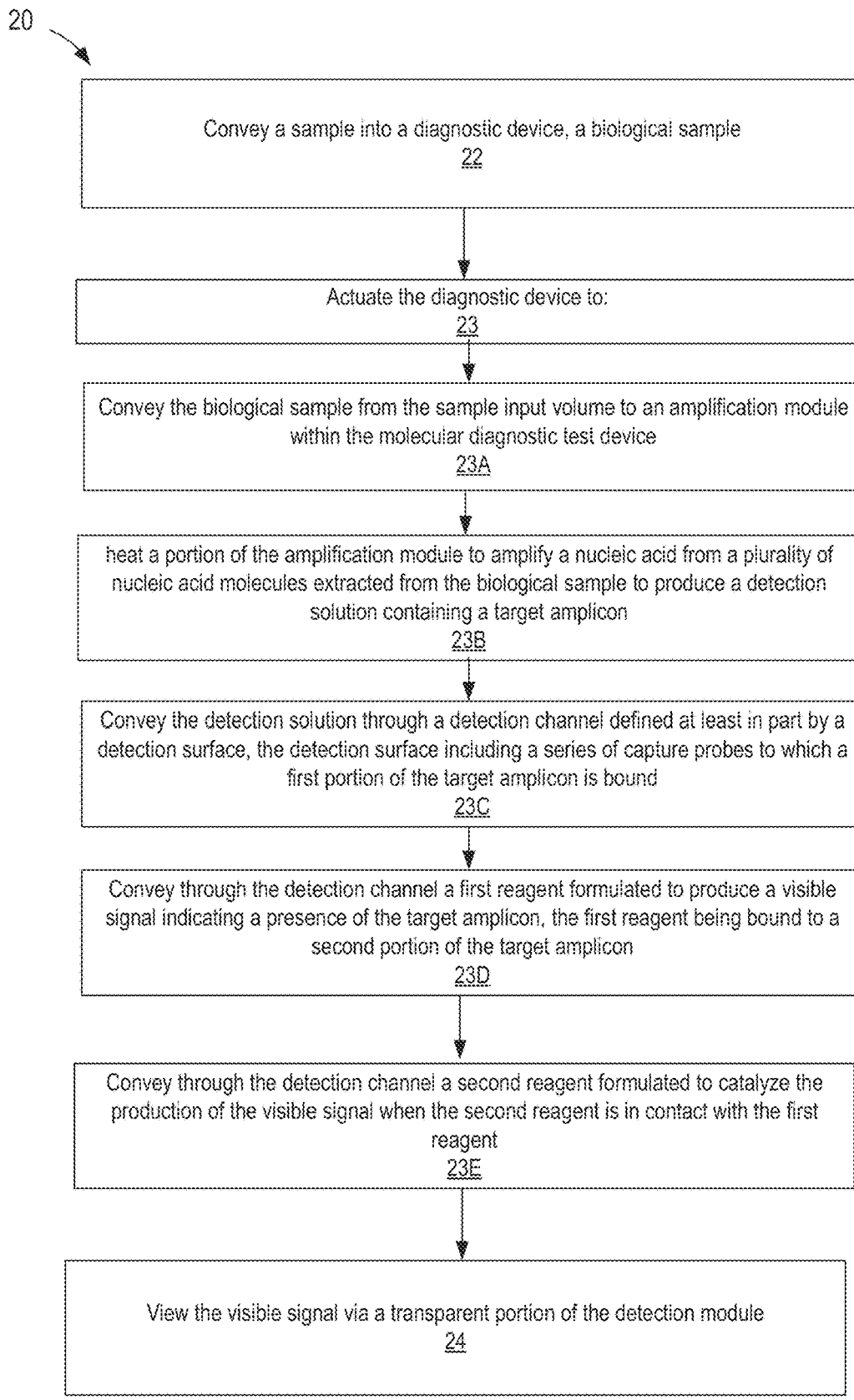
FIG. 67 shows a flow chart of a method of detecting a target organism, according to an embodiment.

FIG. 67 is a flow chart of a method 20 of detecting a target amplicon, according to an embodiment. The method 20 includes conveying a detection solution containing the target amplicon into a detection module of a molecular diagnostic test device, at 22. The detection module, which can be any of the detection modules described herein (e.g., the detection modules 2800, 3800 or 4800) includes a detection surface including a series of capture probes to which a first portion of the target amplicon is bound in response to the conveying. The device, which can be any of the device described herein is then actuated at 23 to cause the device to perform the following operations.

The biological sample is conveyed from the sample input volume to an amplification module within the molecular diagnostic test device, at 23A. A portion of the amplification module is then heated to amplify a nucleic acid from a plurality of nucleic acid molecules extracted from the biological sample to produce a detection solution containing a target amplicon, at 23B. The detection solution is then conveyed through a detection channel defined at least in part by a detection surface, the detection surface including a series of capture probes to which a first portion of the target amplicon is bound, at 23C. A first reagent formulated to produce a visible signal indicating a presence of the target amplicon is then conveyed through the detection channel, at 23D. The first reagent is bound to a second portion of the target amplicon when conveyed through the detection channel. A second reagent formulated to catalyze the production of the visible signal when the second reagent is in contact with the first reagent is then conveyed through the detection channel, at 23E.

A visible signal is then viewed via a transparent portion of the detection module, at 24. In some embodiments, the visible signal can persist for viewing for up to one hour, two hours, twelve hours, twenty four hours, or forty eight hours.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. While the embodiments have been particularly shown and described, it will be understood that various changes in form and details may be made.

For example, any of the sample input modules, sample preparation modules, amplification modules, heater assemblies, and detection modules shown and described herein can be used in any suitable diagnostic device. Such devices can include, for example, a single-use device that can be used in a point-of-care setting and/or in a user's home. Similarly stated, in some embodiments, the device (and any of the other devices shown and described herein) can be configured for use in a decentralized test facility. Further, in some embodiments, any of the sample input modules, sample preparation modules, amplification modules, heater assemblies, and detection modules shown and described herein can be included within a CLIA-waived device and/or can facilitate the operation of a device in accordance with methods that are CLIA waived. Similarly stated, in some embodiments, the sample input modules, the sample preparation modules, the amplification modules, and the detection modules shown and described herein can facilitate operation of a device in a sufficiently simple manner that can produce results with sufficient accuracy to pose a limited likelihood of misuse and/or to pose a limited risk of harm if used improperly. In some embodiments, the sample input modules, the sample preparation modules, the amplification modules, and the detection modules shown and described herein can be used in any of the diagnostic devices shown and described in International Patent Publication No. WO2016/109691, entitled "Devices and Methods for Molecular Diagnostic Testing," which is incorporated herein by reference in its entirety," which is incorporated herein by reference in its entirety.

The devices and methods described herein can be used to analyze any suitable type of biological sample, such as a tissue sample (e.g., a blood sample). In some cases, the biological sample comprises a bodily fluid taken from a subject. In some cases, the bodily fluid includes one or more cells comprising nucleic acids. In some cases, the one or more cells comprise one or more microbial cells, including, but not limited to, bacteria, archaebacteria, protists, and fungi. In some cases, the biological sample includes one or more virus particles. In some cases, the biological sample includes one or more microbes that causes a sexually-transmitted disease. A sample may comprise a sample from a subject, such as whole blood; blood products; red blood cells; white blood cells; buffy coat; swabs; urine; sputum; saliva; semen; lymphatic fluid; endolymph; perilymph; gastric juice; bile; mucus; sebum; sweat; tears; vaginal secretion; vomit; feces; breast milk; cerumen; amniotic fluid; cerebrospinal fluid; peritoneal effusions; pleural effusions; biopsy samples; fluid from cysts; synovial fluid; vitreous humor; aqueous humor; bursa fluid; eye washes; eye aspirates; plasma; serum; pulmonary lavage; lung aspirates;

animal, including human, tissues, including but not limited to, liver, spleen, kidney, lung, intestine, brain, heart, muscle, pancreas, cell cultures, as well as lysates, extracts, or materials and fractions obtained from the samples described above or any cells and microorganisms and viruses that may be present on or in a sample. A sample may include cells of a primary culture or a cell line. Examples of cell lines include, but are not limited to 293-T human kidney cells, A2870 human ovary cells, A431 human epithelium, B35 rat neuroblastoma cells, BHK-21 hamster kidney cells, BR293 human breast cells, CHO chinese hamster ovary cells, CORL23 human lung cells, HeLa cells, or Jurkat cells. The sample may include a homogeneous or mixed population of microbes, including one or more of viruses, bacteria, protists, monerans, chromalveolata, archaea, or fungi. The biological sample can be a urine sample, a vaginal swab, a cervical swab, an anal swab, or a cheek swab. The biological sample can be obtained from a hospital, laboratory, clinical or medical laboratory.

The devices and methods described herein, however, are not limited to performing a molecular diagnostic test on human samples. In some embodiments, any of the devices and methods described herein can be used with veterinary samples, food samples, and/or environmental samples. Examples of environmental sources include, but are not limited to agricultural fields, lakes, rivers, water reservoirs, air vents, walls, roofs, soil samples, plants, and swimming pools. Examples of industrial sources include, but are not limited to clean rooms, hospitals, food processing areas, food production areas, food stuffs, medical laboratories, pharmacies, and pharmaceutical compounding centers. Examples of subjects from which polynucleotides may be isolated include multicellular organisms, such as fish, amphibians, reptiles, birds, and mammals. Examples of mammals include primates (e.g., apes, monkeys, gorillas), rodents (e.g., mice, rats), cows, pigs, sheep, horses, dogs, cats, or rabbits. In some examples, the mammal is a human.

In some embodiments, any of the devices or methods described herein can include a sample buffer (e.g., within a sample preparation module, sample transfer manifold, or reagent module) and/or can mix a sample buffer with the biological sample. In some cases, the sample buffer can include bovine serum albumin and/or a detergent. In some cases, the sample buffer includes about 0.1% to 5% bovine serum albumin. In some cases, the sample buffer includes about 0.1%, 0.2%, 0.3%, 0.4%, 0.5%, 1%, 1.5%, 2%, 2.5%, 3%, 4%, or 5% bovine serum albumin. In some cases, the sample buffer includes about 0.1% to 20% detergent. In some cases, the sample buffer includes about 1%, 2%, 3%, 4%, 5%, 6%, 7%, 8%, 9%, or 10% detergent. In some cases, the detergent is Tween-20. The choice of sample buffer to be used may depend on the intended method. For example, the choice of sample buffer may different when a wash step will be used to when a wash step is not used. If a wash step will not be used then the sample buffer may be a buffer suitable for lysis and subsequent PCR reactions.

In some embodiments, a sample buffer can include Tris HCL, Tween-80, BSA, Proclin and Antifoam SE-15. In some embodiments, a sample buffer may have a composition of: 50 mM Tris pH 8.4, Tween-80, 2% (w/v), BSA, 0.25% (w/v), Proclin 300 0.03% (w/v), and Antifoam SE-15, 0.002% (v/v) made up in purified water. Tris HCL is a common buffer for PCR. When it is heated during thermocycling, the pH may drop, for example, a Tris buffer with pH of 8.4 at a temperature of 25° C. may drop to a pH of about ~7.4 when heated to about 95° C. The range of concentrations could be from 0.1 mM to 1 M. The pH range could be from 6 to 10. Any other PCR compatible buffer could be used, for example HEPES. Proclin 300 is a broad spectrum antimicrobial used as a preservative to ensure a long shelf life of the collection media. It could be used from 0.01% (w/v) to 0.1% (w/v). Many other antimicrobials are known in the art and could be used in a sample buffer. In some embodiments, a reagent or wash buffer can include Antifoam SE-15 to reduce foaming during manufacturing and fluidic movement through the device. It could be used from 0.001% (v/v) to 1% (v/v). Any other antifoam agent could also be used, for example, Antifoam 204, Antifoam A, Antifoam B, Antifoam C, or Antifoam Y-30.

In some embodiments, any of the amplification modules described can be configured to conduct a "rapid" PCR (e.g., completing at least 30 cycles in less than about 10 minutes), and rapid production of an output signal (e.g., via a detection module). Similarly stated, the amplification modules described herein can be configured to process volumes, to have dimensional sizes and/or be constructed from materials that facilitates a rapid PCR or amplification in less than about 10 minutes, less than about 9 minutes, less than about 8 minutes, less than about 7 minutes, less than about 6 minutes, or any range therebetween, as described herein.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or microinstructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

The processor included within the control module 4900 (and any of the processors and/or controllers described herein) can be any processor configured to, for example, write data into and read data from the memory of the controller, and execute the instructions and/or methods stored within the memory. Furthermore, the processor can be configured to control operation of the other modules within the controller (e.g., the temperature feedback module and the flow module). Specifically, the processor can receive a signal including temperature data, current measurements or the like and determine an amount of power and/or current to be supplied to each heater assembly, the desired timing and sequence of the piston pulses and the like. For example, in some embodiments, the controller can be an 8-bit PIC microcontroller, which will control the power delivered to various heating assemblies and components within the amplification module 4600. This microcontroller can also contain code for and/or be configured to minimize the instantaneous power requirements on the power source.

In other embodiments, the processor (and any of the processors described herein) can be, for example, an application-specific integrated circuit (ASIC) or a combination of ASICs, which are designed to perform one or more specific functions. In yet other embodiments, the microprocessor can be an analog or digital circuit, or a combination of multiple circuits.

The memory device of the controller (and any of the memory devices described herein) can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules (the pressure feedback module and the position feedback module) can be implemented by the processor and/or stored within the memory.

Although various embodiments have been described as having particular features and/or combinations of components, other embodiments are possible having a combination of any features and/or components from any of embodiments as discussed above.

For example, although the substrate 4640 is not shown as defining an aperture, in other embodiments, the substrate 4640 (or any of the other substrates shown or described herein) can define an aperture similar to the aperture 1641 shown and described with reference to the amplification module 1600.

Any of the devices and methods described herein can be utilized to detect the presence or absence of nucleic acids associated with one or more bacterial cells in a biological sample. In some embodiments, the one or more bacterial cells are pathogens. In some embodiments, the one or more bacterial cells are infectious. Non-limiting examples of bacterial pathogens that can be detected include Mycobacteria (e.g., *M. tuberculosis, M. bovis, M. avium, M. leprae,* and *M. africanum*), *rickettsia, mycoplasma, chlamydia,* and *legionella*. Some examples of bacterial infections include, but are not limited to, infections caused by Gram positive bacillus (e.g., *Listeria, Bacillus* such as *Bacillus anthracis, Erysipelothrix* species), Gram negative bacillus (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio* and *Y ersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, and *Neisseria* species. Specific examples of infectious bacteria include, but are not limited to: *Helicobacter pyloris, Legionella pneumophilia, Mycobacterium tuberculosis, Mycobacterium avium, Mycobacterium intracellulare, Mycobacterium kansaii, Mycobacterium gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pneumoniae, Haemophilus influenzae, Bacillus antracis, Erysipelothrix rhusiopathiae, Clostridium tetani, Enterobacter aerogenes, Klebsiella pneumoniae, Pasturella multocida, Fusobacterium nucleatum, Streptobacillus moniliformis, Treponema pallidum, Treponema pertenue, Leptospira, Rickettsia,* and *Actinomyces israelii, Acinetobacter, Bacillus, Bordetella, Borrelia, Brucella, Campylobacter, Chlamydia, Chlamydophila, Clostridium, Corynebacterium, Enterococcus, Haemophilus, Helicobacter, Mycobacterium, Mycoplasma, Stenotrophomonas, Treponema, Vibrio, Yersinia, Acinetobacter baumanii, Bordetella pertussis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Corynebacterium diphtheriae, Enterobacter sazakii, Enterobacter agglomerans, Enterobacter cloacae, Enterococcus faecalis, Enterococcus faecium, Escherichia coli, Francisella tularensis, Helicobacter pylori, Legionella pneumophila, Leptospira interrogans, Mycobacterium leprae, Mycobacterium tuberculosis, Mycobacterium ulcerans, Mycoplasma pneumoniae, Pseudomonas aeruginosa, Rickettsia rickettsii, Salmonella typhi, Salmonella typhimurium, Salmonella enterica, Shigella sonnei, Staphylococcus epidermidis, Staphylococcus saprophyticus, Stenotrophomonas maltophilia, Vibrio cholerae, Yersinia pestis,* and the like. In some instances, the infectious bacteria is *Neisseria gonorrhoeae* or *Chlamydia trachomatis*.

Any of the devices and methods described herein can be utilized to detect the presence or absence of nucleic acids associated with one or more viruses in a biological sample. Non-limiting examples of viruses include the herpes virus (e.g., human cytomegalomous virus (HCMV), herpes simplex virus I (HSV-1), herpes simplex virus 2 (HSV-2), varicella zoster virus (VZV), Epstein-Barr virus), influenza A virus and Hepatitis C virus (HCV) or a picornavirus such as Coxsackievirus B3 (CVB3). Other viruses may include, but are not limited to, the hepatitis B virus, HIV, poxvirus, hepadavirus, retrovirus, and RNA viruses such as flavivirus, togavirus, coronavirus, Hepatitis D virus, orthomyxovirus, paramyxovirus, rhabdovirus, bunyavirus, filo virus, Adenovirus, Human herpesvirus, type 8, Human papillomavirus, BK virus, JC virus, Smallpox, Hepatitis B virus, Human bocavirus, Parvovirus B 19, Human astrovirus, Norwalk virus, coxsackievirus, hepatitis A virus, poliovirus, rhinovirus, Severe acute respiratory syndrome virus, Hepatitis C virus, yellow fever virus, dengue virus, West Nile virus, Rubella virus, Hepatitis E virus, and Human immunodeficiency virus (HIV). In some embodiments, the virus is an enveloped virus. Examples of such enveloped viruses include, but are not limited to, viruses that are members of the hepadnavirus family, herpesvirus family, iridovirus family, poxvirus family, flavivirus family, togavirus family, retrovirus family, coronavirus family, filovirus family, rhabdovirus family, bunyavirus family, orthomyxovirus family, paramyxovirus family, and arenavirus family. Other examples include, but are not limited to, Hepadnavirus hepatitis B virus (HBV), woodchuck hepatitis virus, ground squirrel (Hepadnaviridae) hepatitis virus, duck hepatitis B virus, heron hepatitis B virus, Herpesvirus herpes simplex virus (HSV) types 1 and 2, varicellazoster virus, cytomegalovirus (CMV), human cytomegalovirus (HCMV), mouse cytomegalovirus (MCMV), guinea pig cytomegalovirus (GPCMV), Epstein-Barr virus (EBV), human herpes virus 6 (HHV variants A and B), human herpes virus 7 (HHV-7), human herpes virus 8 (HHV-8), Kaposi's sarcoma—associated herpes virus (KSHV), B virus Poxvirus vaccinia virus, variola virus, smallpox virus, monkeypox virus, cowpox virus, camelpox virus, ectromelia virus, mousepox virus, rabbitpox viruses, raccoon pox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, Yabapox virus, Flavivirus dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, Kyasanur Forest disease virus, Togavirus, Venezuelan equine encephalitis (VEE) virus, chikungunya virus, Ross River virus, Mayaro virus, Sindbis virus, rubella virus, Retrovirus human immunodeficiency virus (HIV) types 1 and 2, human T cell leukemia virus (HTLV) types 1, 2, and 5, mouse mammary tumor virus (MMTV), Rous sarcoma virus (RSV), lentiviruses, Coronavirus, severe acute respiratory syndrome (SARS) virus, Filovirus Ebola virus, Marburg virus, Metapneumoviruses (MPV) such as human metapneumovirus (HMPV), Rhabdovirus rabies virus, vesicular stomatitis virus, Bunyavirus, Crimean-Congo hemorrhagic fever virus, Rift Valley fever virus, La Crosse virus, Hantaan virus, Orthomyxovirus, influenza virus (types A, B, and C), Paramyxovirus, parainfluenza virus (PIV types 1, 2 and 3), respiratory syncytial virus (types A and B), measles virus, mumps virus, Arenavirus, lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Punta torn virus (PTV), Tacaribe virus and Tamiami virus. In some embodiments, the virus is a non-enveloped virus, examples of which include, but are not limited to, viruses that are members of the parvovirus family, circovirus family, polyoma virus family, papillomavirus family, adenovirus family, iridovirus family, reovirus family, birnavirus family, calicivirus family, and picornavirus family. Specific examples include, but are not limited to, canine parvovirus, parvovirus B19, porcine circovirus type 1 and 2, BFDV (Beak and Feather Disease virus, chicken anaemia virus, Polyomavirus, simian virus 40 (SV40), JC virus, BK virus, Budgerigar fledgling disease virus, human papillomavirus, bovine papillomavirus (BPV) type 1, cotton tail rabbit papillomavirus, human adenovirus (HAdV-A, HAdV-B, HAdV-C, HAdV-D, HAdV-E, and HAdV-F), fowl adenovirus A, bovine adenovirus D, frog adenovirus, Reovirus, human orbivirus, human coltivirus, mammalian orthoreovirus, bluetongue virus, rotavirus A, rotaviruses (groups B to G), Colorado tick fever virus, aquareovirus A, cypovirus 1, Fiji disease virus, rice dwarf virus, rice ragged stunt virus, idnoreovirus 1, mycoreovirus 1, Birnavirus, bursal disease virus, pancreatic necrosis virus, Calicivirus, swine vesicular exanthema virus, rabbit hemorrhagic disease virus, Norwalk virus, Sapporo virus, Picornavirus, human polioviruses (1-3), human coxsackieviruses A1-22, 24 (CA1-22 and CA24, CA23 (echovirus 9)), human coxsackieviruses (B1-6 (CB1-6)), human echoviruses 1-7, 9, 11-27, 29-33, vilyuish virus, simian enteroviruses 1-18 (SEVI-18), porcine enteroviruses 1-11 (PEV1-11), bovine enteroviruses 1-2 (BEVI-2), hepatitis A virus, rhinoviruses, hepatoviruses, cardio viruses, aphthoviruses and echoviruses. The virus may be phage. Examples of phages include, but are not limited to T4, TS, λ phage, T7 phage, G4, P1, φ6, *Thermoproteus tenax* virus 1, M13, MS2, Qβ, φ X174, Φ29, PZA, Φ15, BS32, B103, M2Y (M2), Nf, GA-I, FWLBc1, FWLBc2, FWLLm3, B4. The reference database may comprise sequences for phage that are pathogenic, protective, or both. In some cases, the virus is selected from a member of the Flaviviridae family (e.g., a member of the Flavivirus, Pestivirus, and Hepacivirus genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Arna virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, Tamana bat virus, and the Cell fusing agent virus. In some cases, the virus is selected from a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Whitewater Arroyo virus, Chapare virus, and Lujo virus. In some cases, the virus is selected from a member of the Bunyaviridae family (e.g., a member of the Hantavirus, Nairovirus, Orthobunyavirus, and Phlebovirus genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus. In some cases, the virus is selected from a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the Alphavirus genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O'nyong'nyong virus, and the chikungunya virus; a member of the Poxyiridae family (e.g., a member of the Orthopoxvirus genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or HINI swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picomaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types I and 2), and human T-lymphotropic virus Types I and II (HTLV-1 and HTLV-2, respectively).

Any of the devices and methods described herein can be utilized to detect the presence or absence of nucleic acids associated with one or more fungi in a biological sample. Examples of infectious fungal agents include, without limitation *Aspergillus, Blastomyces, Coccidioides, Cryptococcus, Histoplasma, Paracoccidioides, Sporothrix*, and at least three genera of *Zygomycetes*. The above fungi, as well as many other fungi, can cause disease in pets and companion animals. The present teaching is inclusive of substrates that contact animals directly or indirectly. Examples of organisms that cause disease in animals include *Malassezia furfur,* *Epidermophyton floccosur, Trichophyton mentagrophytes, Trichophyton rubrum, Trichophyton tonsurans, Trichophyton equinum, Dermatophilus congolensis, Microsporum canis, Microsporu audouinii, Microsporum gypseum, Malassezia ovale, Pseudallescheria, Scopulariopsis, Scedosporium*, and *Candida albicans*. Further examples of fungal infectious agent include, but are not limited to, Aspergillus, Blastomyces dermatitidis, *Candida*, Coccidioides immitis, Cryptococcus neoformans, Histoplasma capsulatum var. capsulatum, Paracoccidioides brasiliensis, Sporothrix schenckii, *Zygomycetes* spp., Absidia corymbifera, Rhizomucor pusillus, or Rhizopus arrhizus.

Any of the devices and methods described herein can be utilized to detect the presence or absence of nucleic acids associated with one or more parasites in a biological sample. Non-limiting examples of parasites include *Plasmodium*, Leishmania, Babesia, *Treponema, Borrelia, Trypanosoma, Toxoplasma gondii, Plasmodium falciparum, P. vivax, P. ovale, P. malariae, Trypanosoma* spp., or *Legionella* spp. In some cases, the parasite is *Trichomonas vaginalis*.

What is claimed is:

1. A method of detecting a target amplicon using a self-contained molecular diagnostic test device, the method comprising:

loading, via an opening defined by an actuator of the molecular diagnostic test device, a biological sample into a sample input volume of the molecular diagnostic test device;

moving, after the loading, a lid relative to the actuator from an opened position to a closed position, the lid including a lock protrusion within a mating slot of the actuator, the lock protrusion being engaged with a lock surface of the molecular diagnostic test device to retain the actuator in a first position when the lid is in the opened position, the lid covering the opening and the lock protrusion of the lid being disengaged from the lock surface of the molecular diagnostic test device when the lid is in the closed position;

actuating the molecular diagnostic test device by moving the actuator from the first position to a second position to cause the molecular diagnostic test device to:
  convey the biological sample from the sample input volume to an amplification module within the molecular diagnostic test device;
  heat a portion of the amplification module to amplify a nucleic acid from a plurality of nucleic acid molecules extracted from the biological sample to produce a detection solution containing the target amplicon;
  convey the detection solution through a detection channel of a detection module, the detection channel defined at least in part by a detection surface, the detection surface including a plurality of capture probes to which a first portion of the target amplicon is bound;
  convey through the detection channel a first reagent formulated to cause production of a signal indicating a presence of the target amplicon, the first reagent being bound to a second portion of the target amplicon when conveyed through the detection channel; and
  convey through the detection channel a second reagent formulated to catalyze the production of the signal when the second reagent is in contact with the first reagent; and
reading a result associated with the signal.

2. The method of claim 1, wherein:
the reading includes viewing the signal via a transparent portion of the detection module, the transparent portion of the detection module being a cover opposite the detection surface, a depth of the detection channel between the cover and the detection surface being between 0.125 mm and 0.750 mm.

3. The method of claim 1, wherein the detection channel includes an entrance portion and a detection portion, the detection portion including the detection surface, the entrance portion upstream of the detection surface, the actuating the molecular diagnostic test device further causes the molecular diagnostic test device to:
  heat a substrate defining the entrance portion and the detection portion.

4. The method of claim 1, wherein the detection channel is devoid of a porous material.

5. The method of claim 1, wherein the method is performed using the self-contained molecular diagnostic test device without any external instrument.

6. The method of claim 5, further comprising:
discarding, after the reading, the self-contained molecular diagnostic test device.

7. The method of claim 1, wherein the second reagent includes a precipitating substrate formulated to produce the signal by producing an insoluble colored product when the second reagent is in contact with the first reagent.

8. The method of claim 7, wherein the precipitating substrate is any one of TMB (3,3',5,5' tetramethylbenzidine), DAB (3,3' diaminobenzidine), 4 CN (4-chloro-1-napthol), or BCIP (5-bromo-4-chloro-3-indolyl-phosphate).

9. The method of claim 7, wherein:
the signal is a visible signal that is present through a transparent portion of the detection module for at least two hours.

10. The method of claim 7, wherein the detection surface defines at least a portion of a boundary of the detection channel through which the detection solution, the first reagent, and the second reagent are conveyed, the actuating of the molecular diagnostic test device further causes the molecular diagnostic test device to:
  convey, after the first reagent is conveyed through the detection channel, a wash solution through the detection channel.

11. The method of claim 7, wherein:
the first reagent is stored within the molecular diagnostic test device within a first container and the precipitating substrate is stored within the molecular test device within a second container; and
the actuating of the molecular diagnostic test device further causes the molecular diagnostic test device to:
  actuate a fluid pump within the molecular diagnostic test device at a first time to produce a flow of the first reagent from the first container into the detection module; and
  actuate the fluid pump at a second time to produce a flow of the precipitating substrate from the second container into the detection module.

12. The method of claim 1, wherein:
the lock protrusion of the lid is a first lock protrusion; and
the lid includes a second lock protrusion that engages a housing when the lid is in the closed position to prevent movement of the lid from the closed position back towards the opened position.

13. The method of claim 12, wherein the second lock protrusion expands within a channel defined by the housing to engage the housing when the lid is moved from the opened position to the closed position.

14. The method of claim 13, wherein the actuator includes a lock protrusion that irreversibly engages a shoulder of the housing to maintain the actuator in the second position.

15. A method of detecting a target amplicon using a self-contained molecular diagnostic test device, the method comprising:
  loading a biological sample into a sample input volume of the molecular diagnostic test device, the molecular diagnostic test device including a first container containing a first reagent and a second container containing a second reagent, the first container and the second container being within a housing of the molecular diagnostic test device;
  actuating the molecular diagnostic test device by moving a reagent actuator coupled to the housing from a first position to a second position, movement of the reagent actuator causing the first reagent to be released from the first container and the second reagent to be released from the second container, a lock protrusion of the reagent actuator irreversibly engaging a shoulder of the housing to maintain the reagent actuator in the second position, the actuating further causing the molecular diagnostic test device to:
    heat the biological sample within a lysis module within the molecular diagnostic test device to lyse a portion of the biological sample to produce an input sample;
    heat the input sample within an amplification module within the molecular diagnostic test device to amplify a nucleic acid from a plurality of nucleic acid molecules extracted from the biological sample to produce a detection solution containing a target amplicon;
    convey the detection solution through a detection channel defined at least in part by a detection surface, the detection surface including a plurality of capture probes that capture the target amplicon; and
    react, within the detection channel, the captured target amplicon, the first reagent, and the second reagent to produce of a signal indicating a presence of the target amplicon, the first reagent formulated to cause production of the signal, the second reagent including a precipitating substrate formulated produce the signal by producing an insoluble colored product when the second reagent is contacted with the first reagent; and reading, via a status window of the housing, a result associated with the signal.

16. The method of claim 15, wherein the precipitating substrate is any one of TMB (3,3',5,5' tetramethylbenzidine), DAB (3,3' diaminobenzidine), 4 CN (4-chloro-1-napthol), or BCIP (5-bromo-4-chloro-3-indolyl-phosphate).

17. The method of claim 15, wherein the signal is a visible signal that is present through the status window of the housing for at least two hours.

18. The method of claim 15, wherein the detection channel includes an entrance portion and a detection portion, the detection portion including the detection surface, the entrance portion upstream of the detection surface, the actuating of the molecular diagnostic test device further causes the molecular diagnostic test device to:

heat a substrate defining the entrance portion and the detection portion.

19. The method of claim 15, wherein
the molecular diagnostic test device reacts the captured target amplicon, the first reagent, and the second reagent by:

actuating a fluid pump within the molecular diagnostic test device at a first time to produce a flow of the first reagent into the detection channel; and actuating the fluid pump at a second time to produce a flow of the second reagent into the detection channel.

20. The method of claim 15, further comprising:
discarding, after the reading, the self-contained molecular diagnostic test device.

21. The method of claim 15, further comprising:
moving, after the loading, a lid from an opened position to a closed position, the lid including a side rail that slides within a corresponding channel defined by the housing of the molecular test device when the lid is moved from the opened position to the closed position, the lid covering the sample input volume when in the closed position, a lock protrusion of the lid expanding within the channel to engage a portion of a housing of the molecular diagnostic test device to maintain the lid in the second position.

* * * * *

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
tctcgtaaag ggcagcccgc aag                                              23

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2 ggggggtct cgtaaagggc agcccgcaag                                        30
```